(12) United States Patent
Schupp et al.

(10) Patent No.: US 6,924,106 B2
(45) Date of Patent: Aug. 2, 2005

(54) RIFAMYCIN BIOSYNTHESIS GENE CLUSTER

(75) Inventors: Thomas Schupp, Mohlin (CH); Christiane Toupet, Mulhouse (FR); Nathalie Engel, Rixheim (FR)

(73) Assignee: Novartis AG, Basel (CH)

( * ) Notice: Subject to any disclaimer, the term of this patent is extended or adjusted under 35 U.S.C. 154(b) by 384 days.

(21) Appl. No.: 10/042,665

(22) Filed: Jan. 9, 2002

(65) Prior Publication Data

US 2005/0053927 A1 Mar. 10, 2005

Related U.S. Application Data

(63) Continuation of application No. 09/242,744, filed as application No. PCT/EP97/04495 on Aug. 18, 1997, now abandoned.

(30) Foreign Application Priority Data

Aug. 20, 1996 (DE) .......................................... 968 10 551

(51) Int. Cl.$^7$ ........................... C12Q 1/68; C07H 21/04
(52) U.S. Cl. ........................ 435/6; 536/23.2; 536/23.1; 435/320.1; 435/252.3; 435/252.33
(58) Field of Search ........................... 435/252.3, 320.1, 435/6, 252.33; 536/23.1, 24.3, 23.2

(56) References Cited

U.S. PATENT DOCUMENTS

5,763,569 A * 6/1998 Brown et al. ................ 530/324

FOREIGN PATENT DOCUMENTS

| WO | WO 87/03907 | 7/1987 |
| WO | WO 95/08548 | 3/1995 |

OTHER PUBLICATIONS

Donadio et al., Science 252:675–679 (1991).*
Aparicio et al., Gene, vol. 169, "Organization of the biosynthetic gene cluster for rapamycin in Streptomyces hygroscopicus: analysis of the enzymatic domains in the modular polyketide synthase," pp. 9–16 (1996).
Bhat K.S., Gene, vol. 134, "Generation of a plasmid vector for deletion cloning by rapid multiple site–directed mutagenesis," pp. 83–87 (1993).
Birnboim H.C., Methods in Enzymology, vol. 100, "A Rapid Alkaline Extraction Method for the Isolation of Plasmid DNA," pp. 243–255 (1983).
Bonfield and Staden, Nucleic Acids Research, vol. 23 (8), "The application of numerical estimates of base calling accuracy to DNA sequencing projects," pp. 1406–1410 (1995).
Chater K., Ciba Foundation Symposium 171, "Genetic regulation of secondary metabolic pathways in Streptomyces," in Secondary Metabolites: Their Function and Evolution, John Wiley & Sons, pp. 144–162 (1992).

Donadio and Katz, Gene, vol. 111, "Organization of the enzymatic domains in the multifunctional polyketide synthase involved in erythromycin formation in Saccharopolyspora erythraea," pp. 51–60 (1992).
Donadio et al., Science, vol. 252, "Modular Organization of Genes Required for Complex Polyketide Biosynthesis," pp. 675–679 (1991).
Ghisalba et al., "The Rifamycins: Properties, Biosynthesis, and Fermentation," in Biotechnology of Industrial Antibiotics, E.J. Vandamme (Ed.), pp. 281–327, Marcel Dekker, Inc. (1984).
Hopwood D.A., Current Opinion in Biotechnology, vol. 4, "Genetic engineering of Streptomyces to create hybrid antibiotics," pp. 531–537 (1993).
Hopwood et al.(ed.), Genetic Manipulation of Streptomyces—A Laboratory Manual, The John Innes Foundation, Norwich, pp. i–xii (1985)—preface and table of contents provided.
Hopwood et al., Ciba Foundation Symposium 171, "Genes for polyketide secondary metabolic pathways in microorganisms and plants," in Secondary Metabolites: Their Function and Evolution, John Wiley & Sons, pp. 88–112 (1992).
Kieser and Melton, Gene, vol. 65, "Plasmid plJ699, a multi–copy positive–selection vector for Streptomyces," pp. 83–91 (1988).
Lal et al., Critical Reviews in Microbiology, vol. 21(1), "Rifamycins: Strain Improvement Program," pp. 19–30 (1995).
Lechevalier et al., Int. J. of Systematic Bacteriology, vol. 36 (1), Two New Genera of Nocardioform Actinomycetes: Amycolata gen. Nov. and Amycolatopsis gen nov., pp. 29–37 (1986).
Madon et al., J. of Bacteriology, vol. 173 (20), "Transformation System for Amycolatopsis (Nocardia) mediterranei: Direct Transformation of Mycelium with Plasmid DNA," pp. 6325–6331 (1991).

(Continued)

Primary Examiner—Terry McKelvey
Assistant Examiner—Nancy T. Vogel
(74) Attorney, Agent, or Firm—John T. Prince

(57) ABSTRACT

The present invention primarily relates to a DNA fragment which is obtainable from the gene cluster responsible for rifamycin biosynthesis within the genome of Amycolatopsis mediterranei, and comprises at least one gene or a part of a gene which codes for a polypeptide which is directly or indirectly involved in the biosynthesis of rifamycin, and to a method for preparing said DNA fragment.

The present invention furthermore relates to recombinant DNA molecules which comprise one of the DNA fragments according to the invention, and to the plasmids and vectors derived therefrom. Host organisms transformed with said plasmid or vector DNA are likewise embraced.

7 Claims, No Drawings

OTHER PUBLICATIONS

Pospiech et al., Trends in Genetics, vol. 11 (6), "A versatile quick–prep of genomic DNA from Gram–positive bacteria," pp. 217–128 (1995).

Schupp and Divers, FEMS Microbiology Letters, vol. 36, "Protoplast preparation and regeneration in *Nocardia mediterranei*," pp. 159–162 (1986).

Shupp et al., J. of Bacteriology, vol. 177 (13), "A *Sorangium cellulosum* (Myxobacterium) Gene Cluster for the Biosynthesis of the Macrolide Antibiotic Soraphen A: Cloning, Characterization, and Homology to Polyketide Synthase Genes from Actinomycetes," pp. 3673–3679 (1995).

Schwecke et al., Proc. Natl. Acad. Sci. USA, vol. 92, "The biosynthetic gene cluster for the polyketide immunosuppressant rapamycin," pp. 7839–7843 (1995).

Sensi et al., Farmaco Ed. Sci., vol. 14, "Rifomycin, A New Antibiotic—Preliminary Report," pp. 146–147 (1959).

Smith et al., Methods Enzymol., vol. 151, "Strategies for Mapping and Cloning Macroregions of Mammalian Genomes," pp. 461–489 (1987).

Thiemann et al., Arch. Mikrobiol., vol. 67, "A Proposal for the Transfer of *Streptomyces mediterranei* Margalith and Beretta 1960 to the Genus *Nocardia* as *Nocardia mediterranea* (Margalith and Beretta) Comb. Nov.," pp. 147–155 (1969).

Tsoi and Khosla, Chemistry & Biology, vol. 2, "Combinatorial biosynthesis of 'unnatural' natural products: the polyketide example," pp. 355–362 (1995).

Wahl et al., Proc. Natl. Acad. Sci. USA, vol. 84, "Cosmid vectors for rapid genomic walking, restriction mapping, and gene transfer," pp. 2160–2164 (1987).

Wehrli W., "Ansamycins—Chemistry, Biosynthesis, and Biological Activity," in *Topics in Current Chemistry*, vol. 72, pp. 21–49 (1971).

Wehrli and Staehelin, Bacteriological Reviews, vol. 35 (3), "Actions of the Rifamycins," pp. 290–309 (1971).

Stratmann et al., Microbiology (1999), 145, 3365–3375.

Schupp et al., FEMS Microbiology Letters 159 (1998) 201–207.

Yu, T. et al., (1999), PNAS USA 96, 9051–9056.

* cited by examiner

SEQUENCE LISTING

<160> NUMBER OF SEQ ID NOS: 9

<210> SEQ ID NO 1
<211> LENGTH: 5676
<212> TYPE: DNA
<213> ORGANISM: Amcylatopsis mediterranei

<400> SEQUENCE: 1

```
ggtacccggt gttcgcgacg gcgttcgacg aggcttgcga gcagctggac gtctgtctgg      60
ccggccgtgc cgggcaccgc gtgcgggacg tcgtgctcgg cgaagtgccc gccgaaaccg     120
ggctgctgaa ccagacggtc ttcacccaag ccgggctgtt cgcggtggag agcgcgctgt     180
tccggctcgc cgaatcctgg ggtgtccggc cggacgtggt gctcggccac tccatcgggg     240
agatcaccgc cgcgtatgcc gcgggcgtct tctcgctgcc ggacgccgcc cggatcgtcg     300
cggcgcgcgg ccggctgatg caggcgctgg cgccgggcgg ggcgatggtc gccgtcgccg     360
cctccgaagc cgaggtggcc gaactgctcg gcgacggcgt ggaactcgcc gccgtcaacg     420
gcccttcggc ggtagtcctt tccggggacg cggacgcggt cgtcgcggcc gccgcccgca     480
tgcgcgagcg cgggcacaag accaagcagc tcaaggtttc gcacgcgttc cactccgcgc     540
ggatggcgcc gatgctggcg gagttcgccg ccgagctggc cggcgtgacg tggcgcgagc     600
```

```
cggagatccc ggtggtctcc aacgtgaccg gccggttcgc cgagcccggc gaactgaccg      660
agccgggcta ctgggccgag cacgtgcggc ggccggtgcg gttcgccgag ggcgtcgcgg      720
ccgcgacgga gtccggcggc tcgctgttcg tggagctcgg gccggggggcg cgctgaccg     780 ccctcgtcga ggagacggcc gaggtcacct gcgtcgcggc cctgcgggac gaccgcccgg      840
aggtcaccgc gctgatcacc gcggtcgccg agctgttcgt ccgcggggtt gcggtcgatt      900
ggccggccct gctgccgccg gtcaccgggt tcgtcgacct gccgaagtac gccttcgacc      960
agcagcacta ttggctgcag cccgccgcgc aggccacgga cgcggcctcg ctcgggcagg     1020
tcgcggccga ccaccgctg ctgggcgcgg tggtccggct gccgcagtcg acggcctgg      1080 tcttcacctc gcggctgtca ttgaaatcgc acccgtggct ggccgaccac gtcatcggcg      1140
gggtggtgct cgtcgcgggc accgggctcg tcgagctggc cgtccgggcc ggggacgagg      1200
ccggctgccc ggtcctcgaa gaactcgtca tcgaggctcc gctggtcgtc cccgaccacg      1260
gcggggtccg gatccaggtc gtcgtggggg caccggggga gaccggttcg cgcgcggtcg      1320
aggtgtactc cctgcgcgag gacgccggtg ccgaagtgtg ggcccggcac gccaccgggt      1380
tcctggctgc gacgccgtcg cagcacaagc cgttcgactt caccgcctgg ccgccgcccg      1440
gcgtcgagcg cgtcgacgtc gaggacttct acgacggctt cgtcgaccgc gggtacgcct      1500
acgggccgtc gttccggggc ctgcgggcgg tgtggcggcg cggcgacgaa gtgttcgccg      1560
aggtcgccct ggccgaggac gaccgcgcgg acgcggcccg gttcggcatc caccccggcc      1620
tgctggacgc cgccctgcac gcgggcatgg ccggtgccac caccacggaa gagcccggcc      1680
ggccggtgct gccgttcgcc tggaacggcc tggtgctgca cgcggccggg gcgtccgcgc      1740
tgcgggtccg gctcgccccg agcggtccgg acgccctgtc ggtcgaggcc gcggacgagg      1800
ccggcggtct cgttgtgacg gcggactcgc tggtctcccg gccggtgtcg gccgaacagc      1860
tgggcgcggc ggcgaaccac gacgcgttgt ccgcgtgga gtggaccgag atttcctcgg      1920
ctggagacgt tccggcggac cacgtcgaag tgctcgaagc cgtcggcgag gatcccctgg      1980
aactgaccgg ccgggtcctg gaggccgtgc agacctggct cgccgacgca gccgacgacg      2040
ctcgcctggt cgtggtgacc cgcggcgccg tccacgaggt gactgaccg gccggtgccg      2100 cggtgtgggg cctgatccgg gccgcgcagg cggaaaaccc ggaccggatc gtgctgctgg      2160
acaccgacgg tgaagtgccg ctaggccggg tgctggccac cggcgagccc caaacagccg      2220
tccgaggcgc cacgctgttc gccccgcggc tggcccgcgc cgaggccgcg gaggcaccgg      2280
cagtgaccgg cgggacggtc ctgatctcgg gcgccggctc gctgggcgcg ctcaccgccc      2340
ggcacctggt cgcccggcac ggagtccggc ggctggtgct cgtcagccgc cgtggccccg      2400
acgccgacgg catggccgaa ctgaccgctg aactcatcgc tcaggcgcc gaggtcgccg      2460 tagtcgcttg cgacctggcc gaccgggacc aggtccgggt actgctggcc gagcaccgcc      2520
cgaacgccgt cgtgcacacg gccggtgttc tcgacgacgg cgtcttcgag tcgctgacgc      2580
gggagcggct ggccaaggtc ttcgcgccca agttactgc tgccaatcac ctcgacgagc      2640
tgacccgcga actggatctt cgcgcgttcg tcgtgttctc ctccgcctcc gggtcttcg      2700 gctccgccgg gcagggcaac tacgccgctg ccaacgccta cctggacgcc gtggtcgcca      2760
accgccgggc cgcgggcctg cccggcacat cgctggcctg ggcctgtgg aacagaccg      2820 acgggatgac cgcgcaccte ggcgacgccg accaggcgcg ggcgagtcgc ggcggggtcc      2880
tcgccatctc acccgccgaa ggcatggagc tgttcgacgc agcgccggac gggctcgtcg      2940
tcccggtcaa gctggacctg cgcaagaccc gcgccggcgg gacggtgccg cacctgctgc      3000
```

```
gcggcctggt ccgcccggga cggcagcagg cccgtccggc gtccactgtg gacaacggac    3060
tggccgggcg actcgccggg ctcgcgccgg cggagcagga ggcgctgctg ctcgacgtcg    3120
tccgcacgca ggtcgcgctg gtgctcgggc acgccgggcc ggaggccgtc cgcgcggaca    3180
cggcgttcaa ggacaccggc ttcgactcgc tgacgtcggt ggaactgcgc aaccggctgc    3240
gcgaggcgag cgggctgaag ctgcccgcga cgctcgtctt cgactacccg acgccggtcg    3300
cgctggcccg ctacctgcgt gacgaattcg cgacacggtg gcaacaact ccggtggcca    3360 ccgcggccgc agcggacgcc ggcgagccga tcgccatcgt cggcatggcg tgccggctgc    3420
cgggcggggt caccgatccc gaaggcctgt ggcgcctggt gcgcgacggc ctcgaagggc    3480
tgtctccctt ccccgaggac cggggctggg acctggagaa cctgttcgac gacgaccccg    3540
accgctccgg cacgacgtac accagccggg gcgggttcct cgacggcgcc ggcctgttcg    3600
acgcgggctt cttcgggatt cgccgcgcg aggcgctggc catggacccg cagcagcggc    3660
tgctgctcga ggcggcctgg gaagccctcg aaggcaccgg tgtcgacccg ggctcgttga    3720
agggcgccga cgtcgggtg ttcgccgggg tgtccaacca gggctatggg atgggcgcgg    3780
atccggccga actggcgggg tacgcgagca cggcgggcgc ttcgagcgtc gtctcgggcc    3840
gagtctcgta cgtcttcggg ttcgaaggac cggcggtcac gatcgacacg gcttgctcgt    3900
cgtcgctggt ggcgatgcac ctggccggc aggcgctgcg gcagggcgag tgctcgatgg    3960
ccctggccgg tggcgtcacg gtgatgggga cgcccggcac gttcgtggag ttcgcgaagc    4020
agcgcggcct ggccggcgac ggccggtgca aggcctacgc cgaaggcgcg gacggcacgg    4080
gctgggccga gggcgtcggg gtcgtcgtgc tggagcggct gtcggtggcg cgcgagcgcg    4140
ggcaccgggt gctggccgtg ctgcgcggca gcgcggtcaa ctccgacggc gcgtccaacg    4200
gcctgaccgc ccccaacggg ccgtcgcagc aacgggtgat ccgccgggcc ctggccggcg    4260
ccggcctcga accgtccgat gtggacatcg tggaagggca cggcaccggg acggcgctgg    4320
gcgacccgat cgaggcgcag gccctgctgg ccacctacgg caaggaccgc gacccggaga    4380
cgccgttgtg gctggggtcg gtgaagtcga acttcggcca cacgcagtcc gcggccggcg    4440
tggccggggt gatcaagatg gtgcaggcgc tgcgccacgg cgtcatgccg cccaccctgc    4500
acgtggaccg gccaccagc caggtcgact ggtccgcggg ggccgtcgaa gtgctgaccg    4560
aggcacggga gtggccgcgg aacggccgtc cgcgccgggc cggggtgtcc tcgttcggga    4620
tcagcggcac gaacgcccac ctgatcatcg aagaagcacc ggccgagcca cagcttgccg    4680
gaccaccgcc ggacggcggt gtggtgccgc tggtcgtctc ggctcgcagc cccggtgccc    4740
tggccggtca ggcgcgtcgg ctggccacgt tcctcggcga cgggcccctt ccgacgtcg    4800 ccggtgcgct gacgagccgc gccctgttcg gcgagcgcgc ggtcgtcgtg gcggattcgg    4860
ccgaggaagc ccgcgccggt ctgggcgcac tggcccgcgg cgaagacgcg ccgggcctgg    4920
tccgcggccg ggtgcccgcg tccggcctgc cgggcaagct cgtgtgggtg ttccccgggc    4980
aggggacgca gtgggtgggc atgggccgcg aactcctcga agagtctccg gtgttcgccg    5040
agcggatcgc cgagtgtgcg gccgcgctgg agccgtggat cggctggtcg ctgttcgacg    5100
tcctccgtgg cgacggtgac ctcgatcggg tcgatgtgct gcagcccgcg tgctttgcgg    5160
tgatggtcgg cttggccgcg gtgtggtcct cggccggggt ggtccccgat gcggtgctcg    5220
gccactccca gggtgagatc gccgcggcgt gcgtgtcggg tgcgttgtcg ctggaggatg    5280
cggcgaaggt ggttgccctg cgcagccagg ccatcgccgc gaagctctcc ggccgcggcg    5340
```

-continued

```
ggatggcttc ggtcgccttg ggcgaagccg atgtggtgtc gcggctggcg gacggggtcg    5400
aggtggctgc cgtcaacggt ccggcgtccg tggtgatcgc gggggatgcc caggccctcg    5460
acgaaacgct ggaagcgctg tccggtgcgg aatccgggc tcggcgggtg cggtggact     5520 acgcctcgca caccggcac gtcgaagaca tcgaagacac cctcgccgaa cgctggccg     5580 ggatcgacgc ccgggcgccg ctggtgccgt tcctctccac cctcaccggc gagtggatcc    5640
gggacgaggg cgtcgtggac ggcggctact ggtacc                              5676
```

<210> SEQ ID NO 2
<211> LENGTH: 1875
<212> TYPE: PRT
<213> ORGANISM: Amycolatopsis mediterranei

<400> SEQUENCE: 2

```
Tyr Pro Val Phe Ala Thr Ala Phe Asp Glu Ala Cys Glu Gln Leu Asp
 1               5                  10                  15

Val Cys Leu Ala Gly Arg Ala Gly His Arg Val Arg Asp Val Val Leu
             20                  25                  30

Gly Glu Val Pro Ala Glu Thr Gly Leu Leu Asn Gln Thr Val Phe Thr
         35                  40                  45

Gln Ala Gly Leu Phe Ala Val Glu Ser Ala Leu Phe Arg Leu Ala Glu
     50                  55                  60

Ser Trp Gly Val Arg Pro Asp Val Val Leu Gly His Ser Ile Gly Glu
 65                  70                  75                  80

Ile Thr Ala Ala Tyr Ala Ala Gly Val Phe Ser Leu Pro Asp Ala Ala
                 85                  90                  95

Arg Ile Val Ala Ala Arg Gly Arg Leu Met Gln Ala Leu Ala Pro Gly
            100                 105                 110

Gly Ala Met Val Ala Val Ala Ser Glu Ala Glu Val Ala Glu Leu
        115                 120                 125

Leu Gly Asp Gly Val Glu Leu Ala Ala Val Asn Gly Pro Ser Ala Val
    130                 135                 140

Val Leu Ser Gly Asp Ala Asp Ala Val Val Ala Ala Ala Arg Met
145                 150                 155                 160

Arg Glu Arg Gly His Lys Thr Lys Gln Leu Lys Val Ser His Ala Phe
                165                 170                 175

His Ser Ala Arg Met Ala Pro Met Leu Ala Glu Phe Ala Ala Glu Leu
            180                 185                 190

Ala Gly Val Thr Trp Arg Glu Pro Glu Ile Pro Val Val Ser Asn Val
        195                 200                 205

Thr Gly Arg Phe Ala Glu Pro Gly Glu Leu Thr Glu Pro Gly Tyr Trp
    210                 215                 220

Ala Glu His Val Arg Arg Pro Val Arg Phe Ala Glu Gly Val Ala Ala
225                 230                 235                 240

Ala Thr Glu Ser Gly Gly Ser Leu Phe Val Glu Leu Gly Pro Gly Ala
                245                 250                 255

Ala Leu Thr Ala Leu Val Glu Glu Thr Ala Glu Val Thr Cys Val Ala
            260                 265                 270

Ala Leu Arg Asp Asp Arg Pro Glu Val Thr Ala Leu Ile Thr Ala Val
        275                 280                 285

Ala Glu Leu Phe Val Arg Gly Val Ala Val Asp Trp Pro Ala Leu Leu
    290                 295                 300

Pro Pro Val Thr Gly Phe Val Asp Leu Pro Lys Tyr Ala Phe Asp Gln
305                 310                 315                 320
```

```
Gln His Tyr Trp Leu Gln Pro Ala Ala Gln Ala Thr Asp Ala Ala Ser
                325                 330                 335

Leu Gly Gln Val Ala Ala Asp His Pro Leu Leu Gly Ala Val Val Arg
            340                 345                 350

Leu Pro Gln Ser Asp Gly Leu Val Phe Thr Ser Arg Leu Ser Leu Lys
            355                 360                 365

Ser His Pro Trp Leu Ala Asp His Val Ile Gly Gly Val Val Leu Val
        370                 375                 380

Ala Gly Thr Gly Leu Val Glu Leu Ala Val Arg Ala Gly Asp Glu Ala
385                 390                 395                 400

Gly Cys Pro Val Leu Glu Leu Val Ile Glu Ala Pro Leu Val Val
                405                 410                 415

Pro Asp His Gly Gly Val Arg Ile Gln Val Val Gly Ala Pro Gly
                420                 425                 430

Glu Thr Gly Ser Arg Ala Val Glu Val Tyr Ser Leu Arg Glu Asp Ala
            435                 440                 445

Gly Ala Glu Val Trp Ala Arg His Ala Thr Gly Phe Leu Ala Ala Thr
        450                 455                 460

Pro Ser Gln His Lys Pro Phe Asp Phe Thr Ala Trp Pro Pro Gly
465                 470                 475                 480

Val Glu Arg Val Asp Val Glu Asp Phe Tyr Asp Gly Phe Val Asp Arg
                485                 490                 495

Gly Tyr Ala Tyr Gly Pro Ser Phe Arg Gly Leu Arg Ala Val Trp Arg
                500                 505                 510

Arg Gly Asp Glu Val Phe Ala Glu Val Ala Leu Ala Glu Asp Asp Arg
            515                 520                 525

Ala Asp Ala Ala Arg Phe Gly Ile His Pro Gly Leu Leu Asp Ala Ala
            530                 535                 540

Leu His Ala Gly Met Ala Gly Ala Thr Thr Glu Glu Pro Gly Arg
545                 550                 555                 560

Pro Val Leu Pro Phe Ala Trp Asn Gly Leu Val Leu His Ala Ala Gly
                565                 570                 575

Ala Ser Ala Leu Arg Val Arg Leu Ala Pro Ser Gly Pro Asp Ala Leu
            580                 585                 590

Ser Val Glu Ala Ala Asp Glu Ala Gly Gly Leu Val Val Thr Ala Asp
            595                 600                 605

Ser Leu Val Ser Arg Pro Val Ser Ala Glu Gln Leu Gly Ala Ala Ala
        610                 615                 620

Asn His Asp Ala Leu Phe Arg Val Glu Trp Thr Glu Ile Ser Ser Ala
625                 630                 635                 640

Gly Asp Val Pro Ala Asp His Val Glu Val Leu Glu Ala Val Gly Glu
                645                 650                 655

Asp Pro Leu Glu Leu Thr Gly Arg Val Leu Glu Ala Val Gln Thr Trp
                660                 665                 670

Leu Ala Asp Ala Ala Asp Asp Ala Arg Leu Val Val Thr Arg Gly
            675                 680                 685

Ala Val His Glu Val Thr Asp Pro Ala Gly Ala Ala Val Trp Gly Leu
        690                 695                 700

Ile Arg Ala Ala Gln Ala Glu Asn Pro Asp Arg Ile Val Leu Leu Asp
705                 710                 715                 720

Thr Asp Gly Glu Val Pro Leu Gly Arg Val Leu Ala Thr Gly Glu Pro
                725                 730                 735
```

-continued

```
Gln Thr Ala Val Arg Gly Ala Thr Leu Phe Ala Pro Arg Leu Ala Arg
            740                 745                 750

Ala Glu Ala Ala Glu Ala Pro Ala Val Thr Gly Gly Thr Val Leu Ile
        755                 760                 765

Ser Gly Ala Gly Ser Leu Gly Ala Leu Thr Ala Arg His Leu Val Ala
    770                 775                 780

Arg His Gly Val Arg Arg Leu Val Leu Val Ser Arg Arg Gly Pro Asp
785                 790                 795                 800

Ala Asp Gly Met Ala Glu Leu Thr Ala Glu Leu Ile Ala Gln Gly Ala
                805                 810                 815

Glu Val Ala Val Val Ala Cys Asp Leu Ala Asp Arg Asp Gln Val Arg
                820                 825                 830

Val Leu Leu Ala Glu His Arg Pro Asn Ala Val His Thr Ala Gly
            835                 840                 845

Lys Val Phe Ala Pro Lys Val Thr Ala Ala Asn His Leu Asp Glu Leu
        850                 855                 860

Thr Arg Glu Leu Asp Leu Arg Ala Phe Val Val Phe Ser Ser Ala Ser
865                 870                 875                 880

Gly Val Phe Gly Ser Ala Gly Gln Gly Asn Tyr Ala Ala Ala Asn Ala
                885                 890                 895

Tyr Leu Asp Ala Val Ala Asn Arg Arg Ala Ala Gly Leu Pro Gly
            900                 905                 910

Thr Ser Leu Ala Trp Gly Leu Trp Glu Gln Thr Asp Gly Met Thr Ala
            915                 920                 925

His Leu Gly Asp Ala Asp Gln Ala Arg Ala Ser Arg Gly Gly Val Leu
        930                 935                 940

Ala Ile Ser Pro Ala Glu Gly Met Glu Leu Phe Asp Ala Ala Pro Asp
945                 950                 955                 960

Gly Leu Val Val Pro Val Lys Leu Asp Leu Arg Lys Thr Arg Ala Gly
                965                 970                 975

Gly Thr Val Pro His Leu Leu Arg Gly Leu Val Arg Pro Gly Arg Gln
            980                 985                 990

Gln Ala Arg Pro Ala Ser Thr Val Asp Asn Gly Leu Ala Gly Arg Leu
        995                 1000                1005

Ala Gly Leu Ala Pro Ala Glu Gln Glu Ala Leu Leu Leu Asp Val Val
    1010                1015                1020

Arg Thr Gln Val Ala Leu Val Leu Gly His Ala Gly Pro Glu Ala Val
1025                1030                1035                1040

Arg Ala Asp Thr Ala Phe Lys Asp Thr Gly Phe Asp Ser Leu Thr Ser
                1045                1050                1055

Val Glu Leu Arg Asn Arg Leu Arg Glu Ala Ser Gly Leu Lys Leu Pro
            1060                1065                1070

Ala Thr Leu Val Phe Asp Tyr Pro Thr Pro Val Ala Leu Ala Arg Tyr
        1075                1080                1085

Leu Arg Asp Glu Phe Gly Asp Thr Val Ala Thr Thr Pro Val Ala Thr
    1090                1095                1100

Ala Ala Ala Asp Ala Gly Glu Pro Ile Ala Ile Val Gly Met Ala
1105                1110                1115                1120

Cys Arg Leu Pro Gly Gly Val Thr Asp Pro Glu Gly Leu Trp Arg Leu
                1125                1130                1135

Val Arg Asp Gly Leu Glu Gly Leu Ser Pro Phe Pro Glu Asp Arg Gly
            1140                1145                1150

Trp Asp Leu Glu Asn Leu Phe Asp Asp Asp Pro Asp Arg Ser Gly Thr
```

-continued

```
                 1155                1160                1165
Thr Tyr Thr Ser Arg Gly Gly Phe Leu Asp Gly Ala Gly Leu Phe Asp
    1170                1175                1180
Ala Gly Phe Phe Gly Ile Ser Pro Arg Glu Ala Leu Ala Met Asp Pro
1185                1190                1195                1200
Gln Gln Arg Leu Leu Leu Glu Ala Ala Trp Glu Ala Leu Glu Gly Thr
                1205                1210                1215
Gly Val Asp Pro Gly Ser Leu Lys Gly Ala Asp Val Gly Val Phe Ala
    1220                1225                1230
Gly Val Ser Asn Gln Gly Tyr Gly Met Gly Ala Asp Pro Ala Glu Leu
    1235                1240                1245
Ala Gly Tyr Ala Ser Thr Ala Gly Ala Ser Ser Val Val Ser Gly Arg
    1250                1255                1260
Val Ser Tyr Val Phe Gly Phe Glu Gly Pro Ala Val Thr Ile Asp Thr
1265                1270                1275                1280
Ala Cys Ser Ser Ser Leu Val Ala Met His Leu Ala Gly Gln Ala Leu
                1285                1290                1295
Arg Gln Gly Glu Cys Ser Met Ala Leu Ala Gly Gly Val Thr Val Met
                1300                1305                1310
Gly Thr Pro Gly Thr Phe Val Glu Phe Ala Lys Gln Arg Gly Leu Ala
    1315                1320                1325
Gly Asp Gly Arg Cys Lys Ala Tyr Ala Glu Gly Ala Asp Gly Thr Gly
    1330                1335                1340
Trp Ala Glu Gly Val Gly Val Val Leu Glu Arg Leu Ser Val Ala
1345                1350                1355                1360
Arg Glu Arg Gly His Arg Val Leu Ala Val Leu Arg Gly Ser Ala Val
                1365                1370                1375
Asn Ser Asp Gly Ala Ser Asn Gly Leu Thr Ala Pro Asn Gly Pro Ser
                1380                1385                1390
Gln Gln Arg Val Ile Arg Arg Ala Leu Ala Gly Ala Gly Leu Glu Pro
                1395                1400                1405
Ser Asp Val Asp Ile Val Glu Gly His Gly Thr Gly Thr Ala Leu Gly
    1410                1415                1420
Asp Pro Ile Glu Ala Gln Ala Leu Leu Ala Thr Tyr Gly Lys Asp Arg
1425                1430                1435                1440
Asp Pro Glu Thr Pro Leu Trp Leu Gly Ser Val Lys Ser Asn Phe Gly
                1445                1450                1455
His Thr Gln Ser Ala Ala Gly Val Ala Gly Val Ile Lys Met Val Gln
                1460                1465                1470
Ala Leu Arg His Gly Val Met Pro Pro Thr Leu His Val Asp Arg Pro
    1475                1480                1485
Thr Ser Gln Val Asp Trp Ser Ala Gly Ala Val Glu Val Leu Thr Glu
    1490                1495                1500
Ala Arg Glu Trp Pro Arg Asn Gly Arg Pro Arg Arg Ala Gly Val Ser
1505                1510                1515                1520
Ser Phe Gly Ile Ser Gly Thr Asn Ala His Leu Ile Ile Glu Glu Ala
                1525                1530                1535
Pro Ala Glu Pro Gln Leu Ala Gly Pro Pro Asp Gly Gly Val Val
                1540                1545                1550
Pro Leu Val Val Ser Ala Arg Ser Pro Gly Ala Leu Ala Gly Gln Ala
    1555                1560                1565
Arg Arg Leu Ala Thr Phe Leu Gly Asp Gly Pro Leu Ser Asp Val Ala
    1570                1575                1580
```

Gly Ala Leu Thr Ser Arg Ala Leu Phe Gly Glu Arg Ala Val Val Val
1585                1590                1595                1600

Ala Asp Ser Ala Glu Glu Ala Arg Ala Gly Leu Gly Ala Leu Ala Arg
                1605                1610                1615

Gly Glu Asp Ala Pro Gly Leu Val Arg Gly Arg Val Pro Ala Ser Gly
            1620                1625                1630

Leu Pro Gly Lys Leu Val Trp Val Phe Pro Gly Gln Gly Thr Gln Trp
        1635                1640                1645

Val Gly Met Gly Arg Glu Leu Leu Glu Glu Ser Pro Val Phe Ala Glu
    1650                1655                1660

Arg Ile Ala Glu Cys Ala Ala Ala Leu Glu Pro Trp Ile Gly Trp Ser
1665                1670                1675                1680

Leu Phe Asp Val Leu Arg Gly Asp Gly Asp Leu Asp Arg Val Asp Val
                1685                1690                1695

Leu Gln Pro Ala Cys Phe Ala Val Met Val Gly Leu Ala Ala Val Trp
            1700                1705                1710

Ser Ser Ala Gly Val Val Pro Asp Ala Val Leu Gly His Ser Gln Gly
        1715                1720                1725

Glu Ile Ala Ala Ala Cys Val Ser Gly Ala Leu Ser Leu Glu Asp Ala
    1730                1735                1740

Ala Lys Val Val Ala Leu Arg Ser Gln Ala Ile Ala Ala Lys Leu Ser
1745                1750                1755                1760

Gly Arg Gly Gly Met Ala Ser Val Ala Leu Gly Glu Ala Asp Val Val
                1765                1770                1775

Ser Arg Leu Ala Asp Gly Val Glu Val Ala Ala Val Asn Gly Pro Ala
            1780                1785                1790

Ser Val Val Ile Ala Gly Asp Ala Gln Ala Leu Asp Glu Thr Leu Glu
        1795                1800                1805

Ala Leu Ser Gly Ala Gly Ile Arg Ala Arg Arg Val Ala Val Asp Tyr
    1810                1815                1820

Ala Ser His Thr Arg His Val Glu Asp Ile Glu Asp Thr Leu Ala Glu
1825                1830                1835                1840

Ala Leu Ala Gly Ile Asp Ala Arg Ala Pro Leu Val Pro Phe Leu Ser
                1845                1850                1855

Thr Leu Thr Gly Glu Trp Ile Arg Asp Glu Gly Val Val Asp Gly Gly
            1860                1865                1870

Tyr Trp Tyr
        1875

<210> SEQ ID NO 3
<211> LENGTH: 53799
<212> TYPE: DNA
<213> ORGANISM: Amycolatopsis mediterranei

<400> SEQUENCE: 3
gaattccagg ccgtcgacgg ctgcgacatc gcggtcttcc ggtggtcgca ccgcacgaag     60
atcgccgaat aagaatttcc ggatctccca cgggaaaggt ttccatgacc gacgcaatat    120
ccttcgaggt gccgtgggac cggaccgaca agttcgaccc gccgcggtg ttcgactctc     180 tgcgcgaaga acgtccgctc gcgaagatgg tttacccgga tggcacgtc ggctggatcg     240 tttccagcta cgagctggtc cgcgaggtcc tcagcgacct gcggttcagc cacagctgcg    300
aagtcggcca cttcccggtg acccaccagg gccaggtcat cccgacccac ccgctgatcc    360
ccggcatgtt catccacatg gacccgcccg agcacacgcg ctaccgcaag ctgctgaccg    420

-continued

```
gcgagttcac cgtccgccgc gccagcaggc tgatcccgcg ggccgaggcc gtggccgccg    480
agcagatcga ggtcatgcgg gccaagggcg ccccgcgga cgtggtcatg gacttcgcca    540
agccgctggt gctgcggatg ctgggcgagc tcgtcggcct gccctacgag gaacgcgacc    600
ggtacgtgcc cgcggtgacc ctcctgcacg acgccgaagc ggacccggcc gaggccgcgg    660
ccgcctacga ggtggccggg aagttcttcg acgaggtcat cgagcgccgc cggcagcggc    720
cccaggacga cctcatcagc tcgctcgtca ccgaggacct gacccaggag gagctgcgca    780
acatcgtcac cctgctgctg ttcgccgggt acgagaccac cgaggcgcg ctcgccaccg    840
gcgtcttcgc gctgctgcac cacaccgatc agctggcggc actgcgcgcg gagccggaaa    900
agctcgacgc cgcgatcgaa gagctgctgc gctacctgac cgtcaaccag taccacacct    960
accgcaccgc gctggaggac gtgaagctgg agggcgagct gatcaagaag ggcgacacgg   1020
tgacggtgtc gctgcccgcg gccaaccgcg acccggccaa gttcggctgt ccgcggagc    1080
tcgacatcga gcgggacacc tccggccacg tcgcgttcgg cttcggcatc caccagtgcc   1140
tgggccagaa cctggcgcgc atcgagctgc gggccggctt cacggcgctc ctgcgggcgt   1200
tccccgagct ccggctggcc gtcccggccg acgaggttcc gctgcggctg aagggttccg   1260
tcttctcggt gaagaagctg cccgtctcct ggtgagcgtt cttcccctcg aacacccgaa   1320
aggatctgcg gcacagtgcg caccgatctc atcaagccac ttcacgtcgc actcctggag   1380
aacgcgaccc gcttcgccgg caagccggcc ttcgccgacg accaccggac ggtcacctac   1440
ggcgacctcg aggcgcggac gcgccggctg gccgggcacc tggccggcct cggtgtccgg   1500
cacggcgacc gggtggcgat ctgcctcggc aaccgggtgt ccactgtgga gagttacttc   1560
gcgatcctgc gcgcgggtgc cgtcggcgtg ccgctcaacc ccggttcggc gacggccgag   1620
ctcgagcacc cgctgaccga cagcggcgcc acggtggtcg tcaccgacgc cgcccaggcg   1680
gcccggctcc ggctcgcgcc gcacgtcgag ctgctggtga ccggcgacga cgtcccggag   1740
ggcgcccact cctacgacga actcgccctc agcgaaccgg ccgagcccgc cgcggacgac   1800
ctcgagctcg acgagccggc gtggatgttc tacacgtcgg gcacgaccgg gcggcccaag   1860
ggcgtcgtgt ccacgcagcg caactgcctc tggtccgtcg cttcctgcta cgtgccgttc   1920
cccgggtttgt cggaccagga ccgggtgctc tggccgctcc cgctgttcca cagccttcg   1980
cacatcgcct gcgtcctgtc cgccaccgtg gtcggggcca gcgtccggat cgccgacggc   2040
agctccgccg acgacgtgat gcggctgatc gaggcggaga gctcgacctt cctgccggc    2100
gtgccgacca cctaccacca cctggtgcgg gccgcccggc agcgcggttt ctccgcgccg   2160
agcctgcgga tcgcctggc cggggcgcg gtcctcggcg ccgggctgcg aagcgagttc    2220
gaagagacct tcgggtccc gctgatcgac gcctacggca gcaccgagac ctgcggggcg    2280
atcaccatga acccgccgga cggcgcccgc gtcgagggct cgtgcggctt ggccgtgccg    2340
ggcgtcgacg tgcgggtcgt cgaccccgac accgggctcg acgtccccgc cggcgaggag    2400
ggcgaggtct gggtcagcgg gccgaacgtc atgctcggct accacaacag cccggaggcg    2460
accgccgcgg cgatgcggga cggctggttc cggaccgggg acctggcccg ccgcgacgac    2520
gccggttact tcaccatctg cggcggatc aaggaactca tcatccgcgg cggcgcgaac    2580
atccaccccg gcgaggtcga ggcggtcctg cgcacgtcg acgcgtcgc ggacgcggcg    2640
gtcggcggtg tgccgcacga cacgctcggc gaggtgccgg tcgcctacgt catccccgga    2700
ccgaccggtt tcgatcctgc ggcgttgatc gagaagtgcc gcgaacagct gtccgcctac    2760
```

-continued

```
aaggtgccgg accggatcct cgaggtcgcc cacattcccc ggaccgcgtc gggcaagatc    2820
cggcgcgggc tgctgaccga cgagcccgcg cagctgcggt acgccgcgac cgaacacgag    2880
gaacagtccc ggcacgccga cgagtccgtc gcggcggcgc tgcgcgcgcg actgtccggt    2940
ttggacgaac gcgcccagtg cgagctcctg aagacctcg tccgcaccca ggcggccgac    3000 gtgctgggc agccggtccc ggacgggcgt gcgttccgcg acctcggctt cacgtcgctg    3060
gccatcgtgg agctgcgcaa ccggctgacc gagcacaccg gctctggct gcccgccagc    3120 gccgtcttcg accaccccac gccggcggcg ctggccgccc gcgtccgggc tgagctcctc    3180
gggatcacgc aggccgtcgc ggagccggtc gtcgcggccc acccgggcga ccgatcgcg    3240 atcgtgggga tggcctgccg cctgccgggt ggcgtggcgt ccccggaaga cctgtggcgg    3300
ctggtggccg agcgcgtcga cgccgtttcg gagttccccg cgaccgcgg ctgggacctg    3360 gacagcctga tcgacccgga ccggagcgc gccgggacgt cgtacgtcgg ccagggcgga    3420
ttcctgcacg acgccggcga gttcgacgcc gggttcttcg ggatctcgcc gcgtgaggcc    3480
gtcgcgatgg acccgcagca gcggttgctg ctggagacgt cgtgggaggc cctcgaaaac    3540
gccggagtcg acccgatcgc gttgaagggc accgacaccg gcgtgttctc cggcctcatg    3600
ggccaggggt acgggtccgg cgcggtggcg ccggagctcg aaggtttcgt caccaccggg    3660
gtcgcgtcga gcgtggcctc gggccgggtg tcgtacgtgc tgggactgga aggcccggcg    3720
gtcaccgtgg acaccgcgtg ttcgtcgtcg ctggtcgcga tgcacctggc cgcgcaggcc    3780
ctgcggcagg gcgaatgctc gatggcgctc gccggcgggg tcacggtgat ggccacgccg    3840
ggctcgttcg tcgagttctc ccgccagcgg gccctggcgc ccgacgggcg ctgcaaggcc    3900
ttcgcggcgg cggccgacgg gaccggctgg tccgagggtg tcggcgtggt cgtcctcgag    3960
cggctgtccg tggcgcgcga gcggggccac cggatcctgg ccgttttgcg tggcagcgcg    4020
gtcaaccagg acgcgcgtc caacgggctc accgcgccga acggcctctc gcagcagcgg    4080
gtcatccgcc gcgcgctggc cgcggccggg ctggcaccgt ccgatgtgga cgtcgtcgag    4140
gcgcacggca ccgggaccac gctgggtgac ccgatcgagg cgcaggccct gctggcgacc    4200 tacgccagg agcggaagca gccgttgtgg ctcggttcgc tcaagtcgaa catcggccac    4260
gcgcaggcgg ccgcgggcgt tgcgggcgtc atcaagatgg tgcaggcgct gcggcacgag    4320
accttgccgc cgacgctgca tgtcgacaag ccgactcttg aggtggactg gtccgccggt    4380
gccattgaac tgctgacgga ggcccgtgcg tggccgcgca acggccgtcc gcgccgggcc    4440
ggggtgtcgt cgttcggcgt cagcgggacc aacgcgcacc tgatcctgga ggaggcgccg    4500
gccgaggagc cggtcgctgc cccggaactg ccggtggtgc ccctggtggt gtcggcgcgg    4560
agcacggagt cgctgtccgg gcaggccgag cggctggcgt ccctcctcga aggggacgtc    4620
tcgctgaccg aggtggccgg ggcgctggtg tcccgccggg cggtgctgga cgagcgggcc    4680
gtcgtcgtgg ccgttcgcg cgaggaagcc gtgaccggc tgcgggcgct gaacacggcc    4740
ggttcgggga cgccgggcaa ggtcgtgtgg gtgttcccgg ggcagggac gcagtgggcc    4800 gggatgggcc gtgagctgct ggccgagtcc ccggtgttcg ccgagcggat cgccgagtgc    4860
gcggccgcgt tggcgccgtg gatcgactgg tcgctcgtcg acgtcctgcg cggcgagggc    4920
gacctgggtc gggtcgatgt gctgcagccg gcctgtttcg cggtgatggt cgggctggct    4980
gccgtctggg agtccgtggg ggtccggccg gacgccgtcg tcgggcactc gcagggtgag    5040
atcgcggctg cctgcgtttc gggggcgttg tccctcgagg acgcggcgaa ggtggtggca    5100
ctgcgcagcc aggccatcgc ggcggaactg tccgccgcg gcgggatggc gtcggtcgcc    5160
```

-continued

```
ctgggcgagg acgacgtcgt tcgcggctg gtggacgggg tcgaggtcgc cgccgtcaac      5220
ggcccgtcgt cggtggtgat cgccggggat gcccatgccc tcgacgcgac cctggaaatc    5280
ttgtccgggg aaggcatccg ggttcggcgg gtggcggtgg actacgcctc gcacacccgg    5340
catgtcgagg acatccgcga cactcttgcc gaaaccttgg ccgggatcag tgcgcaggcg    5400
ccggctgtgc cgttctactc caccgtcacg agcgagtggg tgcgcgacgc ggggtgctg     5460
gacggcggct actggtaccg gaacctgcgc aaccaggtcc ggttcggagc ggccgcgacg    5520
gccctgctcg agcagggcca cacggtgttc gtcgaggtca gtgcgcaccc ggtgacggtc    5580
cagcccttga gcgagctcac cggggacgcg atcgggacat gcggcgtga agacggtggc     5640
ctgcggcggt tgctggcttc gatgggtgag ctgttcgtcc gcggcatcga cgtggactgg    5700
acggcgatgg tgcccgcggc cggctgggtc gacttgccga cctacgcgtt cgaacaccgg    5760
cactactggc tcgagcccgc cgagcccgct tcggccggag accgctgct gggcacagtc     5820
gtcagcactc ccggttcgga ccgactcacc gccgtggcgc agtggtcgcg ccgggcgcag    5880
ccctgggcgg tggacggcct ggtgccgaac gcggccctgg tcgaggcggc catccggctc    5940
ggcgacctgg ccggcacccc cgtcgtcggc gaactggtcg tcgacgcgcc ggtggtgctg    6000
ccgcggcgcg gcagccgcga ggtccagctg atcgtcggcg agcccggcga gcagcggcgg   6060
cgtccgatcg aggtcttttc ccgggaagcc gacgagccgt ggacgcggca cgcgcacggc    6120
acactcgctc ccgccgccgc tgcggtgcca gaaccggcgg cggcgggaga cgccaccgac    6180
gtcaccgtgg ccggcctgcg cgacgcggac cggtacggga tccaccccgc gctgctggac    6240
gccgccgtcc gcacggtcgt cggcgacgac ctgctcccgt cggtgtggac cggcgtgtcc    6300
ctgctggcct ccgggggccac ggccgtgacc gtgacgccga cggcgaccgg cctgcggctg   6360
accgacccgg ccgggcagcc cgtcctgacc gtcgaatccg tgcgcggcac gccgttcgtc    6420
gccgagcagg ggaccaccga cgcgctcttc cgcgtcgact ggccggaaat cccgctgccc    6480
accgccgaaa ccgcggactt cctgccgtac gaagccacgt cggccgaggc gaccctctcc    6540
gcgctccagg cctggctggc agaccccgcg gaaacccggc tggccgtggt caccggggac    6600
tgcaccgaac ccggcgcggc cgcgatctgg ggcctggtgc gctcggcgca gtccgaacac    6660
cccgccgga tcgtgctggc cgacctcgac gaccccgccg tgctgcccgc cgtggtggcg    6720
agcggcgaac cgcaggtgcg ggtgcgcaac ggcgtcgcct cggtgccgcg cttgacccgg    6780
gttactcccc ggcaggacgc gcggccgctc gaccccgagg gcaccgtcct gatcaccggc    6840
ggcaccggca cgctcggtgc gctgaccgcc cggcacctcg tcaccgcgca cggcgtccgg    6900
cacctggtgc tggtcagccg ccgcggtgag gctcccgagc tgcaggaaga actgaccgca    6960
ctgggggcat ccgtcgccat cgccgcctgc gacgtggcag accgggcgca gctcgaagcc    7020
gtcttgcgcg cgatcccggc cgagcacccg ctcaccgccg tgatccacac cgcggggggtc   7080
ctcgacgacg gcgtcgtcac cgagctgacc ccggaccggc tcgccaccgt gcggcggccg    7140
aaggtcgacg ccgcccggct cctggacgag ctcacccggg aggccgatct cgccgcgttc    7200
gtgctgttct cctcggcggc gggtgtgctg gcaaccccg gccaggccgg gtacgccgcc     7260
gccaacgccg agctggatgc gttggcgcgc cagcggaaca gcctcgacct gcccgcggtg    7320
tccatcgcat ggggctactg gcgacggtc agcgggatga ccgagcacct gggcgacgcc     7380
gacctgcggc gcaaccagcg gatcggcatg tccgggcttc ccgccgacga gggcatggcg    7440
ctgctggacg ccgccatcgc caccggtggc acgctggtcg cggccaagtt cgacgtcgcc    7500
```

-continued

```
gcgctgcggg cgacggcgaa ggccggcggc ccggtgccgc cgctgctgcg tggcctggcc    7560
ccgctgccgc gccgggcggc ggccaagacc gcgtcgctga ccgaacgcct cgccgggctg    7620
gccgagaccg agcaggccgc ggccctgctc gacctggtcc ggcggcacgc cgccgaggtg    7680
ctcgggcaca gcggcgccga atccgtccat tcaggacgga cgttcaagga cgccggcttc    7740
gactcgctga ccgcggtgga actgcggaac cgcctcgcgg ccgcgaccgg gctcaccctg    7800
tccccggcga tgatcttcga ctacccgaag ccccccgcgc tcgcggacca cctgcgcgcc    7860
aagctcttcg gatcggcggc gaaccggccg gccgagatcg gcaccgccgc ggccgaggag    7920
ccgatcgcga tcgtcgcgat ggcgtgccgc ttccccggtg gcgtgcacag ccccgaggac    7980
ctgtggcggc tggtcgccga cggcgccgac gccgtcaccg agttccccgc cgaccgcggc    8040
tgggacaccg accggctcta ccacgaagac cccgaccacg aaggcacgac gtacgtccgg    8100
cacggcgcct cctcgacga cgccgccggg ttcgacgccg ccttcttcgg catctcgccg    8160
aacgaggcgc tcgccatgga cccgcagcag cggctgctgc tggagacgtc ctgggagctg    8220
ttcgagcggg ccgcgatcga cccgaccacg ctggccggcc aggacatcgg cgtcttcgcc    8280
ggcgtcaaca gccacgacta cagcatgcgg atgcaccggg ccgccggtgt cgagggcttc    8340
cggctcaccg gcggttcggc cagcgtgctc tccggccgcg tcgcctacca cttcggcgtc    8400
gaaggcccgg ccgtcacggt cgacacggcc tgctcgtctt cgctggtcgc gctgcacatg    8460
gcggtgcagg ccctgcagcg cggcgagtgc tccatggcgc tcgcgggcgg cgtgatggtg    8520
atgggcacgg tcgagacgtt cgtcgagttc tcgcggcagc gcgggctggc ccccgacggc    8580
cgctgcaagg cgttcgccga cggcgcggac ggcaccggct ggtccgaggg cgtcgggctg    8640
ctcctggtgg agcggctgtc cgaggctcag cgtcgcgggc accaggtcct cgccgtggtc    8700
cgcgggtcgg cggtcaactc cgacggcgcg tcgaacggct tgacggcccc gaacggcccg    8760
tcccagcagc gcgtgatccg caaggcactg gccgccgccg gactgtccac atcggacgtc    8820
gacgcggtgg aggcgcacgg caccgggacg accctgggcg acccgatcga ggccgaggcg    8880
ctgctggcca cctacggcca gaaccggaa acgccgctgt ggctcgggtc ggtgaagtcg    8940
aacctcgggc acacgcaggc ggctgcgggt gtcgcaggcg tgatcaagat ggtcatggcc    9000
atgcgccacg cgtcctgcc ccggacgctg cacgtcgacc ggccgtcgtc ctatgtggac    9060
tggtcggccg gtgcggtcga gctgctgacc gaggcacggg actgggtgag caacggccac    9120
ccgcgccgcg cgggcgtgtc gtcgttcggc atcggcggca ccaacgcgca cgtcgtcctc    9180
gaagaggttg ccgcaccgat caccacgccg cagcctgagc cggccgagtt cctggtgccg    9240
gtgctcgtct ccgcgcggac ggcggcgggt ctgcgcggcc aggccggacg gctcgccgcg    9300
ttcctcggca ccggaccga cgtccgcgtc cccgatgccg cctacgcact ggccaccacg    9360
cgcgcccagc tcgaccaccg ggccgtcgtc ctggcctccg accgggcaca gctctgcgcg    9420
gaccttgccg cgttcggctc cggcgtcgtg accggaacgc cggttgacgg caagctggcc    9480
gtgctcttca ccggccaggg cagccagtgg gccgggatgg gccgtgaact cgccgagacg    9540
ttcccggtct tccgcgacgc cttcgaggcc gcgtgcgagg ccgtggacac gcacctgcgt    9600
gagcgtccgc tgcgcgaggt cgtgttcgac gacagcgcgc tgctcgacca gacgatgtac    9660
acccagggcg ccctgttcgc cgtggagacc gcgttgttcc ggctcttcga gtcctggggt    9720
gtgcggccgg gtctcctcgc cggtcactcg atcggcgagc tcgccgccgc gcacgtgtcc    9780
ggcgtgctgg acctgccga cgcgggcgag ctggtcgccg cgcgcggccg gctgatgcag    9840
gccctgcccg cgggcggcgc gatggtcgcc gtccaggcga ccgaggacga agtcgcgccc    9900
```

```
ctgctcgacg gcacggtctg cgtcgccgcg gtcaacggtc cggactcggt ggtgctctcc     9960
ggcaccgaag ccgccgtgct cgccgtcgcg gatgaactgg ctggtcgcgg ccgtaagacc    10020
cgacggctgg ccgtgagcca cgccttccac tcgccgctca tggaaccgat gctcgacgac    10080
ttccgcgcgg tcgccgaacg cctgacgtac cgggccggtt cgctgcccgt cgtctcgacg    10140
ctgaccgggg aactcgcggc gctcgacagc ccggactact gggtcggcca ggtgcgcaac    10200
gccgtgcggt tcagcgacgc cgtcaccgcg ctgggcgccc aaggcgcgtc gacgttcctc    10260
gagctcggcc cggtcggtgc gctcgccgcg atggcgctcg gcacgctcgg cggacccgag    10320
cagagctgcg tcgcgaccct gcgcaagaac ggcgccgagg tgcccgacgt cctcaccgcg    10380
ctcgccgaac tgcacgtccg gggcgtgggc gtcgactgga cgaccgtgct cgacgaaccg    10440
gccacggcgg tcgggaccgt cctgcccacc tacgcgttcc agcaccagcg cttctgggtc    10500
gacgtcgacg aaacagcggc cgtcagcgtc accccgccgc cggcggagcc gatcgtggac    10560
cggccggtgc aggacgtgct ggagctggtc cgggagagcg ccgcggtggt gctcgggcac    10620
cgggacgccg gcagtttcga cctcgaccgg tccttcaagg accacggctt cgactcgctc    10680
agcgcggtca agctgcgcaa ccgtctgcgc gacttcaccg gcgtggagct gcccagcacc    10740
ctgatcttcg actacccgaa cccggccgtc ctcgcggacc acctgcgggc cgaactgctc    10800
ggcgagcgcc cggccgcgcc ggccccggtg acgaggacg tctccgacga gccgatcgcg     10860
atcgtcggca tgagcacccg gctgccgggt ggcgccgaca gccccgaaga gctgtggaag    10920
ctcgtcgcgg agggacggga cgccgtgtcc ggcttccccg tcgaccgcgg ctgggacctc    10980
gacggcctct accacccgga ccccgcccac gccgggacga gctacacgcg ttcgggcggc    11040
ttcctgcacg acgcggccca gttcgacgcc gggctcttcg ggatctcacc gcgtgaggcc    11100
ctggccatgg acccgcagca gcggctgctg ctggagacgt cgtgggaagc cttggagcgc    11160
gcggggtcg acccgctgtc cgcccgcggc agcgacgtcg gcgtcttcac cgggatcgtc     11220
caccacgact acgtgacgcg gctgcgcgaa gtgcccgaag acgtccaggg ctacacgatg    11280
accggcacgg cttcgagcgt ggcgtcgggc cgggtggcgt acgtcttcgg cttcgagggc    11340
ccggcggtca ccgtggacac cgcgtgttcg tcgtcgctgg tcgcgatgca cctggcggcg    11400
caggcgctgc ggcaggggga gtgctcgatg gccctggccg gcggcgcgac cgtgatggcc    11460
agcccggacg ccttcctcga gttctcccgc cagcgcggcc tgtccgcgga cggccggtgc    11520
aaggcgtacg cggaaggcgc ggacggcacg ggctgggccg agggcgtcgg tgtcgtcgtc    11580
ctcgaacggc tttcggtggc acgcgaacgt ggccaccggg tgctggcggt cctgcgcggc    11640
agcgcggtga accaggacgg tgcttccaac ggcctgaccg ccccgaacgg gccgtcgcag    11700
cagcgggtga tccgcggcgc gctggcgagc gccgggctgg caccgtccga tgtggacgtc    11760
gtggagggcc acgggaccgg gaccgcgctg gtgaccccga tcgaggtcca ggcgctgctg    11820
gccacctacg ggcaggagcg ggaacagccg ttgtggctcg gctcgctgaa gtcgaacctc    11880
gggcacacgc aggccgcggc cggggtcgtg ggcgtgatca agatgatcat ggccatgcgc    11940
cacggcgtca tgccggccac gctgcacgtc gacgagcgca cgagccaggt cgactggtcg    12000
gcgggcgcga tcgaggtgtt gaccgaggcc cgggagtggc cgcgcaccgg acgtccgcgc    12060
cgggccgggg tgtcctcctt cggcgccagc ggcaccaacg cgcacctgat catcgaggaa    12120
ggtcccgccg aagaggccgt ggacgaagag gtgcctccg tggtgccgct ggtcgtctcc     12180
gcccgcagcg ccggttcgct ggccgggcag gccgggcgcc tggccgcggt cctcgagaac    12240
```

-continued

```
gaatcgttgg ccggggtggc cggtgccctg gtttccggcc gcgcgacgct gaacgagcgc    12300
gcggtcgtca tcgcgggctc ccgcgacgag gcccaggacg gcctgcaggc actggcccgc    12360
ggcgagaacg cgcccggcgt cgtgaccggg acggcgggca agccgggcaa ggtcgtctgg    12420
gtcttccccg gccagggctc gcagtggatg ggcatgggcc gggacctcct ggactcctcg    12480
ccggtgttcg ccgcgcggat caaggaatgc gctgcggcac tggaacagtg gaccgactgg    12540
tcgctgctgg acgtgctgcg cggcgacgcc gacctgctgg accgggtcga cgtggtgcag    12600
ccggccagct cgcgatgat ggtcgggctc gccgcggtgt ggacctcgct gggggtgacc    12660
ccggatgcgg tgctcggcca ctcccagggc gagatcgccg cggcgtgcgt gtccggcgcg    12720
ctgtcgctgg acgacgcggc gaaggtggtc gcgttgcgca gccaggcgat cgcggggggag    12780 ctggcgggcc gcggcgggat ggcgtcggtc gcactgagcg aagaggacgc agtcgcgcgg    12840
ctgacgccgt gggcgaaccg ggtcgaggtg gccgcggtca acagcccgtc ctcggtcgtc    12900
atcgcgggag acgcgcaggc cctcgacgaa gccctcgaag ccctggccgg cgacggtgtc    12960
cgggtccggc gggtcgcggt ggactacgcc tcccacaccc ggcacgtcga ggcgatcgcc    13020
gaaaccctgg ccaagacctt ggccgggatc gacgcgcggg ttccggcgat tccgttctat    13080
tccaccgtcc tgggcacgtg gatcgagcag gccgtcgtcg acgcgggcta ctggtaccgg    13140
aacctgcggc agcaggtgcg gttcggcccc tcggtggcgg acctgccgg gctggggcac    13200 acggtgttcg tggagatcag cgcccacccg gtgctggtcc agccgctgag cgagatcagc    13260
gacgacgcgg tggtgaccgg gtcgctgcgg cgggacgacg ggggactgcg gcgcctgctg    13320
gcgtcggcgg ccgaactgta cgtccggggc gtggccgtgg actggacggc ggccgtgccc    13380
gcggccggct gggtggacct gccgacgtac gccttcgacc gccgccactt ctggctgcac    13440
gaagccgaga ccgccgaagc cgccgagggc atggacggcg agttctggac ggcgatcgaa    13500
cagtccgatg tggacagctt ggccgagctg ctcgagctgg tgccgagca gcgcggggcg    13560 ctcagcaccg tcgtgcccgt gctggcgcag tggcgggacc ggcgccgcga gcgctcgacc    13620
gcggagaagc tgcgctacca ggtcacctgg cagcccctgg agcgcgaagc cgccggcgtg    13680
ccgggcgggc gctggctggc cgtcgtcccg gccggcacca ccgacgcgct cctgaaggag    13740
ctgaccggcc agggactcga catcgtccgg ctggagatcg aggaagcttc gcgggcacag    13800
ctcgccgagc agctgcggaa cgtcctggcg gagcacgacc tcaccggcgt gctgtcgctg    13860
ctcgctctcg acggcggccc cgcggacgcg gccgagatca ccgcgtcgac gctcgcgctg    13920
gtccaggccc tgggcgacac caccacgtcc gcgccgctgt ggtgcctcac ttccggcgcg    13980
gtgaacatcg gcatccagga cgccgtgacc gcaccggccc aggcggccgt gtggggggctc    14040 ggccgggccg tcgcgctgga gcgcctcgac cggtggggcg gcctggtcga cttgcccgcc    14100
gcgatcgacg cccgcacggc tcaggccctg ctcggcgtcc tgaacggcgc cgccggggaa    14160
gaccagctcg cggtccggcg ctcgggcgtc taccgcaggc ggctggtccg caagcccgtg    14220
ccggagtccg cgacgagccg gtgggaaccc cgcggcacgg tcctggtgac cggtggggcc    14280
gaaggactcg gccggcacgc ctcggtctgg ctcgcgcagt ccggcgccga acggctcatc    14340
gtcaccggca ccgacggcgt cgacgaactg acggccgagc tggccgagtt cggcaccacg    14400
gtcgagttct cgcgccgacac cgaccgggac gcgatcgcgc agctggtggc ggactcggag    14460
gtcaccgccg tggtgcacgc cgcggacatc gcgcagacca gctccgtcga cgacaccggc    14520
gtggccgacc tcgacgaggt gttcgccgcg aaggtgacca ccgcggtgtg gctgaccag    14580 ctgttcgagg acacccccgct cgacgcgttc gtcgtgttct cctcgatcgc cggcatctgg    14640
```

-continued

```
ggcggtggcg ggcagggccc ggcgggtgcg gcgaacgccg tcctcgacgc cctggtcgaa   14700
tggcgccggg cccgcggcct caaggcgacg tcgatcgcct ggggcgcgct cgaccagatc   14760
ggcatcggca tggacgaggc cgccctcgcc cagctgcgcc gccgcggtgt catcccgatg   14820
gcgccgccgc tggcggtcac cgcgatggtg caggcggtcg ccggcaacga aaggccgtg    14880 gcggtggcca acatggactg ggccgccttc atcccggcgt tcacctcggt ccggcccagc   14940
ccgctgttcg ccgatctgcc cgaggcgaag gccatcctcc gggcggcgca ggacgacggc   15000
gaagacggcg acaccgcgtc gtcgctcgcg gactccctgc gcgcggtccc cgacgccgag   15060
cagaaccgca tcctgctgaa gctggtccgc ggccacgctt cgacggtgct cggccacagc   15120
ggcgccgaag gcatcggccc gcgccaggcg ttccaggagg tcggcttcga ctcgctggcc   15180
gcggtcaacc tccgcaacag cctgcacgcg gccaccgggc tgcggctgcc cgcgacgctg   15240
atcttcgact accccacccc ggaggcgctg gtcggctacc tgcgcgtcga actcctgcgg   15300
gaggccgacg acggcctgga cgggcgggaa gacgacctcc ggcgagtcct cgcggccgtg   15360
ccgttcgccc ggttcaagga ggcgggcgtg ctggacacgc tgctcggcct cgccgacacc   15420
ggcaccgaac cgggcacgga cgccgagacc accgaagcgg ccccggccgc cgacgacgca   15480
gaactgatcg acgcactgga catctccggt ctcgtgcaac gagccctcgg gcagacgagc   15540
tgaccgccga tggcgaacca atcgtggagg aagaacatgt ccgcgccgaa cgagcagatc   15600
gttgacgcac tgcgcgcgtc gctgaaggag aacgtccggc ttcagcagga aacagcgcg    15660 ctcgccgcgg ccgccgcgga gcccgtcgcg atcgtctcca tggcctgccg ctacgcgggc   15720
gggatccgcg gcccggagga cttctggcgg gtggtgtcgg aaggcgccga cgtctacacc   15780
ggcttccccg aggaccgcgg ctgggacgtc gaaggcctct accacccgga ccccgacaac   15840
cccggcacga cgtacgtgcg ggagggcgcc ttcctgcagg acgcggccca gttcgacgcc   15900
gggttcttcg gcatctcgcc gcgcgaggcg ctggccatgg accccagca gcggcagctc    15960 ctggaggtgt cctgggagac cttggaacgg gccggcatcg accgcattc ggtgcggggc    16020 agcgacatcg gcgtctacgc cggggtcgtg caccaggact acgcccccga cctcagcggg   16080
ttcgaaggct tcatgagcct ggagcgcgcc ctgggcaccg cgggcggtgt cgcctccggc   16140
cgggtcgcct acacgctcgg gctcgaaggc cccgccgtca ccgtcgacac gatgtgctcg   16200
tcgtcgctgg tggcgattca ccttgccgcg caagctcttc gccgtggtga gtgctcgatg   16260
gccctcgcgg gcggctcgac cgtgatggcg acccgggcg gttcgtcgg cttcgcgcgt     16320 cagcgggcgt tggccttcga cgggcgctgc aagtcctacg ccgcggccgc cgacggttcc   16380
ggctgggccg agggcgtcgg cgtgctgctg ctggagcggc tgtcggtggc gcgcgagcgc   16440
gggcaccagg tgctggccgt catccgcggc agcgcggtca accaggacgg cgcttccaac   16500
ggcctgaccg cgcccaacgg cccggcgcag cagcgggtca tccgcaaggc actggcgagc   16560
gccgggctga caccgtccga tgtggacacc gtggagggcc acggcaccgg caccgtcctc   16620
ggcgacccga tcgaggtcca ggcgctgctg gccacctacg ccagggccg cgacccgcag    16680 caaccgctgt ggctgggctc ggtcaagtcc gtcgtcgggc acacgcaggc ggcatccggt   16740
gtggccggcg tgatcaagat ggtccagtcg ctgcggcacg gcagctccc ggcgaccag     16800 cacgtcgacg cgcccacgcc gcaagtggac tggtcggccg gagcgatcga gctgctggcc   16860
gagggccggg agtggccgcg caacggccac ccgcgccggg gcggcatctc gtcgttcggg   16920
gccagcggca cgaacgcgca catgatcctc gaagaagcgc ccgaggacga gccggtgacc   16980
```

```
gaagcgccgg cgcccacggg tgtcgtaccg ctggtggtgt cggcggcgac cgctgcttcc    17040
ctggccgccc aggccggtcg gctggcggag gtcggcgacg tctccctggc ggatgtcgcc    17100
gggacgctgg tgtccggccg cgcgatgctc agcgagcgcg cggtcgtcgt ggccggctcc    17160
cacgaagaag ccgtgaccgg gctgcgggcg ctggcccgcg gcgagagcgc gcccggcctg    17220 cttttccggcc gcggctcggg ggtcccgggc aaggtcgtct gggtgttccc cggccagggc    17280
acgcagtggg ccggcatggg ccgcgagctg ctggactcct cggaggtgtt cgccgcgcgg    17340
atcgccgagt gcgagaccgc gctcgggcgg tgggtcgact ggtcgctgac cgacgtgctg    17400
cgcggcgagg ccgacctgct ggaccgggtc gacgtggtgc aaccggcgag cttcgccgtg    17460
atggtcgggc ttgccgccgt ctgggcctcc ctcggcgtcg agcccgaggc cgtggtgggc    17520
cactcgcagg gcgagatcgc ggccgcatgc gtgtccgggg cactgtccct ggaggacgcg    17580
gcgaaggtgg tggcgttgcg cagccaggcg atcgccgcct cgctggccgg ccggggcggc    17640
atggcgtcgg tcgcgttgag cgaagaagac gcgaccgcgc ggctcgagcc gtgggcgggc    17700
cgcgtggagg tcgccgccgt caacgggccg acgtccgtgg tgatcgccgg ggacgccgag    17760
gcgctggacg aagccctcga cgcgctcgac gaccaaggcg tccggatccg gcgggtggcg    17820
gtggactacg cctcccacac ccggcacgtc gaagccgcgc gcgacgcact ggccgagatg    17880
ctgggcggga tccgcgcgca ggcgccggaa gtgccgttct actcgaccgt gaccggcggc    17940
tgggtcgaag acgccggcgt gctcgacggc ggctactggt accggaacct ccgccgtcag    18000
gtgcggttcg gccggcggt ggccgagctg atcgagcagg gccaccgggt gttcgtcgag    18060
gtcagcgcgc atcccgtgct ggttcagccg atcaacgaac tcgtcgacga caccgaagcc    18120
gtggtcaccg ggacgctgcg gcgcgaggac ggcggcctcc ggcgcctgct ggcctcggcg    18180
gccgagctct tcgtccgcgg cgtgaccgtg gactggtccg gtgtgctgcc accgtcccgc    18240
cgggtcgagc tgccgacgta cgccttcgac caccagcact actggctgca gatgggcggg    18300
tcggccaccg acgccgtgtc gctgggcctg gccggcgccg accaccegct gctgggcgcg    18360 gtcgtcccgc tgccgcagtc cgacgggctc gtcttcacct cgcggctgtc gctgaagtcg    18420
cacccgtggc tggccgggca cgcgatcggc ggggtcgtgc tcattccggg cacggtgtac    18480
gtcgacctcg cgctgcgcgc cggcgacgag ctcggcttcg cgtcctgga agagctcgtg    18540 atcgaggcac cgctggtgct gggcgagcgc ggcggcgttc gcgtgcaggt cgccgtgagc    18600
gggccgaacg agaccggctc gcgtgcggtg gacgtcttct ccatgcggga agacggcgac    18660
gaatggaccc ggcacgcgac cggtctcctc ggggcgtcga cgtcccggga accgagccgc    18720
ttcgacttcg ccgcctggcc gccggccggg gcggagccga tcgacgtcga aaacttctac    18780
accgacctca ccgagcgcgg gtacgcctac agcggcgcct tccagggcat gcgggcggtc    18840
tggcggcgcg gtgacgaggt cttcgccgag gtcgcgctgc ctgacgacca ccgcgaggac    18900
gccggcaagt tcggcctcca ccccgccctc ctcgacgccc tctgcacac gaacgccttc    18960 gcgaacccgg acgacgaccg cagtgtgctg ccgttcgcgt ggaacggcct ggtcctgcac    19020
gccgtgggcg cgtcggcgct gcgggtgcgg gtggcgccgg gcgtccggac gcgctgacg    19080 ttccaggccg ccgacgagac cggtggcctg gtcgtcacca tggattcgct ggtgtcccgc    19140
gaggtgtcgg ccgcgcagct ggagacggcg cgggcgaag agcgcgactc gctgttccag    19200
gtggactgga tcgaggtccc cgcgaccgag accgcggcca ccgagcacgc cgaggtgctc    19260
gaagccttcg gcgaggcagc gcccctcgag ctgaccagcc gggtgctgga ggccgtgcag    19320
tcctggctcg ccgacgcggc cgacgaagca cggttggtcg tggtgacccg tggcgccgtg    19380
```

```
cgcgaggtga cggacccggc cggtgccgcc gtgtggggtt tggtgcgagc cgcccaggcg   19440
gagaacccgg gccggatcat cctcgtcgac accgacggcg acgtcccgct gggtgcggtg   19500
ctggccagtg gtgagccgca gctcgccgtg cgcggcaacg ctttctccgt cccgcgcctc   19560
gcccgggcca ccggcgaggt gccggaggcc cccgcggtgt tcagtccgga agggacggtc   19620
ctgctcaccg gcggcaccgg ctcgctgggc ggtctggtgg ccaagcacct ggttgcccgg   19680
cacggcgtcc ggcggctggt gctcgccagc cgccgaggcg tggccgcgga agacctcgtc   19740
accgagctga ccgagcaggg cgcgacggtg tccgtggtgg cttgcgacgt ctccgaccgc   19800
gaccaggtgg ccgcgttgct ggccgaacac cgcccgaccg gcatcgtgca cctggccggc   19860
ctgctggacg acggcgtcat cggagccctg aaccgggagc ggctggccgg ggtgttcgcg   19920
cccaaggtcg atgccgtcca gcacctcgac gaactgaccc gcgacctcgg cctcgacgcg   19980
ttcgtcgtgt tctcgtccgc agccgcgctc atgggctccg ccggccaggg caactacgcg   20040
gccgccaacg ccttcctcga cggcttgatg gccgggcgcc gcgcggcggg cctgccaggc   20100
gtgtccctgg cgtggggcct gtgggagcag gcggacggcc tgaccgcgaa cctcagcgcc   20160
accgaccagg cccggatgag ccgcggcggc gtgctgccga tgacaccggc cgaggccctg   20220
gacatcttcg acatcggcct ggccgccgag caggccctgc tggtcccgat caagctcgac   20280
ctgcggacgc tgcgcggcca ggccaccgcc ggcggcgagg tgccgcacct gctgcgcggg   20340
ctggtccgcg cgagccgccg cgtgaccgcc acggctgccg cgagtggcgg cggtggcctg   20400
gtccacaagc tcgccgggcg gccagccgaa gagcaggaag ccgtgctgct gggcatcgtc   20460
caggcggagg cggccgcggt gctcggcttc aacgcccccg agctggccca gggcaccccg   20520
gggttcagcg acctcggctt cgactcgctg accgcgtcg agctgcggaa ccggctgagc   20580
gcggcgaccg gcgtcaaatt gcccgccacg ctcgtcttcg actacccgac gccggtcgcg   20640
ctcgcccgcc acctgcgcga agagctgggc gagacggtgg cgggtgcgcc ggccacgccg   20700
gtgacgaccg tcgccgacgc gggcgagccg atcgccatcg tcggcatggc gtgccgcctg   20760
ccgggcggcg tgatgagccc cgacgacctc tggcggatgg tcgccgaggg ccgcgatggg   20820
atgtcgccgt tccccggaga ccgcggctgg gacctggacg gcctgttcga ctcggacccc   20880
gagcgcccgg gcaccgccta catccgccaa ggcggcttcc tgcacgaggc cgcgctgttc   20940
gacccgggct tcttcgggat ctcgccgcgc gaagccctgg ccatggaccc gcagcagcgg   21000
ctgctgctcg aagcctcctg ggaagccctg gagcgcgcgg gcatcgaccc gaccaaggcc   21060
cgcggtgacg ccgtcggcgt cttctccggc gtctccatcc acgactacct cgagtccctg   21120
agcaacatgc ccgccgagct cgaaggcttc gtcaccacgg ccacggcggg cagcgtcgcc   21180
tcgggccggg tgtcctacac cttcgggttc gagggcccgg cggtcacggt ggacacggcg   21240
tgctcgtcgt cgctggtcgc gatccacctg gccgcacagg cactgcggca gggcgagtgc   21300
acgatggccc tggccggcgg tgtcgccgtg atgggctcgc cgatcggtgt catcggcatg   21360
tcgcggcagc gcggcatggc cgaggacggc cgggtcaagg cgttcgccga cggcgcggac   21420
ggcaccgtcc tgtccgaagg cgtcggcatc gtcgtcctcg aacggctttc ggtggcccgc   21480
gaacgcgggc accgggtgct cgccgtgctc cgcggcagcg cggtcaacca ggacggcgct   21540
tcgaacggcc tgaccgcgcc caacgggccg tcgcagcagc gggtgatccg cagcgcgctg   21600 gccgggccg gactgcaacc gtccgaagtg gacgtcgtcg aagcgcacgg caccgggacc   21660
gcgctgggcg aaccgatcga agcccaggcc ctgctggcca cctacggcaa gagccgcgag   21720
```

```
acgccgttgt ggctcgggtc gctgaagtcg aacatcggcc acacccaggc ggccgcgggc    21780
gtggcggccg tgatcaagat ggtccaggcg ctgcggcagg acaccctgcc gccgaccctc    21840
cacgtgcagg aacccaccaa gcaggtggac tggtccgcgg gtgcggtcga gctgctgacc    21900
gaaggccggg agtgggcccg caacggccac ccgcgccggg ccggtgtctc gtcgttcggc    21960
atcagcggca ccaacgcgca cctcatcctg gaagaggcgc ccgccgacga caccgccgag    22020
gcggacgtgc ccgacgccgt ggtgcccgtg gtgatctccg cgcgcagcac cggatccctg    22080
gcgggccagg ccggacgcct ggcggcgttc ctcgacggag acgtcccgct gacccgcgtg    22140
gcgggtgccc tgctgtcgac ccgggcgacg ctgaccgacc gggccgtcgt cgtggcgggc    22200
tcggccgagg aggcccgggc ggggctgacc gcgctggccc gcggcgagag cgcgagcggg    22260
cttgtgaccg gtaccgcagg gatgccgggc aagacggtct gggtgttccc cggccagggg    22320
acgcagtggg cgggcatggg ccgggagctc ctcgaagcgt ccccggtgtt cgccgagcgc    22380
attgaggaat gcgcggccgc gctgcagccg tggatcgact ggtcgctgct ggacgtcctc    22440
cgtggcgaag gtgagctgga tcgggtcgac gtgctgcagc cggcgtgttt cgcggtgatg    22500
gtggggctgg ccgccgtctg ggcctcggtc ggcgtcgtgc cggacgcggt cctgggccac    22560
tcccagggcg agattgccgc cgcctgcgtg tcgggtgcac tgtccctcga ggacgcagcc    22620
aaggtcgtcg cgctgcgcag ccaggcgatc gcggcggagc tgtcgggccg cggggggcatg    22680 gcgtcgatcc agctgagcca cgacgaggtg gctgcccggc tcgcgccgtg ggcgggccgc    22740
gtcgagatcc ccgccgtcaa cggtccggcc tcggtcgtga tcgccggtga cgccgaagcg    22800
ctcaccgagg ccgtcgaagt cctcggcggt cggcgggtgg cggtggacta cgcgtcccac    22860
acgcggcacg tcgaggacat ccaggacacc ctcgccgaga ctctggccgg gatcgacgcg    22920
caggcccccg tggtgcccct tctactccacg gtcgccggcg agtggatcac cgatgccggg    22980
gtcgtcgacg gcgggtactg gtaccggaac ctgcgcaacc aggtcggctt cggcccggcc    23040
gtggccgagc tgatcgagca ggggcacggg gtgttcgtcg aggtcagtgc gcatccggtg    23100
ctggtgcagc cgatcagcga gctcaccgat gcggtcgtca ccgggacgtt gcggcgcgac    23160
gacggtgggg tgcggcggct gctgacctcg atggccgaac tgttcgtccg cggtgtcccg    23220
gtcgactggg ccacgatggc gccgcccgcg cgcgtcgagc tgccgaccta cgccttcgac    23280
caccagcact tctggctcag cccgcccgcc gtggcggacg cgcccgcgct cggcctggcc    23340
ggcgccgacc acccgctgct gggggcggtt ctcccgctgc cgcagtccga cggcctggtg    23400
ttcacctcgc gcctgtcggt gcggacgcat ccgtggctgg ccgacggcgt ccccgccgcc    23460
gccttggtgg agctggccgt gcgggccggt gacgaagccg gttgccccggt cctcgccgac    23520 ctgaccgtcg aaaagctgct ggtgctgccg gagagcggtg gcctgcgcgt ccaggtgatc    23580
gtgagcggcg agcgcacggt cgaggtgtat tcgcagctcg aaggcgccga agactggatc    23640
cggaacgcca ccgggcacct gtccgccacg gctccggcgc acgaggcctt cgacttcacc    23700
gcctggccgc ccgccggagc ccagcaggtc gacggcctct ggcggcgcgg cgacgagatc    23760
ttcgccgagg tcgccctgcc ggaggagctg acgccggccg cgttcggcat ccaccccttc    23820
ctgctggacg cggccgtgca gccggtcctc gcggacgacg agcagccggc ggagtggcgc    23880
agcctggtcc tgcacgccgc gggtgcctcg gcgctgcgcg tgcggctggt gcccggcggt    23940
gccctccaag cggcggacga aaccggcggg ctggtcctca cggcggattc ggtggcaggc    24000
cgggaactct cggccgggaa gacccgcgcc ggatcgctgt accgggtcga ctggaccgaa    24060
gtgtccattg cagacagtgc ggtgccggcc aacatcgagg tcgtcgaagc cttcggtgaa    24120
```

```
gagcccctgg aactgaccgg ccgggtcctg gaggctgtgc agacctggct cgtcaccgcg    24180
gccgacgatg cgcggctggt cgtggtgacc cgcggcgccg tgcgcgaggt gaccgacccc    24240
gccggtgcgg ccgtgtgggg cctggtccga gccgcgcagg cggagaaccc cggtcgcatc    24300
ttcctgatcg acaccgacgg cgagatcccg gccctgaccg gtgacgagcc cgagatcgcg    24360
gtgcgcggcg ggaagttctt cgtgcccgc atcactcgcg cggagccgag cggggccgcc    24420
gtgttccgcc cggacgggac agtgctgatc tcgggcgcgg gtgcgctcgg tggcctggtg    24480
gcccggcgtc tcgtcgaacg ccacggcgtg cggaagctcg tgctggcgtc ccggcgcggc    24540
cgagacgccg acggcgtggc ggacctggtc gccgacctgg ccgcggacgt gtccgtggtg    24600
gcttgcgacg tctccgatcg cgcccaggtg cggccctgc tcgacgagca ccggccgacc    24660
gccgtcgtgc acaccgccgg cgtcatcgac gcgggcgtga tcgagacgct ggaccgggac    24720
cggctggcca cggtgttcgc gccgaaggtc gacgccgtgc ggcacctcga cgagctgacc    24780
cgcgaccgcg acctcgacgc cttcgtcgtc tactcctcgg tctcggccgt gttcatgggc    24840
gcgggcagcg gcagttacgc cgcggcgaac gccttcctgg acggcctgat ggcgaaccgc    24900
cgggcggcgg gcctgccggg cctgtcgctg gcgtggggcc tgtgggacca gagcaccggt    24960
atggccgccg gcaccgacga ggccacccgg gcgcggatga ccgccgcgg tggcctgcag    25020 atcatgacgc aggccgaggg catggacctg ttcgacgccg cgctgtcgtc ggccgagtcg    25080
ctgctggtgc ccgccaagct cgacctgcgt ggggtgcgcg ccgacgccgc cgcgggcggg    25140
gtcgtgccgc acatgctgcg tggcctggtc cgcgcgggcc gggcgcaggc ccgcgcggcg    25200
tccactgtgg acaacgggct ggccggacgg ctggccgggc tcgccccggc ggaccagctc    25260
acgctgctcc tggacctggt ccgggcgcag gtcgcggccg tgctcgggca cgccgacgcg    25320
agcgccgtcc gcgtcgacac ggccttcaag gacgccggct tcgactcgct gaccgcggtc    25380
gagctgcgca accgcatgcg gaccgccacc ggcctgaagc tgcccgcgac gctcgtcttc    25440
gactacccga accccaggc gctcgcccgg cacctgcgcg acgaactcgg tggtgcggcc    25500
cagacgccgg tgaccacagc ggccgcgaag gccgacctcg acgagccgat cgccatcgtc    25560
gggatggcgt gccgcttgcc gggcggggtc gccgggcccg aggacctctg gcggctggtc    25620
gccgagggcc gggacgcggt gtcgagcttc ccgaccgacc gcggctggga caccgacagc    25680
ctgtacgacc ccgatccggc ccgcccgggc aagacctaca cccggcacgg cggcttcctg    25740
cacgaagccg ggctcttcga cgcgggcttc ttcgggatct cgccacgcga ggccgtcgcc    25800
atggacccgc agcagcggct gctgctggag gcctcctggg aggccatgga agacgccggg    25860
gtcgacccac tttcgctgaa gggcaacgac gtcggcgtgt tcaccggcat gttcggccag    25920
ggttacgtcg ctcccgggga cagcgtcgtc acgccggagc tggagggttt cgcgggcacg    25980
ggcgggtcgt cgagtgtcgc gtccggccgc gtgtcgtacg tgttcgggtt cgaaggcccg    26040
gccgtgacga tcgactcggc gtgctcgtcc tcgctggtcg cgatgcacct cgccgcgcag    26100
tcgctgcggc agggcgagtg ctcgatggcc ttggccggcg gcgcgacggt gatggcgaac    26160
cccggcgcat tcgtggagtt ctcgcggcag cggggcctcg ccgtcgacgg tcgctgcaag    26220
gcgttcgccg ccgcgccga cggcaccggc tgggccgagg cgtcggtgt ggtcatcctc    26280 gagcggctgt cggtggcgcg ggaacgcggc caccggatcc tggccgtgct cgcgggcagc    26340
gcggtcaacc aggacggcgc ctcgaacggc ctgaccgcgc cgaacgggcc gtcgcagcag    26400
cgggtgatcc gccgggcgct ggtgagcgcc gggctggcac cgtccgatgt ggacgtcgtc    26460
```

```
gaggcgcacg gcaccgggac cacgctgggt gacccgatcg aggcgcaagc tctgctggct   26520
acctacggca aggaccgcga gtcgccgctg tggctcggct cgctgaagtc gaacatcggc   26580
cacgcgcagg ccgccgcggg ggtcgccggc gtcatcaaga tggtccaggc gctccggcac   26640
gaagtcctgc cgccgacgct gcacgtcgac cggcctaccc ccgaggtcga ctggtcggcc   26700
ggtgccgtcg aactgctgac ggaagcccgc gagtggccgc gcaacgggcg cccgcgccgg   26760
gccggggtct ccgcgttcgg cgtcagcggc acgaacgcgc acctgatcct ggaggaggcg   26820
cccgccgaag agccggtgcc cacacccgag gttcccctgg tgccggtcgt ggtctccgcg   26880
cggagcaggg cgtccctggc cggtcaggcc ggtcgcctcg ccggattcgt ggcgggtgac   26940
gcgtccttgg ccggtgtggc ccgggcgctg gtgacgaacc gggccgcgct gaccgagcgc   27000
gcggtcatgg tcgtgggctc tcgcgaagaa gccgtgacga acctggaagc gctggcccgc   27060
ggcgaagacc cggccgcggt ggtcaccggc cgggcgggtt cgccgggcaa gctcgtctgg   27120
gtcttccccg gccagggctc gcagtggatc gggatgggcc gggaactcct ggactcttcg   27180
ccggtcttcg ccgagcgggt cgccgaatgc gcggccgccc tggaaccgtg gatcgattgg   27240
tcactgctcg acgtgctgcg cggggagtcc gacctgctgg accgggtcga cgtcgtgcag   27300
cccgccagct tcgcgatgat ggtcggcctg gccgcggtgt ggcagtcggt gggtgtccgc   27360
ccggatgccg tcgtcggcca ctcgcagggc gagatcgccg ccgcctgcgt ctcgggcgcg   27420
ctgtcgctgc aggacgccgc gaaggtggtt gccttgcgca gccaggcgat cgccacccgg   27480
ctggccgggc gcggcggcat ggcttccgtg gcgttgagcg aagaagacgc gaccgcgtgg   27540
ctggcgccgt gggccgaccg ggtccaggtg gccgcggtca acagccctgc ctccgtggtg   27600
atcgccgggg aagcccaggc cctcgacgag gtcgtcgacg cgttgtccgg tcaggaagtc   27660
cgcgtccggc gggtggccgt ggactacggg tcccacacca accaggtcga agccatcgag   27720
gatctgctgg ccgagacctt ggccggcatc gaggcgcagg ccccgaaggt gcccttctac   27780
tcgaccctga tcggtgactg gatccgtgac gccgggatcg tcgacggcgg ctactggtac   27840
cggaacctgc gcaaccaggt cgggttcggt ccggccgtcg cggagctcgt tcgccagggc   27900
cacggggtgt tcgtcgaggt cagcgcgcac ccggtgctgg tccagccgct cagtgaactc   27960
agcgacgacg cggtggtgac cgggtcgctg cggcgcgaag acggtggcct gcgccgcctg   28020
ctgacgtcga tggccgagct gtacgtgcag ggtgtcccgc tcgactggac cgcggtcctg   28080
ccgcggaccg gccgggtcga cctgccgaag tacgccttcg accaccggca ctactggctg   28140
cggcccgccg agtccgcgac cgacgcggct tcgctgggcc aggcggcggc cgaccacccg   28200
ctgctgggcg cggtcgtcga gctgccgcag tccgacggcc tggtgttcac ctcgcggctg   28260
tccgtgcgga cgcaccccgtg gctggccgac cacgcggtcg gtggcgtggt catcctcccc   28320
ggctccgggc tggccgaact ggccgtccgg gccggcgacg aagccgggtg caccgccctc   28380
gacgagctga tcatcgaagc tccgctggtc gtgcccgccc aaggcgcggt ccgcgtccag   28440
gtcgcgttga gcggcccgga cgagaccggc tcgcgcacgg tggacctcta ctcccagcgc   28500
gacggcggcg cggggacgtg gacgcggcac gccaccggcg tgctgtcgac ggcccccgct   28560
caggaacccg agttcgactt ccacgcctgg ccgcccgcgg atgccgagcg gatcgacgtc   28620
gagaccttct acaccgacct ggccgagcgt ggttacggct acgggccggc gttccagggg   28680
ctgcaagcgg tgtggcggcg tgacggcgac gtcttcgccg aggtcgccct gcccgaggac   28740
ctgcgcaagg acgcggggccg gttcggcgtc caccccgcgc tgctcgacgc ggcgctgcag   28800
gccgccacgg ccgtgggcgg cgacgagccc ggtcagccgg tgctggcgtt cgcgtggaac   28860
```

```
ggcctggtcc tgcacgccgc gggcgcgtcg gccctgcggg tccggctcgc gccgagcggc   28920
ccggacacgc tgtccgtggc agccgccgac gaaaccggcg gcttggtcct gaccatggaa   28980
tcgctggtct cccggccggt ttcggccgag cagctcggcg ccgcggccga cgcgggccac   29040
gacgcgatgt tccgcgtcga ctggaccgag ctgcctgccg tgccccgcgc ggaactgccg   29100
ccgtgggtgc ggatcgacac cgccgacgac gtcgcggcct tggcggagaa ggcggacgca   29160
ccaccggtgg tggtctggga agccgccggg ggagacccgg ccctggccgt gagttcccgg   29220
gtgctcgaga tcatgcaggc ctggctggcc gcgcccgcgt tcgaggaggc ccggctggtc   29280
gtgacgaccc gcggcgcggt acccgccggc ggtgaccaca cactgaccga cccggccgcg   29340
gccgcggtgt ggggcctggt ccggtccgcg caggcggaac acccggaccg ggtcgtcctg   29400
ctggacaccg acggcgaagt tccgctgggc gcggtgctgg cctccggtga gccgcagctc   29460
gcggtgcgcg gaacgacgtt cttcgtgccc cggctggccc gcgccacccg gctctcggac   29520
gcgcctcctg cgttcgaccc ggacgggacc gtgctggtct cgggcgccgg atcgctgggc   29580
accttggtgg cccggcacct ggtcacccgg cacggcgtgc gccgggtggt gctggccagc   29640
cggcagggcc gggacgccga gggcgcccag gacctgatca ccgagctcac cggcgaaggc   29700
gcggacgtgt ccttcgtggc ctgtgacgtc tccgatcgcg accaggtggc cgcgctgctc   29760
gcgggcctcc cggacctgac cggggtggtg cacaccgccg cgtcttcga ggacggcgtg   29820 atcgaggcgc tgacgcccga ccagctcgcg aacgtgtacg cggccaaggt cacggccgcg   29880
atgcacctca cgagctcac ccgcgaccgg atctcggcg cgttcgtcgt gttctcctcc   29940
gtcgcggggg tgatgggtgg tggcggtcaa ggcccgtacg cggcggcgaa cgccttcctg   30000
gacgcggcga tggcgagtcg tcaggccgcg ggcctgccgg gcctgtccct ggcgtggggc   30060
ctctgggaac gcagcagcgg catggccgcc cacctcagcg aggtcgacca cgcgcgggcg   30120
agccgcaacg tgtcctgga actgaccggg gccgagggcc tggcgctgtt cgacctcggg   30180
ctgcggatgg ccgagtcgct gctcgtgccg atcaagctcg acctcgccgc gatgcgggcg   30240
agcacggtcc cggtcctgtt ccgcggcctg gtccggccga gccggaccca ggcgcgcacg   30300
gcgtccactg tggaccgggg gctggccggg cggctcgccg gctgccggt ggccgagcgg   30360 gcggcggtgc tggtcgacct ggtgcgcggg caggtcgcgg tcgtgctcgg ctacgacggg   30420
ccggaggccg tccgcccgga cacggcgttc aaggacaccg ggttcgactc gctgacgtcg   30480
gtggaactgc gcaaccggct gcgcgaggcg accgggctca agctccccgc cacgctcgtc   30540
ttcgactacc cgaaccccctt ggcggtggcg cgctacctgg gcgcgcggct ggtcccggac   30600
gggaccgcga acggcaacgg gaacgggaat gggcacagcg aagacgaccg gctgcggcac   30660
gcgctggcgg ccatcgcggc cgaggacgcg ggcgaggagc ggtcgatcgc cgacctgggc   30720
gtcgacgacc tcgtgcaact ggctttcggc gacgagtgat tggggcaagt ggtgagtgcg   30780
tcgtatgaaa aggtcgtcga ggcgctgcgg aagtcgctcg aagaggtcgg cacgctgaag   30840
aagcggaacc ggcagctcgc cgacgcggcc ggcgagccga tcgccatcgt cggcatggcc   30900
tgccggctgc ccggtggcgt caccgggccc ggtgacctct ggcggctggt ggccgagggc   30960
ggcgacgccg tctcgggggtt ccccaccgac cgctgctggg acctggacac cctgttcgac   31020
ccggatcccg accacgcggg gacgtcgtac accgaccagg gcggcttcct ccacgacgcg   31080
gccctgttcg acccgggctt cttcgggatt tcgccgcgcg aggcgctggc catggacccg   31140
cagcagcggt tgctgctgga ggcgtcctgg gaggcgctgg aagtgtcgg cctcgacccg   31200
```

```
gcttcgttgc agggcaccga cgtcggcgtg ttcaccggcg cgggcgggtc gggctacggc    31260
ggcggcctca ccgggccgga gatgcagagt ttcgcgggca ccgggctggc ctcgagcgtg    31320
gcttcgggcc gggtgtccta cgtcttcggg ttcgagggac cggcggtcac gatcgacacg    31380
gcgtgctcgt cgtcgctggt ggcgatgcac ctcgccgcgc aggccctgcg ccaaggcgac    31440
tgctcgatgg cactggccgg cggcgcgatg gtgatgtcgg gccccgactc cttcgtcgtc    31500
ttctcccggc agcgggggct ggccaccgac gggcggtgca aggcgttcgc gtcgggcgcc    31560
gacggcatgg tgctcgccga gggcatcagc gtggtcgtgc tggagcggct ttcggtcgcg    31620
cgggaacgcg ggcaccgggt gctggccgtg ctgcgcggca gcgcggtgaa ccaggatggc    31680
gcgtcgaacg gcctgaccgc cccgaacggc ccttcccagc agcgcgtgat ccgcgccgcg    31740
ctggccaacg ccggaatcgg accgtccgat gtggacctcg tcgaggcgca cgggaccggg    31800
acgagcctgg gtgatcccat cgaggcgcag gccttgctgg cgacctacgg ccaggaccgg    31860
gagacgccgt tgtggctcgg ctcgctgaag tcgaacatcg gcacacgca ggcggccgcg     31920
ggcgtggcga gcgtgatcaa ggtcgtgcag gcgctgcggc acggcgtcat gccgccgacc    31980
ctgcacgtcg acgagcccag ctcgcaggtc gactggtccg aaggcgcggt ggaactgctg    32040
accgggagcc gggactggcc gcgcgggac cggccgcgcc gggccggggt gtcgtcgttc      32100
ggcgtcagcg gacgaacgt gcacctgatc atcgaggaag cccccgagga gcccgctgcg     32160
gccgtgccga cgtccgcgga cgtcgtgccg ctggtggttt ccgcacgcag cacgggttcc    32220
ctggccggtc aggccgaccg gctgaccgag gtggacgtcc ccctcggaca cctcgccggg    32280
gcgctggtgg ccgggcgcgc ggtgctcgag gaacgcgcgg tcgtggtcgc cggttcggcc    32340
gaagaagccc gcgcggggct gggtgcgctg gctcgcggtg aagccgcgcc cggcgtcgtg    32400
accgggaccg cgggcaagcc gggcaaggtc gtctgggtgt cccgggaca ggggacgcag     32460
tgggtgggca tgggccggga gctcctcgac gcgtccccgg tgttcgccga gcggatcaag    32520
gagtgcgcgg cggcactgga ccagtggacc gactggtcgc tgctggacgt cctgcgtggt    32580
gacggtgacc tggattctgt cgaggtgctg cagcccgcgt gcttcgcggt gatggtgggg    32640
ctggccgcgg tctgggagtc ggcggggtc cggccggacg ccgtcgtcgg ccactcgcag     32700
ggcgagatcg ccgcggcctg cgtgtccggc gcgctcaccc tcgacgacgc cgcgaaggtg    32760
gtggccctgc gcagccaggc gatcgcggcg cggctgtccg gccgcggcgg gatggcgtcg    32820
gtcgcgttga gcgaggacga ggcgaacgca cggctgggtt tgtgggacgg ccggatcgag    32880
gtggccgcgg tcaacggccc cgcctccgtg gtgatcgcgg gggacgccca gccctcgac    32940
gaggctttgg aggtgctggc cggggacggc gtccgcgtcc ggcaggtcgc ggtcgactac    33000
gcctcccaca cccggcacgt cgaggacatc cgcgacaccc tcgccgagac gctggccggg    33060
atcaccgcgc aggccccgga cgtgccgttc cgctccaccg tcaccggcgg ctgggtgcgg    33120
gacgccgacg tcctggacgg cgggtactgg taccgcaacc tgcgcaacca ggtccggttc    33180
ggcccggccg tggccgagct gctcgagcag ggccacgggg tgttcgtcga ggtcagcgcc    33240
caccccgtgc tggtgcagcc gatcagcgag ctcaccgacg cggtcgtcac cgggacgctg    33300
cggcgcgacg acggcggcct gcgccgcctg ctgacgtcga tggccgagct gttcgtccgc    33360
ggtgttcgcg tcgactgggc cacgctggtc ccgcccgcgc gcgtgaccct cccgacgtac    33420
gccttcgacc accagcactt ctggctccgg ccggccgcgc aggcggacgc cgtctcgctc    33480
ggccaggccg cggcggagca cccgctgctc ggcgcggtcg tccggctgcc gcagtcggac    33540
ggcctggtct tcacctcgcg gctgtcgctg cggacgcacc cgtggctggc cgaccacacc    33600
```

-continued

```
atcggcggcg tggtgctgtt ccccggcacc gggctggtcg aactggccgt gcgggccggc   33660
gacgaggccg ggtgcccggt cctggacgaa ctcgtgaccg aggcgccgct ggtcgtgccc   33720
gggcagggcg gagtgaacgt ccaggtcacg gtgagcggcc cggaccagaa cggcttgcgc   33780
acggtggaca tccactccca gcgcgacgac gtgtggaccc ggcacgcgac cggaacggtc   33840
tcggcgaccc cggcgagcag ccccggcttc gacttcaccg cgtggccgcc gccggacggg   33900
cagcgcgtcg agatcggcga cttctacgcc gacctcgccg agcgcgggta cgcgtacggg   33960
cccttgttcc agggcgtgcg ggcggtgtgg cagcgcggcg aagacgtgtt cgccgaggtc   34020
gcgctgcccg aagaccggcg ggaggacgcc gcccggttcg gcctgcaccc ggcgttgctg   34080
gacgcggccc tgcagaccgg gacgatcgcc gcggccgcgt ccggtcagcc gggcaagtcc   34140
gtgatgccgt tctcgtggaa ccggctggcg ctgcacgccg tcggggccgc gggcctccgg   34200
gtccgcgtgg ccccggcgg accggacgcg ctgaccgtcg aggccgccga cgagaccggc   34260
gccccggtcc tcaccatgga ctcgctgatc ctgcgtgaag tcgccctcga ccagctggac   34320
actgcgcgcg ccggctcgct ctaccgggtg gactggacgc cactgcccac tgtggacagt   34380
gcggtgcccg ctggtcgggc cgaggtgctg gaagctttcg gcgaggagcc cctggacctg   34440
accggccggg tgctggccgc cctgcaggcg tggctttccg acgcggcgga ggaagcccgc   34500
ctggtcgtgg tgacccgggg tgcggtgccc gccggagacg gtgtggtgag cgatccggcg   34560
ggtgccgcgg tgtggggcct ggtccgggcc gcgcaggcgg agaacccgga ccggttcgtc   34620
ctgctcgaca ccgacggcga ggtgccgctg gaagcggtgc tggcgaccgg tgagccgcag   34680
ctcgcgctgc gcggcacgac gttctcggtg ccccggctcg cccgcgtcac cgaaccggcg   34740
gaagccccgc tgacgttccg tccggacggg acggtcctgg tctccggcgc cgggacgctg   34800
ggtgcgctcg ccgcccgcga cctcgtcacc cggcacggcg tccggcggct cgtgctggcc   34860
agccggcgcg gccgggccgc cgagggcatc gacgacctcg tcgccgagct gaccgggcac   34920
ggcgccgaag tgacggtcgc cgcctgcgac gtctccgacc gcgaccaggt ggcggcgctg   34980
ctcaaggaac acgcgctgac cgcggtggtg cacacggcgg gcgtgttcga cgccggtgtc   35040
accggcgcgc tgacccggga gcggctggcc aaggtgttcg cgcccaaggt cgacgcggcc   35100
aaccacctcg acgagctgac ccgcgacctg gacctcgacg cgttcatcgt ctactcgtcc   35160
gcctcctcga tcttcatggg cgcgggcagc ggcgggtacg cggcggcgaa cgcctacctc   35220
gacggcctga tggccgcccg gcgcgcgcg ggcctgccgg ggctgtcgct ggcctggggc   35280
ccgtgggagc agctcaccgg catggccgac accatcgacg acctcaccct ggcccggatg   35340
agccggcgcg aaggccgcgg cggcgtccgc gcgctcggct ccgccgacgg catggagctg   35400
ttcgacgccg cgctcgcggc cgggcaggcg ctgctggtgc cgatcgagct cgacctgcgc   35460
gaggtgcggg ccgacgcggc cggcggcggc acggtgccgc acctgctgcg cgggctggtc   35520
cgcgcgggcc ggcaggcggc gcggacggcg gccaccgagg acggcggcct ggaacgccgg   35580
ctggccgggc tcaccgtggc cgaacaggaa gcgctgctgc tcgacctcgt ccgcggtcag   35640
gtcgccgtcg tgctcgggca cgccgacagc tccggcgtcc gcgccgacgc ggcgttcaag   35700
gacgccgggt tcgactcgct gacgtcggtg gagctgcgca accggctgcg cgagacgacc   35760
ggcctgaaac tgcccgcgac gctggtcttc gaccatccga acccgctggc actggcccgg   35820
cacctgcggg cggaactcgc cgtcgacgag gcatccccgg ccgatgcggt gctggccggg   35880
ctcgccgggc tggaggcggc catcgcggcc gccggcgccc cggacggcga ccggatcacc   35940
```

```
gcgcggctgc gggaactgct caaggccgcc gaggcggccg aggcccggcc gggcacctcc   36000
ggcgatctcg acacggccag cgacgaggaa ctgttcgccc tcgtcgacgg gctcgactga   36060
aaccgctgtg acatccgggg cttcgccacc cgggccccga aaagcaagca cacgtgagag   36120
ttctgggagt tgagttcagt ggctgacgag ggacaactcc gcgactacct caagcgggcc   36180
atcgccgacg cccgcgacgc ccgcacgcgc ctgcgcgagg tcgaggagca ggcgcgggag   36240
ccgatcgcca tcgtcgccat ggcgtgccgg tacccgggcg gggtgtcctc gcccgaggac   36300
ctgtggcggc tggtggccga ggggaccgac gccgtctccg cgttccccgg cgaccgcggc   36360
tgggacgtcg acgggctcgt cgacccggac cccgaccgcc cgggcacgac gtacacggac   36420
cagggtggct cctccacga ggccggcctc ttcgacgcgg ggttcttcgg gatctcgccg   36480
cgggaggccg tcgcgatgga cccgcagcag cggctgctgc tggagacgtc ctggaggcc   36540 atcgaacgca ccggcaccga cccgcttttcg ctgaagggca gcgacatcgg cgtcttcacc   36600
ggcgtcgcga gcatgggtta cggcgccggt ggcggcgtgg tcgcgccgga gctggagggt   36660
ttcgtcggca ccggtgcggc gccgtgcatc gcgtccggcc gggtgtcgta cgtcctcggc   36720
ttcgaaggcc cggcggtcac cgtcgacacc gggtgttcgt cgtcgctggt ggcgatgcac   36780
ctcgccgcgc aggcgctgcg gcggggtgag tgctcgatgg ctctggccgg cggcgcgatg   36840
gtgatggccc agccgggttc gttcgtgtcc ttctcgcggc aacgcgggct cgccctggac   36900
gggcgctgca aggcgttttc ggacagcgcc gacgggatgg gactggccga gggcgtcggc   36960
gtcatcgcgc tggaacggct gtcggtcgcc cgtgagcgtg ggcaccgggt gctggccgtg   37020
ctgcgcggta tcgcggtgaa ccaggatggc gcgtcgaacg gcttgaccgc cccgaacggc   37080
ccgtcccagc agcgggtgat ccgcgccgcg ctggccgaag ccgggctgtc gccgtccgat   37140
gtggacgccg tcgaagggca cgggacgggc acgacgctgg gcgatccgat cgaagcgcag   37200
gcgttgctgg ccacctacgg caagggccgg gacccggaga agccgctctg gctgggctcg   37260
gtgaagtcga acctcgggca cacgcaagcg gccgcgggcg tggccagcgt gatcaagatg   37320
gtgcaggcgc tgcgccacgg cgtgctgccc ccgacgctgc acgtcgaccg gccgtccacc   37380
gaagtcgact ggtcggccgg tgcggtctcg ctgttgacga aggctcggga gtggccgcgc   37440
gaagggcggc cgcgccgggc cggggtgtcc tcgttcggga tcagcgggac caacgcgcac   37500
ctcatcctgg aggaagcgcc cgaggaggag ccgcccgtcg ccgaagcgcc ttccgccgga   37560
gtggtgcccg tggtggtgtc ggctcgtggg gccctggcgg gtcaggccgg ccggctggcc   37620
gcgttcctcg aggcgtccga cgagccgttg gtgaccgtcg ccggggcgct gatctgcggc   37680
cggtcccggt tcggcgaccg ggccgtcgtg gtggcgggca cgcgcgcaga ggcgacggcc   37740
gggctggccc cgctggcccg cggcgaaagc ccgccgacg tcgtgaccgg cacggtcgcg   37800
gcctcgggcg tgccgggcaa gctcgtgtgg gtgttcccgg ccagggttc gcagtgggtg   37860 ggcatgggcc gggagctcct cgaagcctcg ccggtgttcg ccgcgcggat cgcggagtgc   37920
gcggctgccc tcgaaccgtg gatcgactgg tcgctgctgg acgtcctccg tggcgagggc   37980
gacctcgacc gcgtcgacgt ggtgcagccc gcgagtttcg cggtgatggt cggcctggcc   38040
gcggtgtggt cgtccgtcgg ggtggtgccc gacgcggtgc tcgggcactc gcaggggag   38100 atcgcggcgg cgtgcgtgtc gggggcgttg tcgctgcagg acgcggcgaa ggtggtcgcg   38160
ttgcgcagcc aggcgatcgc ggcgaagctg gccggccgcg gcgcatggc ctcggtcgcg   38220 ctgagcgagg aagacgcggt tcgcgcggttg cggcactggg cggaccgggt cgaggtggcc   38280
gcggtcaaca gcccgtcgtc ggtggtgatc gccggcgacg ccgaagccct cgaccaggcc   38340
```

```
ctcgaagcac tgaccggcca ggacatccgg gtccggcggg tggcggtgga ctacgcctcg    38400
cacacccggc acgtcgaaga catccaggag cccctcgccg aggcactggc cgggatcgag    38460
gcgcacgcgc cgaccctgcc gttcttctcg accctcaccg tgactggat  tcgcgaagcg    38520 ggcgtcgtgg acggcggcta ctggtaccgg aacctgcgca accaggtcgg tttcggcccg    38580
gcggtggccg agctgctcgg cctcggccac cgggtgttcg tcgaggtcag cgcgcacccc    38640
gtgctcgtcc aggcgatcag cgcgattgcc gacgacaccg acgcggtcgt caccggctcg    38700
ctgcggcgcg aggagggcgg cctgcggcgg ctgctgacgt cgatggccga gctgttcgtc    38760
cgcggagtcg acgtggactg ggccacgatg gtgccgccag cgcgggtcga tttgccgacc    38820
tacgccttcg accaccagca ctactggctg cggtacgtcg agaccgcgac cgacgcggcc    38880
ggtccggtgg tccggctgcc gcagacgggc ggcctggtct tcaccaccga gtggtcgctg    38940
aagtcacagc cgtggctggc cgagcacacc ctggaagacc tggtcgtcgt ccccggcgcg    39000
gcactggtcg agctggccgt ccgggccggt gacgaggccg ggaccccggt gctggacgaa    39060
ctcgtcatcg agacgcccct ggtcgtgccg gaacgcggcg cgatccgggt gcaggtcacg    39120
gtgagcggac cggacgacgg cacacggacc ctggaagtgc attcccagcc cgaagacgcc    39180
accgacgaat ggacccggca cgccaccggc acgctgtcgg cgaccccgga cgaaagcagc    39240
gggttcgact tcacggcctg gccgccccg  ggcgcccggc agctcgacgg cgttccggcg    39300
atctggcggg ccggcgacga gatcttcgcc gaagtctccc tgcccgacga tgcggacgcc    39360
gaggcattcg gcatccaccc cgcgctcctg gacgcggccc tgcaccccgc cctgcccggc    39420
gatgacggtc tgacgcagcc catggaatgg cgtggcctga cgctgcacgc cgcggggggcg    39480 tcgacgctgc gggtccggtt ggtgcccggc gggttcctgg aagcggccga cggcgccggc    39540
agcctggtcg tcacggcgaa ggaggttgcc ctccgcccgg tgacgatcgc gcggtcgcgc    39600
accaccaccc gagactcgct gttccagctg aactggatcg agctgcccga gagtggcgtg    39660
gtggccgcgg cagacgacac cgaggtgctg gaggtgcccg cgggcgattc cccgctggcg    39720
gcgacctccc gagtcttgga gcggctccag acctggctga ccgagcccga ggcggaacag    39780
ctggtcgtcg tgacgcgcgg cgcggtgccc gccggggaca ccccggtgac cgacccggcc    39840 gcggcggcg  tctggggcct ggtccggtcc gcgcaggcgg agaacccgga ccggatcgtc    39900
ctgctcgaca ccgacggcga agtcccgctg ggtgcggtgc tggccggcgg cgagccgcag    39960
gtcgcggtgc gcggcacggc gctgtacgtc ccgcgcctgg cccgcgccga cgcggccccg    40020
gtatccggtc tacatgggac ggtcctcgtc tccggtgccg gtgtgctcgg cgagatcgtg    40080
gcgcggcacc tggtcacccg ccacggcgtg cgcaagctgg tgctcgccag ccgccgcggc    40140
ctggacgccg acggcgcgaa ggacctcgtc accgacctca ccggcgaggg cgcggacgtg    40200
tccgtcgtcg cctgcgacct ggccgatcgg aaccaggtgg ccgcgctgct ggccgaccac    40260
cgcccggcga gcgtcatcca cacggcgggc gtcctcgacg acggcgtcat cgggacgctg    40320
accccggagc ggctggccaa ggtgttcgcg cccaaggtcg acgcggtccg ccatctcgac    40380
gagctgactc gcgacctcga cctcgacgcg ttcgtcgtgt tctcctccgg ctccggcgtg    40440
ttcggttcgc cggggcaggg caactacgcg gcggcgaacg cgttcctgga cgcggcgatg    40500
gcgagccgcc gcgcggcggg tcttcctggt ctctcgctgg cgtggggcct gtgggaacag    40560
gccaccggca tgaccgcgca cctcggcggc accgaccagg cccggatgag ccggggcggg    40620
gtgcggccga tcacggccga ggaaggcatg gccctgttcg acacggcact gggtgcgcag    40680
```

```
cccgcgctgc tcgtgccggt caagctcgac ctgcgggagg tgcgggccgg cggggccgtg   40740
ccgcacctgc tgcgcgggct ggtccgggcc gggcggcggc aggcccaagc cgcgtccaca   40800
gtggacaacc agctgctggg ccggctggcc gggctgggcg cgcccgagca ggaggcgctg   40860
ctcgtcgacc tcgtgcgcgg ccaggtcgcg gcggtgctcg gcacgccgg gccggacgcg    40920 gtccgcgccg acacggcgtt caaggacgcc gggttcgact cgctcacctc ggtcgacctg   40980
cgcaaccggc tgcgggagag caccgggctg aagctgcccg ccacgctcgc cttcgactac   41040
ccgaccccgc tggtcctcgc ccggcacctg cgtgacgagc tcggggccgg cgacgacgcg   41100
cttccggtgg tgcacgcgcg gctcgaagac gtcgaggcgc tgctcggcgg gctgcgcctc   41160
gacgaatcca cgaagaccgg tctcaccctc cggctgcagg gcctggtcgc ccggtgcaac   41220
ggcgtgaacg accagaccgg cggcgaaacg ctggcggacc ggctcgaggc cgcgtccgcc   41280
gacgaagtcc tcgacttcat cgacgaggag ctgggtctca cctgaccccg gttcgagacc   41340
gacgttccag caaccttgt gaggacccga gaatggccac ggacgagaaa ctcctcaaat    41400
acctcaagcg cgtcacggcg gagctgcaca gcctgcgcaa gcagggtgcc cggcacgccg   41460
acgagccgct cgccgtcgtc gggatggcct gccggttccc gggtgggggtg tcctcgcccg   41520 aagacctgtg gcagctcgtg gccggcgggg tcgacgccct ttcggacttc cccgacgacc   41580
ggggctggga gctggacggc ctgttcgacc cggaccccga ccaccccggg acgtcgtaca   41640
ccagccaggg cggcttcctg cgtggcgccg ggctgttcga cgcgggcctg ttcggcatct   41700
cgccgcgcga ggccctcgtc atggaccgc agcagcgggt gctgctggag acgtcgtggg    41760
aggccctcga agacgccggg gtcgacccgc tttcgctgaa gggcagcgac gtcggcgtgt   41820
tctccggcgt cttcacccag ggctacgcg ccggggcgat cacgccggac ctcgaggcgt    41880
tcgcgggcat cggggcggcg tcgagcgtgg cgtcgggccg ggtgtcctac gtcttcgggc   41940
tcgaaggacc ggcggtcacc atcgacaccg cgtgttcgtc gtcgctggtg gccatccacc   42000
tcgccgcgca ggccctgcgc gcgggcgagt gctcgatggc gctcgccggc ggggcgacgg   42060
tgatgccgac gcccggcacc ttcgtcgcgt tctcgcggca gcgggtgctg gctgccgacg   42120
gccggtccaa ggccttctcc tcgaccgcgg acggcaccgg ctgggccgag ggcgccgggg   42180
tgctcgtcct cgaacggctt tcggtcgcgc aggagcgcgg ccaccggatt ctcgccgtgc   42240
tgcgcggcag cgcggtcaac caggatggcg cctccaacgg cctgaccgcg ccgaacgggc   42300
cttcgcagca gcgggtgatc cgcaaggcgc tcgcgggcgc cgggctggtc gcgtccgatg   42360
tggacgtcgt ggaggcgcac ggcacgggca ccgcgctggg cgacccgatc gaagcgcagg   42420
cgctgctggc gacctacggc cagggccgtg agcggccgct gtggctgggg tcggtcaagt   42480
cgaacttcgg gcacacgcag gcggccgccg ggtcgcggg cgtgatcaag atggtccagg    42540
ccctgcggca cggcgccatg ccgccgaccc tgcacgtggc cgagccgacg ccggaggtcg   42600
actggtcggc cggtgcggtg gaactgctga ccgagccgcg cgagtggccc gccggtgatc   42660
ggccgcgccg gccggggtg tccgcgttcg ggatcagcgg gacgaacgcc cacctgatcc    42720
tggaggaggc gccccggcc gacgcggtcg cggaagaacc ggagttcaag gggccggtgc    42780
cgctggtcgt ctcggcgggc agccccacat ctttggcggc tcaggccggc cggctcgcgg   42840
aggtcctggg gtccggtggt gtgtcccggg cccggctggc gagcggggctg ctgtcgggcc    42900 gggcgctgct cggtgaccgc gcggtcgtgg tcgcgggaac ggacgaggac gcggtggccg   42960
ggttgcgtgc gctggcccgc ggggaccgcg cgcccgcgt gctgaccggt tcggccaagc    43020
acggcaaggt cgtctacgtc ttccccggcc agggttcgca gcggctcggg atgggccgcg   43080
```

```
agctctacga ccggtacccg gtgttcgcga cggcgttcga cgaggcttgc gagcagctgg    43140
acgtctgtct ggccggccgt gccgggcacc gcgtgcggga cgtcgtgctc ggcgaagtgc    43200
ccgccgaaac cgggctgctg aaccagacgt tcttcaccca agcccggctg ttcgcggtgg    43260
agagcgcgct gttccggctc gccgaatcct ggggtgtccg gccggacgtg gtgctcggcc    43320
actccatcgg ggagatcacc gccgcgtatg ccgcgggcgt cttctcgctg ccggacgccg    43380
cccggatcgt cgcggcgcgc ggccggctga tgcaggcgct ggcgccgggc ggggcgatgg    43440
tcgccgtcgc cgcctccgaa gccgaggtgg ccgaactgct cggcgacggc gtggaactcg    43500
ccgccgtcaa cggcccttcg gcggtagtcc tttccgggga cgcggacgcg gtcgtcgcgg    43560
ccgccgcccg catgcgcgag cgcgggcaca agaccaagca gctcaaggtt tcgcacgcgt    43620
tccactccgc gcggatggcg ccgatgctgg cggagttcgc cgccgagctg gccggcgtga    43680
cgtggcgcga gccggagatc ccggtggtct ccaacgtgac cggccggttc gccgagcccg    43740
gcgaactgac cgagccgggc tactgggccg agcacgtgcg gcggccggtg cggttcgccg    43800
agggcgtcgc ggccgcgacg gagtccggcg gctcgctgtt cgtggagctc gggccggggg    43860
cggcgctgac cgccctcgtc gaggagacgg ccgaggtcac ctgcgtcgcg gccctgcggg    43920
acgaccgccc ggaggtcacc gcgctgatca ccgcggtcgc cgagctgttc gtccgcgggg    43980
ttgcggtcga ttggccggcc ctgctgccgc cggtcaccgg gttcgtcgac ctgccgaagt    44040
acgccttcga ccagcagcac tattggctgc agcccgccgc gcaggccacg gacgcggcct    44100
cgctcgggca ggtcgcggcc gaccaccgc tgctgggcgc ggtggtccgg ctgccgcagt    44160
cggacggcct ggtcttcacc tcgcggctgt cattgaaatc gcaccgtgg ctggccgacc    44220
acgtcatcgg cggggtggtg ctcgtcgcgg gcaccgggct cgtcgagctg gccgtccggg    44280
ccggggacga ggccggctgc ccggtcctcg aagaactcgt catcgaggct ccgctggtcg    44340
tccccgacca cggcggggtc cggatccagg tcgtcgtggg ggcaccgggg gagaccggtt    44400
cgcgcgcggt cgaggtgtac tccctgcgcg aggacgccgg tgccgaagtg tgggcccggc    44460
acgccaccgg gttcctggct gcgacgccgt cgcagcacaa gccgttcgac ttcaccgcct    44520
ggccgccgcc cggcgtcgag cgcgtcgacg tcgaggactt ctacgacggc ctcgtcgacc    44580
gcgggtacgc ctacgggccg tcgttccggg gcctgcgggc ggtgtggcgg cgcggcgacg    44640
aagtgttcgc cgaggtcgcc ctggccgagg acgaccgcgc ggacgcggcc cggttcggca    44700
tccacccogg cctgctggac gccgccctgc acgcgggcat ggccggtgcc accaccacgg    44760
aagagcccgg ccggccggtg ctgccgttcg cctggaacgg cctggtgctg cacgcggccg    44820
gggcgtccgc gctgcgggtc cggctcgccc gagcggtcc ggacgccctg tcggtcgagg    44880
ccgcggacga ggccggcggt ctcgttgtga cggcggactc gctggtctcc cggccggtgt    44940
cggccgaaca gctgggcgcg gcggcgaacc acgacgcgtt gttccgcgtg gagtggaccg    45000
agatttcctc ggctggagac gttccggcgg accacgtcga agtgctcgaa gccgtcggcg    45060
aggatcccct ggaactgacc ggccgggtcc tggaggccgt gcagacctgg ctcgccgacg    45120
cagccgacga cgctcgcctg gtcgtggtga cccgcggcgc cgtccacgag gtgactgacc    45180
cggccggtgc cgcggtgtgg ggcctgatcc gggccgcgca ggcggaaaac ccggaccgga    45240
tcgtgctgct ggacaccgac ggtgaagtgc cgctaggccg ggtgctggcc accggcgagc    45300
cccaaacagc cgtccgaggc gccacgctgt tcgccccgcg gctggcccgc gccgaggccg    45360
cggaggcacc ggcagtgacc ggcgggacgg tcctgatctc gggcgccggc tcgctgggcg    45420
```

```
cgctcaccgc cggcacctg gtcgccggc acggagtccg gcggctggtg ctcgtcagcc    45480
gccgtggccc cgacgccgac ggcatggccg aactgaccgc tgaactcatc gctcagggcg    45540
ccgaggtcgc cgtagtcgct tgcgacctgg ccgaccggga ccaggtccgg gtactgctgg    45600
ccgagcaccg cccgaacgcc gtcgtgcaca cggccggtgt tctcgacgac ggcgtcttcg    45660
agtcgctgac gcgggagcgg ctggccaagg tcttcgcgcc caaagttact gctgccaatc    45720
acctcgacga gctgacccgc gaactggatc ttcgcgcgtt cgtcgtgttc tcctccgcct    45780
ccggggtctt cggctccgcc gggcagggca actacgccgc tgccaacgcc tacctggacg    45840
ccgtggtcgc caaccgccgg gccgcgggcc tgcccggcac atcgctggcc tggggcctgt    45900
gggaacagac cgacgggatg accgcgcacc tcggcgacgc cgaccaggcg cgggcgagtc    45960
gcggcggggt cctcgccatc tcacccgccg aaggcatgga gctgttcgac gcagcgccgg    46020
acgggctcgt cgtcccggtc aagctggacc tgcgcaagac ccgcgccggc gggacggtgc    46080
cgcacctgct gcgcggcctg gtccgccggg acggcagca ggcccgtccg gcgtccactg    46140
tggacaacgg actggccggg cgactcgccg ggctcgcgcc ggcggagcag gaggcgctgc    46200
tgctcgacgt cgtccgcacg caggtcgcgc tggtgctcgg gcacgccggg ccggaggccg    46260
tccgcgcgga cacggcgttc aaggacaccg gcttcgactc gctgacgtcg gtggaactgc    46320
gcaaccggct gcgcgaggcg agcgggctga agctgcccgc gacgctcgtc ttcgactacc    46380
cgacgccggt cgcgctggcc cgctacctgc gtgacgaact cggcgacacg gtggcaacaa    46440
ctccggtggc caccgcggcc gcagcggacg ccggcgagcc gatcgccatc gtcggcatgg    46500
cgtgccggct gccgggcggg gtcaccgatc ccgaaggcct gtggcgcctg gtgcgcgacg    46560
gcctcgaagg gctgtctccc ttccccgagg accggggctg ggacctggag aacctgttcg    46620
acgacgaccc cgaccgctcc ggcacgacgt acaccagccg gggcgggttc ctcgacggcg    46680
ccggcctgtt cgacgcgggc ttcttcggga tttcgccgcg cgaggcgctg gccatggacc    46740
cgcagcagcg gctgctgctc gaggcggcct gggaagccct cgaaggcacc ggtgtcgacc    46800
cgggctcgtt gaagggcgcc gacgtcgggg tgttcgccgg ggtgtccaac cagggctatg    46860
ggatgggcgc ggatccggcc gaactggcgg ggtacgcgag cacggcgggc gcttcgagcg    46920
tcgtctcggg ccgagtctcg tacgtcttcg ggttcgaagg accggcgtc acgatcgaca    46980 cggcttgctc gtcgtcgctg gtggcgatgc acctggccgg gcaggcgctg cggcagggcg    47040
agtgctcgat ggccctggcc ggtggcgtca cggtgatggg gacgcccggc acgttcgtgg    47100
agttcgcgaa gcagcgcggc ctggccggcg acggccggtg caaggcctac gccgaaggcg    47160
cggacggcac gggctggccc gagggcgtcg gggtcgtcgt gctggagcgg ctgtcggtgg    47220
cgcgcgagcg cgggcaccgg gtgctggccg tgctgcgcgg cagcgcggtc aactccgacg    47280
gcgcgtccaa cggcctgacc gcccccaacg ggccgtcgca gcaacgggtg atccgccggg    47340
ccctggccgg cgcggcctc gaaccgtccg atgtggacat cgtggaaggg cacggcaccg    47400
ggacggcgct gggcgacccg atcgaggcgc aggccctgct ggccacctac ggcaaggacc    47460
gcgacccgga gacgccgttg tggctggggt cggtgaagtc gaacttcggc cacacgcagt    47520
ccgcggccgg cgtggccggg gtgatcaaga tggtgcaggc gctgcgccac ggcgtcatgc    47580
cgcccaccct gcacgtggac cggcccacca gccaggtcga ctggtccgcg ggggccgtcg    47640
aagtgctgac cgaggcacgg gagtggccgc ggaacggccg tccgcgccgg gccggggtgt    47700
cctcgttcgg gatcagcggc acgaacgccc acctgatcat cgaagaagca ccggccgagc    47760
cacagcttgc cggaccaccg ccggacggcg gtgtggtgcc gctggtcgtc tcggctcgca    47820
```

-continued

```
gccccggtgc cctggccggt caggcgcgtc ggctggccac gttcctcggc gacgggcccc    47880
tttccgacgt cgccggtgcg ctgacgagcc gcgccctgtt cggcgagcgc gcggtcgtcg    47940
tggcggattc ggccgaggaa gcccgcgccg gtctgggcgc actggcccgc ggcgaagacg    48000
cgccgggcct ggtccgcggc cgggtgcccg cgtccggcct gccgggcaag ctcgtgtggg    48060
tgttccccgg gcaggggacg cagtgggtgg gcatggcccg cgaactcctc gaagagtctc    48120
cggtgttcgc cgagcggatc gccgagtgtg cggccgcgct ggagccgtgg atcggctggt    48180
cgctgttcga cgtcctccgt ggcgacggtg acctcgatcg ggtcgatgtg ctgcagcccg    48240
cgtgctttgc ggtgatggtc ggcttggccg cggtgtggtc ctcggccggg gtggtccccg    48300
atgcggtgct cggccactcc cagggtgaga tcgccgcggc gtgcgtgtcg ggtgcgttgt    48360
cgctggagga tgcggcgaag gtggttgccc tgcgcagcca ggccatcgcc gcgaagctct    48420
ccggccgcgg cgggatggct tcggtcgcct tgggcgaagc cgatgtggtg tcgcggctgg    48480
cggacggggt cgaggtggct gccgtcaacg gtccggcgtc cgtggtgatc gcgggggatg    48540
cccaggccct cgacgaaacg ctggaagcgc tgtccggtgc gggaatccgg gctcggcggg    48600
tggcggtgga ctacgcctcg cacacccggc acgtcgaaga catcgaagac accctcgccg    48660
aagcgctggc cgggatcgac gcccgggcgc cgctggtgcc gttcctctcc accctcaccg    48720
gcgagtggat ccgggacgag ggcgtcgtgg acggcggcta ctggtaccgg aacctgcgcg    48780
gccgggtgcg gttcggcccg gccgtcgagg cgctgctggc ccaggggcac ggtgtgttcg    48840
tcgagctcag cgcccacccg gtgctggtcc agccgatcac cgagctcacc gacgaaaccg    48900
ccgccgtcgt caccggttcg ctgcgccggg acgacggtgg cctgcgccgg ctgctgacct    48960
cgatggccga gctcttcgtc cgtggggtcg aagtggactg gacgtcgctg gtgccgccgg    49020
cccggggccga cctcccgacg tacgccttcg accacgagca ctactggctc cgcgccgcgg    49080
acaccgcttc cgacgccgtc tcgctggggc tggccggggc ggaccacccg ctgctcggcc    49140
cggtcgtgca gcttccgcag tccgacggcc tggtcttcac ttcccggctc tccctgcgct    49200
cgcacccctg gctggccgac cacgcggtcc gggacgtcgt gatcgtcccc ggcaccgggc    49260
tggtcgagct ggccgtgcgg gccggtgacg aagccggctg cccggtgctc gacgagctgg    49320
tgatcgaggc gccgctcgtg gtgccccgcc gcggcgggt ccgcgtgcag gtcgccctcg    49380
gcggccccgc cgacgacggt tcgcgcacgg tggacgtctt ctccctgcgc gaagacgcgg    49440
acagctggct ccggcacgcc acgggcgtgc tggtcccgga gaaccggccg cggggggaccg    49500
ccgcgttcga cttcgccgcc tggccgccac cggaggcgaa gcccgtggac ctcaccggtg    49560
cctacgacgt gctccgcggac gtcgggtacg gctacgggcc cacgttccgg gccgtgcggg    49620
ccgtgtggcg gcgcggcagc gggaacacca ccgagacctt cgccgagatc gccctgcccg    49680
aagacgcccg cgcggaagcc ggccggttcg gcatccaccc cgcgctgctg gacgcggccc    49740
tgcactcgac gatggtcagc gccgcggcgg acaccgagtc ctacggcgac gaagtgcggc    49800
tgccgttcgc gtggaacggg ctgccggctg cacgcggccgg cgcctcggtg ctgcgggtgc    49860
gcgtcgccaa gcccgagcgg gacagtctgt cgctggaggc cgtcgacgag tccggcggcc    49920
tggtcgtgac gctggattcc ctggtcgggc gcccggtgtc gaacgaccag ctgacgacgg    49980
cggcggggcc ggcgggcgcc ggcgggcgcc ggctcgctgt accgcgtgga ctggacgcca    50040
ttgtcctcag tggacacttc gggacggggtg ccgtcctggc ttccggtcgc caccgcggaa    50100
gaggtggcga cgctggccga cgacgtcctg accggcgcga ccgaggcgcc ggcggtggcc    50160
```

```
gtcatggagg ccgtcgccga cgagggttcc gtgctggcgc tcaccgtccg ggtgctggac    50220
gtggtccagt gctggctggc cggcggcggg ctggagggga cgaagctcgc gatcgtgacc    50280
cgcggcgcgg tgcccgccgg cgacggcgtg gtgcacgacc cggccgcggc cgcggtgtgg    50340
gggctggtcc gggccgcgca ggcggagaac ccggaccgga tcgtcctcct cgacgtcgag    50400
ccggaagccg acgtaccgcc gctgctgggt tcggtgctcg ccgacggcga gccgcaggtc    50460
gcggtgcgcg gaaccacgct gtccatcccc cgcctcgccc gcgccgcccg gcccgacccg    50520
gccgccgggt tcaagacccg gggaccggtg ctggtcaccg gcgggaccgg gtcgctcggc    50580
ggcctggtcg cccggcacct ggtcgagcgg cacggcgtcc ggcagctggt gctggcgagt    50640
cgccggggcc tggacgccga aggcgcgaag gacctggtca ccgacctcac cgcactgggg    50700
gccgacgtcg cggtcgccgc ttgcgacgtc gccgaccggg accaggtggc ggccctgctg    50760
accgagcacc ggccgtccgc cgtggtgcac acggccggcg tcccggacgc cggggtgatc    50820
gggacggtga cccggaccg gctggccgag gtgttcgcgc ccaaggtcac cgcggcccgg    50880
cacctcgacg agctgacccg cgacctggac ctcgacagtt tcgtcgtcta ctcctcggtt    50940
tccgcggtgt tcatgggcgc cggcagcggc agctacgccg cggcgaacgc gtacctggac    51000
gggctgatgg cccaccggcg cgcggccggc ctgccgggcc agtcgctggc gtggggctg    51060 tgggaccaga ccaccggcgg catggcggcc gggaccgacg aggccggccg ggcccggatg    51120
acccggcgcg gcggcctggt cgcgatgaaa cccgccgccg gactggacct cttcgacgct    51180
gccatcgggt ccggcgagcc gctgctggtg cccgcccagc tcgacctgcg gggcctgcgc    51240
gccgaagcgg cgggcggcac cgaagtgccg cacctgctgc gcggcctggt ccgcgccgga    51300
cgccagcagg cccgtgcggc gtccactgtg gaggagaact gggccggccg gctggccggg    51360
ctcgagccgg ccgagcgggg ccaggtcctc ctggaactgg tgcgcgccca ggtggcaggg    51420
gtcctgggct accgcgccgc ccaccaggtc gacccggacc agggcctgtt cgagatcggg    51480
ttcgactcgc tcaccgcgat cgaactccgc aaccggctgc gcgccaggac cgaacggaag    51540
atctcgcccg tgtcgtcttc cgaccatccc acgccggccc tgctcgccgc gcacttgaac    51600
gagctgctcc gaaagaaggt gtgaacgtgt tcgacgtgga gacctacctc cagcggatcg    51660
gctgcggcgg ggaaaccggc gtggacctcg aaacgctggc gaagctgcag aagagccacc    51720
tgatggcgat cccgtacagc agcctcgcct acgaactccg ggacgcggtg aacgtcgtcg    51780
acctcgacga ggacgacgtc ttcgtcacca gcatcgccga agggcagggc ggcgcctgct    51840
accacctgaa ccggctgttc caccggctcc tgaccgaact cggctacgac gtcacgccgc    51900
tggccggcag caccgccgaa ggccgggaga ccttcggcac cgacgtcgag cacatgttca    51960
acctggtcac cctggacggc gccgactggc tcgtggacgt cggctacccc ggccccacct    52020
acgtcgagcc actggcggtc tcgcccgcgg tgcagaccca gtacgggagc cagttccggt    52080
tggtggaaca ggaaaccggt tatgcgctgc aacgccgggg tgcggtcacc cgctggagcc    52140
tcgtctacac gttcacgacg caaccgcgtc agtggagtga ctggaaggaa ctggaggaca    52200
acttccgggc cctcgtgggg gacaccaccc gcaccgacac gcaggaaacc ctgtgcggcc    52260
gcgcgttcgc gaacggccag gtcttcctgc ggcagcgccg ctacctgacg gtcgagaacg    52320
gccgcgagca ggtgcgcacg atcaccgacg acgacgagtt ccgggcgctg gtgtcccgcg    52380
tgctgtccgg cgaccacggc tgaactggcg aaaggcacga cgatgacgga aaaagcgggc    52440
ctgctggcga agttcgccgg cctctgcaaa accgcctacg agcaccacta catcccgtac    52500
ctgcacttct tctacggcgg cgagtacctc caccacggca gcgagccggt gtcccggatc    52560
```

-continued

```
gcggacctgc cgtacgtgac cgtgccggag ccgcggaaga aggcgccgtg aggacgacga    52620
tcccggtccg cctggcggaa cggtcctacg acgtgctcgt cggccccggg gtgcgggcgg    52680
cgctgcccga ggtcgtccgg cggctcggcc cgagacgggc cgtggtcgtg tcggcccggc    52740
cggcggactg ggtgcccggc accggcgtcg agaccctgct gctccaggcg cgcgacggcg    52800
agccgaccaa cgcggctgtcc acagtggagg aactgtgcgg tgagttcgcg cggttcgggc    52860
tcacccggtc cgacgtcgtg gtctcctgcg gcggcggcac gaccacggac gtcgtcgggc    52920
tcgcggccgc gctgtaccac cgggggggtcg ccgtggtcca cctgcccacg tccctgctcg    52980
cccaggtcga cgccagcgtc ggcgggaaga ccgcggtgaa cctgccggcg ggcaagaacc    53040 tcgtcgggc gtactggcag cccagcgcgg tgctgtgcga cacggactac ctgacgacga    53100
tgccgcggcg ggaggtgctg aacggcctcg gcagatcgcc ccgctgccac ttcatcggcg    53160
cgccggacct gcgggggcgc tcgcgcccgg agcagatcgc cgccagcgtc accctcaagg    53220
cgggcatcgt cgcgcaggac gagcgggaca ccggcccgcg gcacctgctc aactacggcc    53280
acacgctggg gcacgcgctg gagatcgcga ccggcttcgc cctgcgccac ggcgaggcgg    53340
tggcgatcgg cacggtcttc gcgggccggc tggccggcgc gctcggccgc ctcgaccagt    53400
ccggtgtgga cgaacacctc gccgtcgtcc gccactacgg cctgcccgcc cgcgctgcccg    53460 cggacgtcga cccggcggtg ctcgtccggc agatgtaccg ggacaagaag gcgatcaccg    53520
ggctcgcctt cgtcctggcc gggccgcggg gcgcggagct ggtgagcgac gtgccggcgc    53580
cggtcgtcac cgacgtcctg gaccggatgc cccgcgacag cctggaaaac ctggtgggga    53640
cgacggaagc ggcggcgccg tgaagcggca gccggacttc gcggcccacg gccgggcggt    53700
cgaccgggtg ctggccggcc ggctgagcgc ggcgctggcc cggccggccg cgcagcagcc    53760
gggctggccg gacgccgagc gggcggccga ggtgaattc                           53799
```

<210> SEQ ID NO 4
<211> LENGTH: 4572
<212> TYPE: PRT
<213> ORGANISM: Amycolatopsis mediterranei

<400> SEQUENCE: 4

```
Met Phe Tyr Thr Ser Gly Thr Thr Gly Arg Pro Lys Gly Val Val Ser
  1               5                  10                  15

Thr Gln Arg Asn Cys Leu Trp Ser Val Ala Ser Cys Tyr Val Pro Phe
             20                  25                  30

Pro Gly Leu Ser Asp Gln Asp Arg Val Leu Trp Pro Leu Pro Leu Phe
         35                  40                  45

His Ser Leu Ser His Ile Ala Cys Val Leu Ser Ala Thr Val Val Gly
     50                  55                  60

Ala Ser Val Arg Ile Ala Asp Gly Ser Ala Asp Val Met Arg
 65                  70                  75                  80

Leu Ile Glu Ala Glu Ser Ser Thr Phe Leu Ala Gly Val Pro Thr Thr
                 85                  90                  95

Tyr His His Leu Val Arg Ala Ala Arg Gln Arg Gly Phe Ser Ala Pro
            100                 105                 110

Ser Leu Arg Ile Gly Leu Ala Gly Gly Ala Val Leu Gly Ala Gly Leu
        115                 120                 125

Arg Ser Glu Phe Glu Glu Thr Phe Gly Val Pro Leu Ile Asp Ala Tyr
    130                 135                 140

Gly Ser Thr Glu Thr Cys Gly Ala Ile Thr Met Asn Pro Pro Asp Gly
```

-continued

```
           145                 150                 155                 160
       Ala Arg Val Glu Gly Ser Cys Gly Leu Ala Val Pro Gly Val Asp Val
                       165                 170                 175
       Arg Val Val Asp Pro Asp Thr Gly Leu Asp Val Pro Ala Gly Glu Glu
                       180                 185                 190
       Gly Glu Val Trp Val Ser Gly Pro Asn Val Met Leu Gly Tyr His Asn
                       195                 200                 205
       Ser Pro Glu Ala Thr Ala Ala Met Arg Asp Gly Trp Phe Arg Thr
                   210                 215                 220
       Gly Asp Leu Ala Arg Arg Asp Asp Ala Gly Tyr Phe Thr Ile Cys Gly
       225                 230                 235                 240
       Arg Ile Lys Glu Leu Ile Ile Arg Gly Gly Ala Asn Ile His Pro Gly
                       245                 250                 255
       Glu Val Glu Ala Val Leu Arg Thr Val Asp Gly Val Ala Asp Ala Ala
                       260                 265                 270
       Val Gly Gly Val Pro His Asp Thr Leu Gly Glu Val Pro Val Ala Tyr
                       275                 280                 285
       Val Ile Pro Gly Pro Thr Gly Phe Asp Pro Ala Leu Ile Glu Lys
                   290                 295                 300
       Cys Arg Glu Gln Leu Ser Ala Tyr Lys Val Pro Asp Arg Ile Leu Glu
       305                 310                 315                 320
       Val Ala His Ile Pro Arg Thr Ala Ser Gly Lys Ile Arg Arg Gly Leu
                       325                 330                 335
       Leu Thr Asp Glu Pro Ala Gln Leu Arg Tyr Ala Ala Thr Glu His Glu
                       340                 345                 350
       Glu Gln Ser Arg His Ala Asp Glu Ser Val Ala Ala Leu Arg Ala
                   355                 360                 365
       Arg Leu Ser Gly Leu Asp Glu Arg Ala Gln Cys Glu Leu Leu Glu Asp
           370                 375                 380
       Leu Val Arg Thr Gln Ala Ala Asp Val Leu Gly Gln Pro Val Pro Asp
       385                 390                 395                 400
       Gly Arg Ala Phe Arg Asp Leu Gly Phe Thr Ser Leu Ala Ile Val Glu
                       405                 410                 415
       Leu Arg Asn Arg Leu Thr Glu His Thr Gly Leu Trp Leu Pro Ala Ser
                       420                 425                 430
       Ala Val Phe Asp His Pro Thr Pro Ala Ala Leu Ala Ala Arg Val Arg
                       435                 440                 445
       Ala Glu Leu Leu Gly Ile Thr Gln Ala Val Ala Glu Pro Val Val Ala
                       450                 455                 460
       Ala Asp Pro Gly Glu Pro Ile Ala Ile Val Gly Met Ala Cys Arg Leu
       465                 470                 475                 480
       Pro Gly Gly Val Ala Ser Pro Glu Asp Leu Trp Arg Leu Val Ala Glu
                       485                 490                 495
       Arg Val Asp Ala Val Ser Glu Phe Pro Gly Asp Arg Gly Trp Asp Leu
                       500                 505                 510
       Asp Ser Leu Ile Asp Pro Asp Arg Glu Arg Ala Gly Thr Ser Tyr Val
                       515                 520                 525
       Gly Gln Gly Gly Phe Leu His Asp Ala Gly Glu Phe Asp Ala Gly Phe
                   530                 535                 540
       Phe Gly Ile Ser Pro Arg Glu Ala Val Ala Met Asp Pro Gln Gln Arg
       545                 550                 555                 560
       Leu Leu Leu Glu Thr Ser Trp Glu Ala Leu Glu Asn Ala Gly Val Asp
                       565                 570                 575
```

```
Pro Ile Ala Leu Lys Gly Thr Asp Thr Gly Val Phe Ser Gly Leu Met
            580                 585                 590

Gly Gln Gly Tyr Gly Ser Gly Ala Val Ala Pro Glu Leu Glu Gly Phe
            595                 600                 605

Val Thr Thr Gly Val Ala Ser Ser Val Ala Ser Gly Arg Val Ser Tyr
            610                 615                 620

Val Leu Gly Leu Glu Gly Pro Ala Val Thr Val Asp Thr Ala Cys Ser
625                 630                 635                 640

Ser Ser Leu Val Ala Met His Leu Ala Ala Gln Ala Leu Arg Gln Gly
                645                 650                 655

Glu Cys Ser Met Ala Leu Ala Gly Gly Val Thr Val Met Ala Thr Pro
            660                 665                 670

Gly Ser Phe Val Glu Phe Ser Arg Gln Arg Ala Leu Ala Pro Asp Gly
            675                 680                 685

Arg Cys Lys Ala Phe Ala Ala Ala Asp Gly Thr Gly Trp Ser Glu
            690                 695                 700

Gly Val Gly Val Val Leu Glu Arg Leu Ser Val Ala Arg Glu Arg
705                 710                 715                 720

Gly His Arg Ile Leu Ala Val Leu Arg Gly Ser Ala Val Asn Gln Asp
                725                 730                 735

Gly Ala Ser Asn Gly Leu Thr Ala Pro Asn Gly Leu Ser Gln Gln Arg
            740                 745                 750

Val Ile Arg Arg Ala Leu Ala Ala Ala Gly Leu Ala Pro Ser Asp Val
            755                 760                 765

Asp Val Val Glu Ala His Gly Thr Gly Thr Thr Leu Gly Asp Pro Ile
            770                 775                 780

Glu Ala Gln Ala Leu Leu Ala Thr Tyr Gly Gln Arg Lys Gln Pro
785                 790                 795                 800

Leu Trp Leu Gly Ser Leu Lys Ser Asn Ile Gly His Ala Gln Ala Ala
            805                 810                 815

Ala Gly Val Ala Gly Val Ile Lys Met Val Gln Ala Leu Arg His Glu
            820                 825                 830

Thr Leu Pro Pro Thr Leu His Val Asp Lys Pro Thr Leu Glu Val Asp
            835                 840                 845

Trp Ser Ala Gly Ala Ile Glu Leu Leu Thr Glu Ala Arg Ala Trp Pro
            850                 855                 860

Arg Asn Gly Arg Pro Arg Arg Ala Gly Val Ser Ser Phe Gly Val Ser
865                 870                 875                 880

Gly Thr Asn Ala His Leu Ile Leu Glu Glu Ala Pro Ala Glu Pro
                885                 890                 895

Val Ala Ala Pro Glu Leu Pro Val Val Pro Leu Val Val Ser Ala Arg
            900                 905                 910

Ser Thr Glu Ser Leu Ser Gly Gln Ala Glu Arg Leu Ala Ser Leu Leu
            915                 920                 925

Glu Gly Asp Val Ser Leu Thr Glu Val Ala Gly Ala Leu Val Ser Arg
            930                 935                 940

Arg Ala Val Leu Asp Glu Arg Ala Val Val Ala Gly Ser Arg Glu
945                 950                 955                 960

Glu Ala Val Thr Gly Leu Arg Ala Leu Asn Thr Ala Gly Ser Gly Thr
                965                 970                 975

Pro Gly Lys Val Val Trp Val Phe Pro Gly Gln Gly Thr Gln Trp Ala
            980                 985                 990
```

```
Gly Met Gly Arg Glu Leu Leu Ala Glu Ser Pro Val Phe Ala Glu Arg
        995                 1000                1005

Ile Ala Glu Cys Ala Ala Ala Leu Ala Pro Trp Ile Asp Trp Ser Leu
    1010                1015                1020

Val Asp Val Leu Arg Gly Glu Gly Asp Leu Gly Arg Val Asp Val Leu
1025                1030                1035                1040

Gln Pro Ala Cys Phe Ala Val Met Val Gly Leu Ala Ala Val Trp Glu
                1045                1050                1055

Ser Val Gly Val Arg Pro Asp Ala Val Val Gly His Ser Gln Gly Glu
                1060                1065                1070

Ile Ala Ala Ala Cys Val Ser Gly Ala Leu Ser Leu Glu Asp Ala Ala
        1075                1080                1085

Lys Val Val Ala Leu Arg Ser Gln Ala Ile Ala Ala Glu Leu Ser Gly
    1090                1095                1100

Arg Gly Gly Met Ala Ser Val Ala Leu Gly Glu Asp Asp Val Val Ser
1105                1110                1115                1120

Arg Leu Val Asp Gly Val Glu Val Ala Ala Val Asn Gly Pro Ser Ser
                1125                1130                1135

Val Val Ile Ala Gly Asp Ala His Ala Leu Asp Ala Thr Leu Glu Ile
        1140                1145                1150

Leu Ser Gly Glu Gly Ile Arg Val Arg Arg Val Ala Val Asp Tyr Ala
    1155                1160                1165

Ser His Thr Arg His Val Glu Asp Ile Arg Asp Thr Leu Ala Glu Thr
    1170                1175                1180

Leu Ala Gly Ile Ser Ala Gln Ala Pro Ala Val Pro Phe Tyr Ser Thr
1185                1190                1195                1200

Val Thr Ser Glu Trp Val Arg Asp Ala Gly Val Leu Asp Gly Gly Tyr
                1205                1210                1215

Trp Tyr Arg Asn Leu Arg Asn Gln Val Arg Phe Gly Ala Ala Ala Thr
                1220                1225                1230

Ala Leu Leu Glu Gln Gly His Thr Val Phe Val Glu Val Ser Ala His
        1235                1240                1245

Pro Val Thr Val Gln Pro Leu Ser Glu Leu Thr Gly Asp Ala Ile Gly
    1250                1255                1260

Thr Leu Arg Arg Glu Asp Gly Gly Leu Arg Arg Leu Leu Ala Ser Met
1265                1270                1275                1280

Gly Glu Leu Phe Val Arg Gly Ile Asp Val Asp Trp Thr Ala Met Val
                1285                1290                1295

Pro Ala Ala Gly Trp Val Asp Leu Pro Thr Tyr Ala Phe Glu His Arg
                1300                1305                1310

His Tyr Trp Leu Glu Pro Ala Glu Pro Ala Ser Ala Gly Asp Pro Leu
        1315                1320                1325

Leu Gly Thr Val Val Ser Thr Pro Gly Ser Asp Arg Leu Thr Ala Val
    1330                1335                1340

Ala Gln Trp Ser Arg Arg Ala Gln Pro Trp Ala Val Asp Gly Leu Val
1345                1350                1355                1360

Pro Asn Ala Ala Leu Val Glu Ala Ala Ile Arg Leu Gly Asp Leu Ala
                1365                1370                1375

Gly Thr Pro Val Val Gly Glu Leu Val Val Asp Ala Pro Val Val Leu
                1380                1385                1390

Pro Arg Arg Gly Ser Arg Glu Val Gln Leu Ile Val Gly Glu Pro Gly
        1395                1400                1405

Glu Gln Arg Arg Arg Pro Ile Glu Val Phe Ser Arg Glu Ala Asp Glu
```

-continued

```
            1410                1415                1420
Pro Trp Thr Arg His Ala His Gly Thr Leu Ala Pro Ala Ala Ala
1425                1430                1435                1440

Val Pro Glu Pro Ala Ala Ala Gly Asp Ala Thr Asp Val Thr Val Ala
                1445                1450                1455

Gly Leu Arg Asp Ala Asp Arg Tyr Gly Ile His Pro Ala Leu Leu Asp
                1460                1465                1470

Ala Ala Val Arg Thr Val Val Gly Asp Leu Leu Pro Ser Val Trp
            1475                1480                1485

Thr Gly Val Ser Leu Leu Ala Ser Gly Ala Thr Ala Val Thr Val Thr
            1490                1495                1500

Pro Thr Ala Thr Gly Leu Arg Leu Thr Asp Pro Ala Gly Gln Pro Val
1505                1510                1515                1520

Leu Thr Val Glu Ser Val Arg Gly Thr Pro Phe Val Ala Glu Gln Gly
                1525                1530                1535

Thr Thr Asp Ala Leu Phe Arg Val Asp Trp Pro Glu Ile Pro Leu Pro
            1540                1545                1550

Thr Ala Glu Thr Ala Asp Phe Leu Pro Tyr Glu Ala Thr Ser Ala Glu
            1555                1560                1565

Ala Thr Leu Ser Ala Leu Gln Ala Trp Leu Ala Asp Pro Ala Glu Thr
            1570                1575                1580

Arg Leu Ala Val Val Thr Gly Asp Cys Thr Glu Pro Gly Ala Ala Ala
1585                1590                1595                1600

Ile Trp Gly Leu Val Arg Ser Ala Gln Ser Glu His Pro Gly Arg Ile
                1605                1610                1615

Val Leu Ala Asp Leu Asp Asp Pro Ala Val Leu Pro Ala Val Val Ala
                1620                1625                1630

Ser Gly Glu Pro Gln Val Arg Val Arg Asn Gly Val Ala Ser Val Pro
            1635                1640                1645

Arg Leu Thr Arg Val Thr Pro Arg Gln Asp Ala Arg Pro Leu Asp Pro
            1650                1655                1660

Glu Gly Thr Val Leu Ile Thr Gly Gly Thr Gly Thr Leu Gly Ala Leu
1665                1670                1675                1680

Thr Ala Arg His Leu Val Thr Ala His Gly Val Arg His Leu Val Leu
                1685                1690                1695

Val Ser Arg Arg Gly Glu Ala Pro Glu Leu Gln Glu Glu Leu Thr Ala
            1700                1705                1710

Leu Gly Ala Ser Val Ala Ile Ala Ala Cys Asp Val Ala Asp Arg Ala
            1715                1720                1725

Gln Leu Glu Ala Val Leu Arg Ala Ile Pro Ala Glu His Pro Leu Thr
            1730                1735                1740

Ala Val Ile His Thr Ala Gly Val Leu Asp Asp Gly Val Val Thr Glu
1745                1750                1755                1760

Leu Thr Pro Asp Arg Leu Ala Thr Val Arg Arg Pro Lys Val Asp Ala
                1765                1770                1775

Ala Arg Leu Leu Asp Glu Leu Thr Arg Glu Ala Asp Leu Ala Ala Phe
            1780                1785                1790

Val Leu Phe Ser Ser Ala Ala Gly Val Leu Gly Asn Pro Gly Gln Ala
            1795                1800                1805

Gly Tyr Ala Ala Ala Asn Ala Glu Leu Asp Ala Leu Ala Arg Gln Arg
            1810                1815                1820

Asn Ser Leu Asp Leu Pro Ala Val Ser Ile Ala Trp Gly Tyr Trp Ala
1825                1830                1835                1840
```

```
Thr Val Ser Gly Met Thr Glu His Leu Gly Asp Ala Asp Leu Arg Arg
                1845                1850                1855

Asn Gln Arg Ile Gly Met Ser Gly Leu Pro Ala Asp Glu Gly Met Ala
                1860                1865                1870

Leu Leu Asp Ala Ala Ile Ala Thr Gly Gly Thr Leu Val Ala Ala Lys
                1875                1880                1885

Phe Asp Val Ala Ala Leu Arg Ala Thr Ala Lys Ala Gly Gly Pro Val
    1890                1895                1900

Pro Pro Leu Leu Arg Gly Leu Ala Pro Leu Pro Arg Arg Ala Ala Ala
1905                1910                1915                1920

Lys Thr Ala Ser Leu Thr Glu Arg Leu Ala Gly Leu Ala Glu Thr Glu
                1925                1930                1935

Gln Ala Ala Ala Leu Leu Asp Leu Val Arg Arg His Ala Ala Glu Val
                1940                1945                1950

Leu Gly His Ser Gly Ala Glu Ser Val His Ser Gly Arg Thr Phe Lys
                1955                1960                1965

Asp Ala Gly Phe Asp Ser Leu Thr Ala Val Glu Leu Arg Asn Arg Leu
    1970                1975                1980

Ala Ala Ala Thr Gly Leu Thr Leu Ser Pro Ala Met Ile Phe Asp Tyr
1985                1990                1995                2000

Pro Lys Pro Pro Ala Leu Ala Asp His Leu Arg Ala Lys Leu Phe Gly
                2005                2010                2015

Ser Ala Ala Asn Arg Pro Ala Glu Ile Gly Thr Ala Ala Ala Glu Glu
                2020                2025                2030

Pro Ile Ala Ile Val Ala Met Ala Cys Arg Phe Pro Gly Gly Val His
                2035                2040                2045

Ser Pro Glu Asp Leu Trp Arg Leu Val Ala Asp Gly Ala Asp Ala Val
                2050                2055                2060

Thr Glu Phe Pro Ala Asp Arg Gly Trp Asp Thr Asp Arg Leu Tyr His
2065                2070                2075                2080

Glu Asp Pro Asp His Glu Gly Thr Thr Tyr Val Arg His Gly Ala Phe
                2085                2090                2095

Leu Asp Asp Ala Ala Gly Phe Asp Ala Ala Phe Phe Gly Ile Ser Pro
                2100                2105                2110

Asn Glu Ala Leu Ala Met Asp Pro Gln Gln Arg Leu Leu Leu Glu Thr
                2115                2120                2125

Ser Trp Glu Leu Phe Glu Arg Ala Ala Ile Asp Pro Thr Thr Leu Ala
                2130                2135                2140

Gly Gln Asp Ile Gly Val Phe Ala Gly Val Asn Ser His Asp Tyr Ser
2145                2150                2155                2160

Met Arg Met His Arg Ala Ala Gly Val Glu Gly Phe Arg Leu Thr Gly
                2165                2170                2175

Gly Ser Ala Ser Val Leu Ser Gly Arg Val Ala Tyr His Phe Gly Val
                2180                2185                2190

Glu Gly Pro Ala Val Thr Val Asp Thr Ala Cys Ser Ser Ser Leu Val
    2195                2200                2205

Ala Leu His Met Ala Val Gln Ala Leu Gln Arg Gly Glu Cys Ser Met
    2210                2215                2220

Ala Leu Ala Gly Gly Val Met Val Met Gly Thr Val Glu Thr Phe Val
2225                2230                2235                2240

Glu Phe Ser Arg Gln Arg Gly Leu Ala Pro Asp Gly Arg Cys Lys Ala
                2245                2250                2255
```

```
Phe Ala Asp Gly Ala Asp Gly Thr Gly Trp Ser Glu Gly Val Gly Leu
            2260                2265                2270

Leu Leu Val Glu Arg Leu Ser Glu Ala Gln Arg Arg Gly His Gln Val
        2275                2280                2285

Leu Ala Val Val Arg Gly Ser Ala Val Asn Ser Asp Gly Ala Ser Asn
            2290                2295                2300

Gly Leu Thr Ala Pro Asn Gly Pro Ser Gln Gln Arg Val Ile Arg Lys
2305                2310                2315                2320

Ala Leu Ala Ala Ala Gly Leu Ser Thr Ser Asp Val Asp Ala Val Glu
            2325                2330                2335

Ala His Gly Thr Gly Thr Thr Leu Gly Asp Pro Ile Glu Ala Glu Ala
            2340                2345                2350

Leu Leu Ala Thr Tyr Gly Gln Asn Arg Glu Thr Pro Leu Trp Leu Gly
            2355                2360                2365

Ser Val Lys Ser Asn Leu Gly His Thr Gln Ala Ala Ala Gly Val Ala
        2370                2375                2380

Gly Val Ile Lys Met Val Met Ala Met Arg His Gly Val Leu Pro Arg
2385                2390                2395                2400

Thr Leu His Val Asp Arg Pro Ser Ser Tyr Val Asp Trp Ser Ala Gly
            2405                2410                2415

Ala Val Glu Leu Leu Thr Glu Ala Arg Asp Trp Val Ser Asn Gly His
        2420                2425                2430

Pro Arg Arg Ala Gly Val Ser Ser Phe Gly Ile Gly Gly Thr Asn Ala
            2435                2440                2445

His Val Val Leu Glu Glu Val Ala Ala Pro Ile Thr Thr Pro Gln Pro
        2450                2455                2460

Glu Pro Ala Glu Phe Leu Val Pro Val Leu Val Ser Ala Arg Thr Ala
2465                2470                2475                2480

Ala Gly Leu Arg Gly Gln Ala Gly Arg Leu Ala Ala Phe Leu Gly Asp
            2485                2490                2495

Arg Thr Asp Val Arg Val Pro Asp Ala Ala Tyr Ala Leu Ala Thr Thr
            2500                2505                2510

Arg Ala Gln Leu Asp His Arg Ala Val Val Leu Ala Ser Asp Arg Ala
        2515                2520                2525

Gln Leu Cys Ala Asp Leu Ala Ala Phe Gly Ser Gly Val Val Thr Gly
        2530                2535                2540

Thr Pro Val Asp Gly Lys Leu Ala Val Leu Phe Thr Gly Gln Gly Ser
2545                2550                2555                2560

Gln Trp Ala Gly Met Gly Arg Glu Leu Ala Glu Thr Phe Pro Val Phe
            2565                2570                2575

Arg Asp Ala Phe Glu Ala Ala Cys Glu Ala Val Asp Thr His Leu Arg
            2580                2585                2590

Glu Arg Pro Leu Arg Glu Val Val Phe Asp Asp Ser Ala Leu Leu Asp
        2595                2600                2605

Gln Thr Met Tyr Thr Gln Gly Ala Leu Phe Ala Val Glu Thr Ala Leu
        2610                2615                2620

Phe Arg Leu Phe Glu Ser Trp Gly Val Arg Pro Gly Leu Leu Ala Gly
2625                2630                2635                2640

His Ser Ile Gly Glu Leu Ala Ala Ala His Val Ser Gly Val Leu Asp
            2645                2650                2655

Leu Ala Asp Ala Gly Glu Leu Val Ala Ala Arg Gly Arg Leu Met Gln
            2660                2665                2670

Ala Leu Pro Ala Gly Gly Ala Met Val Ala Val Gln Ala Thr Glu Asp
```

-continued

```
                2675                2680                2685
Glu Val Ala Pro Leu Leu Asp Gly Thr Val Cys Val Ala Ala Val Asn
    2690                2695                2700
Gly Pro Asp Ser Val Val Leu Ser Gly Thr Glu Ala Ala Val Leu Ala
2705                2710                2715                2720
Val Ala Asp Glu Leu Ala Gly Arg Gly Arg Lys Thr Arg Arg Leu Ala
            2725                2730                2735
Val Ser His Ala Phe His Ser Pro Leu Met Glu Pro Met Leu Asp Asp
            2740                2745                2750
Phe Arg Ala Val Ala Glu Arg Leu Thr Tyr Arg Ala Gly Ser Leu Pro
            2755                2760                2765
Val Val Ser Thr Leu Thr Gly Glu Leu Ala Ala Leu Asp Ser Pro Asp
    2770                2775                2780
Tyr Trp Val Gly Gln Val Arg Asn Ala Val Arg Phe Ser Asp Ala Val
2785                2790                2795                2800
Thr Ala Leu Gly Ala Gln Gly Ala Ser Thr Phe Leu Glu Leu Gly Pro
            2805                2810                2815
Gly Gly Ala Leu Ala Ala Met Ala Leu Gly Thr Leu Gly Gly Pro Glu
            2820                2825                2830
Gln Ser Cys Val Ala Thr Leu Arg Lys Asn Gly Ala Glu Val Pro Asp
            2835                2840                2845
Val Leu Thr Ala Leu Ala Glu Leu His Val Arg Gly Val Gly Val Asp
            2850                2855                2860
Trp Thr Thr Val Leu Asp Glu Pro Ala Thr Ala Val Gly Thr Val Leu
2865                2870                2875                2880
Pro Thr Tyr Ala Phe Gln His Gln Arg Phe Trp Val Asp Val Asp Glu
            2885                2890                2895
Thr Ala Ala Val Ser Val Thr Pro Pro Ala Glu Pro Ile Val Asp
            2900                2905                2910
Arg Pro Val Gln Asp Val Leu Glu Leu Val Arg Glu Ser Ala Ala Val
            2915                2920                2925
Val Leu Gly His Arg Asp Ala Gly Ser Phe Asp Leu Asp Arg Ser Phe
            2930                2935                2940
Lys Asp His Gly Phe Asp Ser Leu Ser Ala Val Lys Leu Arg Asn Arg
2945                2950                2955                2960
Leu Arg Asp Phe Thr Gly Val Glu Leu Pro Ser Thr Leu Ile Phe Asp
            2965                2970                2975
Tyr Pro Asn Pro Ala Val Leu Ala Asp His Leu Arg Ala Glu Leu Leu
            2980                2985                2990
Gly Glu Arg Pro Ala Ala Pro Ala Pro Val Thr Arg Asp Val Ser Asp
            2995                3000                3005
Glu Pro Ile Ala Ile Val Gly Met Ser Thr Arg Leu Pro Gly Gly Ala
    3010                3015                3020
Asp Ser Pro Glu Glu Leu Trp Lys Leu Val Ala Glu Gly Arg Asp Ala
3025                3030                3035                3040
Val Ser Gly Phe Pro Val Asp Arg Gly Trp Asp Leu Asp Gly Leu Tyr
            3045                3050                3055
His Pro Asp Pro Ala His Ala Gly Thr Ser Tyr Thr Arg Ser Gly Gly
            3060                3065                3070
Phe Leu His Asp Ala Ala Gln Phe Asp Ala Gly Leu Phe Gly Ile Ser
            3075                3080                3085
Pro Arg Glu Ala Leu Ala Met Asp Pro Gln Gln Arg Leu Leu Leu Glu
    3090                3095                3100
```

-continued

```
Thr Ser Trp Glu Ala Leu Glu Arg Ala Gly Val Asp Pro Leu Ser Ala
3105                3110                3115                3120

Arg Gly Ser Asp Val Gly Val Phe Thr Gly Ile Val His His Asp Tyr
            3125                3130                3135

Val Thr Arg Leu Arg Glu Val Pro Glu Asp Val Gln Gly Tyr Thr Met
            3140                3145                3150

Thr Gly Thr Ala Ser Ser Val Ala Ser Gly Arg Val Ala Tyr Val Phe
            3155                3160                3165

Gly Phe Glu Gly Pro Ala Val Thr Val Asp Thr Ala Cys Ser Ser Ser
            3170                3175                3180

Leu Val Ala Met His Leu Ala Ala Gln Ala Leu Arg Gln Gly Glu Cys
3185                3190                3195                3200

Ser Met Ala Leu Ala Gly Gly Ala Thr Val Met Ala Ser Pro Asp Ala
            3205                3210                3215

Phe Leu Glu Phe Ser Arg Gln Arg Gly Leu Ser Ala Asp Gly Arg Cys
            3220                3225                3230

Lys Ala Tyr Ala Glu Gly Ala Asp Gly Thr Gly Trp Ala Glu Gly Val
            3235                3240                3245

Gly Val Val Leu Glu Arg Leu Ser Val Ala Arg Glu Arg Gly His
            3250                3255                3260

Arg Val Leu Ala Val Leu Arg Gly Ser Ala Val Asn Gln Asp Gly Ala
3265                3270                3275                3280

Ser Asn Gly Leu Thr Ala Pro Asn Gly Pro Ser Gln Gln Arg Val Ile
            3285                3290                3295

Arg Gly Ala Leu Ala Ser Ala Gly Leu Ala Pro Ser Asp Val Asp Val
            3300                3305                3310

Val Glu Gly His Gly Thr Gly Thr Ala Leu Gly Asp Pro Ile Glu Val
            3315                3320                3325

Gln Ala Leu Leu Ala Thr Tyr Gly Gln Glu Arg Glu Gln Pro Leu Trp
            3330                3335                3340

Leu Gly Ser Leu Lys Ser Asn Leu Gly His Thr Gln Ala Ala Ala Gly
3345                3350                3355                3360

Val Val Gly Val Ile Lys Met Ile Met Ala Met Arg His Gly Val Met
            3365                3370                3375

Pro Ala Thr Leu His Val Asp Glu Arg Thr Ser Gln Val Asp Trp Ser
            3380                3385                3390

Ala Gly Ala Ile Glu Val Leu Thr Glu Ala Arg Glu Trp Pro Arg Thr
            3395                3400                3405

Gly Arg Pro Arg Arg Ala Gly Val Ser Ser Phe Gly Ala Ser Gly Thr
            3410                3415                3420

Asn Ala His Leu Ile Ile Glu Glu Gly Pro Ala Glu Glu Ala Val Asp
3425                3430                3435                3440

Glu Glu Val Ala Ser Val Pro Leu Val Val Ser Ala Arg Ser Ala
            3445                3450                3455

Gly Ser Leu Ala Gly Gln Ala Gly Arg Leu Ala Ala Val Leu Glu Asn
            3460                3465                3470

Glu Ser Leu Ala Gly Val Ala Gly Ala Leu Val Ser Gly Arg Ala Thr
            3475                3480                3485

Leu Asn Glu Arg Ala Val Val Ile Ala Gly Ser Arg Asp Glu Ala Gln
            3490                3495                3500

Asp Gly Leu Gln Ala Leu Ala Arg Gly Glu Asn Ala Pro Gly Val Val
3505                3510                3515                3520
```

-continued

```
Thr Gly Thr Ala Gly Lys Pro Gly Lys Val Val Trp Val Phe Pro Gly
            3525                3530                3535

Gln Gly Ser Gln Trp Met Gly Met Gly Arg Asp Leu Leu Asp Ser Ser
            3540                3545                3550

Pro Val Phe Ala Ala Arg Ile Lys Glu Cys Ala Ala Ala Leu Glu Gln
            3555                3560                3565

Trp Thr Asp Trp Ser Leu Leu Asp Val Leu Arg Gly Asp Ala Asp Leu
            3570                3575                3580

Leu Asp Arg Val Asp Val Val Gln Pro Ala Ser Phe Ala Met Met Val
3585                3590                3595                3600

Gly Leu Ala Ala Val Trp Thr Ser Leu Gly Val Thr Pro Asp Ala Val
            3605                3610                3615

Leu Gly His Ser Gln Gly Glu Ile Ala Ala Ala Cys Val Ser Gly Ala
            3620                3625                3630

Leu Ser Leu Asp Asp Ala Ala Lys Val Val Ala Leu Arg Ser Gln Ala
            3635                3640                3645

Ile Ala Gly Glu Leu Ala Gly Arg Gly Gly Met Ala Ser Val Ala Leu
            3650                3655                3660

Ser Glu Glu Asp Ala Val Ala Arg Leu Thr Pro Trp Ala Asn Arg Val
3665                3670                3675                3680

Glu Val Ala Ala Val Asn Ser Pro Ser Ser Val Val Ile Ala Gly Asp
            3685                3690                3695

Ala Gln Ala Leu Asp Glu Ala Leu Glu Ala Leu Ala Gly Asp Gly Val
            3700                3705                3710

Arg Val Arg Arg Val Ala Val Asp Tyr Ala Ser His Thr Arg His Val
            3715                3720                3725

Glu Ala Ile Ala Glu Thr Leu Ala Lys Thr Leu Ala Gly Ile Asp Ala
            3730                3735                3740

Arg Val Pro Ala Ile Pro Phe Tyr Ser Thr Val Leu Gly Thr Trp Ile
3745                3750                3755                3760

Glu Gln Ala Val Val Asp Ala Gly Tyr Trp Tyr Arg Asn Leu Arg Gln
            3765                3770                3775

Gln Val Arg Phe Gly Pro Ser Val Ala Asp Leu Ala Gly Leu Gly His
            3780                3785                3790

Thr Val Phe Val Glu Ile Ser Ala His Pro Val Leu Val Gln Pro Leu
            3795                3800                3805

Ser Glu Ile Ser Asp Asp Ala Val Val Thr Gly Ser Leu Arg Arg Asp
            3810                3815                3820

Asp Gly Gly Leu Arg Arg Leu Leu Ala Ser Ala Ala Glu Leu Tyr Val
3825                3830                3835                3840

Arg Gly Val Ala Val Asp Trp Thr Ala Ala Val Pro Ala Ala Gly Trp
            3845                3850                3855

Val Asp Leu Pro Thr Tyr Ala Phe Asp Arg Arg His Phe Trp Leu His
            3860                3865                3870

Glu Ala Glu Thr Ala Glu Ala Ala Glu Gly Met Asp Gly Glu Phe Trp
            3875                3880                3885

Thr Ala Ile Glu Gln Ser Asp Val Asp Ser Leu Ala Glu Leu Leu Glu
            3890                3895                3900

Leu Val Pro Glu Gln Arg Gly Ala Leu Ser Thr Val Val Pro Val Leu
3905                3910                3915                3920

Ala Gln Trp Arg Asp Arg Arg Glu Arg Ser Thr Ala Glu Lys Leu
            3925                3930                3935

Arg Tyr Gln Val Thr Trp Gln Pro Leu Glu Arg Glu Ala Ala Gly Val
```

-continued

```
              3940              3945              3950
Pro Gly Gly Arg Trp Leu Ala Val Val Pro Ala Gly Thr Thr Asp Ala
        3955              3960              3965
Leu Leu Lys Glu Leu Thr Gly Gln Gly Leu Asp Ile Val Arg Leu Glu
        3970              3975              3980
Ile Glu Glu Ala Ser Arg Ala Gln Leu Ala Glu Gln Leu Arg Asn Val
3985              3990              3995              4000
Leu Ala Glu His Asp Leu Thr Gly Val Leu Ser Leu Ala Leu Asp
              4005              4010              4015
Gly Gly Pro Ala Asp Ala Ala Glu Ile Thr Ala Ser Thr Leu Ala Leu
        4020              4025              4030
Val Gln Ala Leu Gly Asp Thr Thr Thr Ser Ala Pro Leu Trp Cys Leu
        4035              4040              4045
Thr Ser Gly Ala Val Asn Ile Gly Ile Gln Asp Ala Val Thr Ala Pro
        4050              4055              4060
Ala Gln Ala Ala Val Trp Gly Leu Gly Arg Ala Val Ala Leu Glu Arg
4065              4070              4075              4080
Leu Asp Arg Trp Gly Gly Leu Val Asp Leu Pro Ala Ala Ile Asp Ala
              4085              4090              4095
Arg Thr Ala Gln Ala Leu Leu Gly Val Leu Asn Gly Ala Ala Gly Glu
        4100              4105              4110
Asp Gln Leu Ala Val Arg Arg Ser Gly Val Tyr Arg Arg Leu Val
        4115              4120              4125
Arg Lys Pro Val Pro Glu Ser Ala Thr Ser Arg Trp Glu Pro Arg Gly
        4130              4135              4140
Thr Val Leu Val Thr Gly Gly Ala Glu Gly Leu Gly Arg His Ala Ser
4145              4150              4155              4160
Val Trp Leu Ala Gln Ser Gly Ala Glu Arg Leu Ile Val Thr Gly Thr
              4165              4170              4175
Asp Gly Val Asp Glu Leu Thr Ala Glu Leu Ala Glu Phe Gly Thr Thr
              4180              4185              4190
Val Glu Phe Cys Ala Asp Thr Asp Arg Asp Ala Ile Ala Gln Leu Val
        4195              4200              4205
Ala Asp Ser Glu Val Thr Ala Val His Ala Ala Asp Ile Ala Gln
        4210              4215              4220
Thr Ser Ser Val Asp Asp Thr Gly Val Ala Asp Leu Asp Glu Val Phe
4225              4230              4235              4240
Ala Ala Lys Val Thr Thr Ala Val Trp Leu Asp Gln Leu Phe Glu Asp
              4245              4250              4255
Thr Pro Leu Asp Ala Phe Val Val Phe Ser Ser Ile Ala Gly Ile Trp
              4260              4265              4270
Gly Gly Gly Gly Gln Gly Pro Ala Gly Ala Asn Ala Val Leu Asp
        4275              4280              4285
Ala Leu Val Glu Trp Arg Arg Ala Arg Gly Leu Lys Ala Thr Ser Ile
        4290              4295              4300
Ala Trp Gly Ala Leu Asp Gln Ile Gly Ile Gly Met Asp Glu Ala Ala
4305              4310              4315              4320
Leu Ala Gln Leu Arg Arg Arg Gly Val Ile Pro Met Ala Pro Pro Leu
              4325              4330              4335
Ala Val Thr Ala Met Val Gln Ala Val Ala Gly Asn Glu Lys Ala Val
              4340              4345              4350
Ala Val Ala Asp Met Asp Trp Ala Ala Phe Ile Pro Ala Phe Thr Ser
        4355              4360              4365
```

-continued

```
Val Arg Pro Ser Pro Leu Phe Ala Asp Leu Pro Glu Ala Lys Ala Ile
    4370                4375                4380

Leu Arg Ala Ala Gln Asp Asp Gly Glu Asp Gly Asp Thr Ala Ser Ser
4385                4390                4395                4400

Leu Ala Asp Ser Leu Arg Ala Val Pro Asp Ala Glu Gln Asn Arg Ile
            4405                4410                4415

Leu Leu Lys Leu Val Arg Gly His Ala Ser Thr Val Leu Gly His Ser
        4420                4425                4430

Gly Ala Glu Gly Ile Gly Pro Arg Gln Ala Phe Gln Glu Val Gly Phe
    4435                4440                4445

Asp Ser Leu Ala Ala Val Asn Leu Arg Asn Ser Leu His Ala Ala Thr
    4450                4455                4460

Gly Leu Arg Leu Pro Ala Thr Leu Ile Phe Asp Tyr Pro Thr Pro Glu
4465                4470                4475                4480

Ala Leu Val Gly Tyr Leu Arg Val Glu Leu Leu Arg Glu Ala Asp Asp
            4485                4490                4495

Gly Leu Asp Gly Arg Glu Asp Asp Leu Arg Arg Val Leu Ala Ala Val
        4500                4505                4510

Pro Phe Ala Arg Phe Lys Glu Ala Gly Val Leu Asp Thr Leu Leu Gly
    4515                4520                4525

Leu Ala Asp Thr Gly Thr Glu Pro Gly Thr Asp Ala Glu Thr Thr Glu
    4530                4535                4540

Ala Ala Pro Ala Ala Asp Asp Ala Glu Leu Ile Asp Ala Leu Asp Ile
4545                4550                4555                4560

Ser Gly Leu Val Gln Arg Ala Leu Gly Gln Thr Ser
            4565                4570

<210> SEQ ID NO 5
<211> LENGTH: 5069
<212> TYPE: PRT
<213> ORGANISM: Amycolatopsis mediterranei

<400> SEQUENCE: 5

Met Ala Asn Gln Ser Trp Arg Lys Asn Met Ser Ala Pro Asn Glu Gln
1               5                   10                  15

Ile Val Asp Ala Leu Arg Ala Ser Leu Lys Glu Asn Val Arg Leu Gln
            20                  25                  30

Gln Glu Asn Ser Ala Leu Ala Ala Ala Ala Glu Pro Val Ala Ile
        35                  40                  45

Val Ser Met Ala Cys Arg Tyr Ala Gly Gly Ile Arg Gly Pro Glu Asp
    50                  55                  60

Phe Trp Arg Val Val Ser Glu Gly Ala Asp Val Tyr Thr Gly Phe Pro
65              70                  75                  80

Glu Asp Arg Gly Trp Asp Val Glu Gly Leu Tyr His Pro Asp Pro Asp
                85                  90                  95

Asn Pro Gly Thr Thr Tyr Val Arg Glu Gly Ala Phe Leu Gln Asp Ala
            100                 105                 110

Ala Gln Phe Asp Ala Gly Phe Phe Gly Ile Ser Pro Arg Glu Ala Leu
        115                 120                 125

Ala Met Asp Pro Gln Gln Arg Gln Leu Leu Glu Val Ser Trp Glu Thr
    130                 135                 140

Leu Glu Arg Ala Gly Ile Asp Pro His Ser Val Arg Gly Ser Asp Ile
145                 150                 155                 160

Gly Val Tyr Ala Gly Val Val His Gln Asp Tyr Ala Pro Asp Leu Ser
```

```
                    165                 170                 175
Gly Phe Glu Gly Phe Met Ser Leu Glu Arg Ala Leu Gly Thr Ala Gly
                180                 185                 190
Gly Val Ala Ser Gly Arg Val Ala Tyr Thr Leu Gly Leu Glu Gly Pro
            195                 200                 205
Ala Val Thr Val Asp Thr Met Cys Ser Ser Leu Val Ala Ile His
        210                 215                 220
Leu Ala Ala Gln Ala Leu Arg Arg Gly Glu Cys Ser Met Ala Leu Ala
225                 230                 235                 240
Gly Gly Ser Thr Val Met Ala Thr Pro Gly Gly Phe Val Gly Phe Ala
                245                 250                 255
Arg Gln Arg Ala Leu Ala Phe Asp Gly Arg Cys Lys Ser Tyr Ala Ala
                260                 265                 270
Ala Ala Asp Gly Ser Gly Trp Ala Glu Gly Val Gly Val Leu Leu Leu
            275                 280                 285
Glu Arg Leu Ser Val Ala Arg Glu Arg Gly His Gln Val Leu Ala Val
        290                 295                 300
Ile Arg Gly Ser Ala Val Asn Gln Asp Gly Ala Ser Asn Gly Leu Thr
305                 310                 315                 320
Ala Pro Asn Gly Pro Ala Gln Gln Arg Val Ile Arg Lys Ala Leu Ala
                325                 330                 335
Ser Ala Gly Leu Thr Pro Ser Asp Val Asp Thr Val Glu Gly His Gly
                340                 345                 350
Thr Gly Thr Val Leu Gly Asp Pro Ile Glu Val Gln Ala Leu Leu Ala
            355                 360                 365
Thr Tyr Gly Gln Gly Arg Asp Pro Gln Gln Pro Leu Trp Leu Gly Ser
        370                 375                 380
Val Lys Ser Val Val Gly His Thr Gln Ala Ala Ser Gly Val Ala Gly
385                 390                 395                 400
Val Ile Lys Met Val Gln Ser Leu Arg His Gly Gln Leu Pro Ala Thr
                405                 410                 415
Gln His Val Asp Ala Pro Thr Pro Gln Val Asp Trp Ser Ala Gly Ala
                420                 425                 430
Ile Glu Leu Leu Ala Glu Gly Arg Glu Trp Pro Arg Asn Gly His Pro
            435                 440                 445
Arg Arg Gly Gly Ile Ser Ser Phe Gly Ala Ser Gly Thr Asn Ala His
        450                 455                 460
Met Ile Leu Glu Glu Ala Pro Glu Asp Glu Pro Val Thr Glu Ala Pro
465                 470                 475                 480
Ala Pro Thr Gly Val Val Pro Leu Val Val Ser Ala Ala Thr Ala Ala
                485                 490                 495
Ser Leu Ala Ala Gln Ala Gly Arg Leu Ala Glu Val Gly Asp Val Ser
                500                 505                 510
Leu Ala Asp Val Ala Gly Thr Leu Val Ser Gly Arg Ala Met Leu Ser
            515                 520                 525
Glu Arg Ala Val Val Ala Gly Ser His Glu Glu Ala Val Thr Gly
        530                 535                 540
Leu Arg Ala Leu Ala Arg Gly Glu Ser Ala Pro Gly Leu Leu Ser Gly
545                 550                 555                 560
Arg Gly Ser Gly Val Pro Gly Lys Val Val Val Phe Pro Gly Gln
                565                 570                 575
Gly Thr Gln Trp Ala Gly Met Gly Arg Glu Leu Leu Asp Ser Ser Glu
                580                 585                 590
```

-continued

```
Val Phe Ala Ala Arg Ile Ala Glu Cys Glu Thr Ala Leu Gly Arg Trp
                595                 600                 605
Val Asp Trp Ser Leu Thr Asp Val Leu Arg Gly Glu Ala Asp Leu Leu
            610                 615                 620
Asp Arg Val Asp Val Val Gln Pro Ala Ser Phe Ala Val Met Val Gly
625                 630                 635                 640
Leu Ala Ala Val Trp Ala Ser Leu Gly Val Glu Pro Glu Ala Val Val
                645                 650                 655
Gly His Ser Gln Gly Glu Ile Ala Ala Cys Val Ser Gly Ala Leu
                660                 665                 670
Ser Leu Glu Asp Ala Ala Lys Val Val Ala Leu Arg Ser Gln Ala Ile
            675                 680                 685
Ala Ala Ser Leu Ala Gly Arg Gly Gly Met Ala Ser Val Ala Leu Ser
            690                 695                 700
Glu Glu Asp Ala Thr Ala Arg Leu Glu Pro Trp Ala Gly Arg Val Glu
705                 710                 715                 720
Val Ala Ala Val Asn Gly Pro Thr Ser Val Val Ile Ala Gly Asp Ala
                725                 730                 735
Glu Ala Leu Asp Glu Ala Leu Asp Ala Leu Asp Asp Gln Gly Val Arg
                740                 745                 750
Ile Arg Arg Val Ala Val Asp Tyr Ala Ser His Thr Arg His Val Glu
            755                 760                 765
Ala Ala Arg Asp Ala Leu Ala Glu Met Leu Gly Gly Ile Arg Ala Gln
            770                 775                 780
Ala Pro Glu Val Pro Phe Tyr Ser Thr Val Thr Gly Gly Trp Val Glu
785                 790                 795                 800
Asp Ala Gly Val Leu Asp Gly Gly Tyr Trp Tyr Arg Asn Leu Arg Arg
                805                 810                 815
Gln Val Arg Phe Gly Pro Ala Val Ala Glu Leu Ile Glu Gln Gly His
            820                 825                 830
Arg Val Phe Val Glu Val Ser Ala His Pro Val Leu Val Gln Pro Ile
            835                 840                 845
Asn Glu Leu Val Asp Asp Thr Glu Ala Val Val Thr Gly Thr Leu Arg
850                 855                 860
Arg Glu Asp Gly Gly Leu Arg Arg Leu Leu Ala Ser Ala Ala Glu Leu
865                 870                 875                 880
Phe Val Arg Gly Val Thr Val Asp Trp Ser Gly Val Leu Pro Pro Ser
                885                 890                 895
Arg Arg Val Glu Leu Pro Thr Tyr Ala Phe Asp His Gln His Tyr Trp
                900                 905                 910
Leu Gln Met Gly Gly Ser Ala Thr Asp Ala Val Ser Leu Gly Leu Ala
            915                 920                 925
Gly Ala Asp His Pro Leu Leu Gly Ala Val Val Pro Leu Pro Gln Ser
            930                 935                 940
Asp Gly Leu Val Phe Thr Ser Arg Leu Ser Leu Lys Ser His Pro Trp
945                 950                 955                 960
Leu Ala Gly His Ala Ile Gly Gly Val Val Leu Ile Pro Gly Thr Val
                965                 970                 975
Tyr Val Asp Leu Ala Leu Arg Ala Gly Asp Glu Leu Gly Phe Gly Val
                980                 985                 990
Leu Glu Glu Leu Val Ile Glu Ala Pro Leu Val Leu Gly Glu Arg Gly
            995                 1000                1005
```

-continued

```
Gly Val Arg Val Gln Val Ala Val Ser Gly Pro Asn Glu Thr Gly Ser
    1010                1015                1020
Arg Ala Val Asp Val Phe Ser Met Arg Glu Asp Gly Asp Glu Trp Thr
1025                1030                1035                1040
Arg His Ala Thr Gly Leu Leu Gly Ala Ser Thr Ser Arg Glu Pro Ser
                1045                1050                1055
Arg Phe Asp Phe Ala Ala Trp Pro Pro Ala Gly Ala Glu Pro Ile Asp
            1060                1065                1070
Val Glu Asn Phe Tyr Thr Asp Leu Thr Glu Arg Gly Tyr Ala Tyr Ser
            1075                1080                1085
Gly Ala Phe Gln Gly Met Arg Ala Val Trp Arg Arg Gly Asp Glu Val
    1090                1095                1100
Phe Ala Glu Val Ala Leu Pro Asp Asp His Arg Glu Asp Ala Gly Lys
1105                1110                1115                1120
Phe Gly Leu His Pro Ala Leu Leu Asp Ala Ala Leu His Thr Asn Ala
                1125                1130                1135
Phe Ala Asn Pro Asp Asp Asp Arg Ser Val Leu Pro Phe Ala Trp Asn
            1140                1145                1150
Gly Leu Val Leu His Ala Val Gly Ala Ser Ala Leu Arg Val Arg Val
        1155                1160                1165
Ala Pro Gly Gly Pro Asp Ala Leu Thr Phe Gln Ala Ala Asp Glu Thr
    1170                1175                1180
Gly Gly Leu Val Val Thr Met Asp Ser Leu Val Ser Arg Glu Val Ser
1185                1190                1195                1200
Ala Ala Gln Leu Glu Thr Ala Ala Gly Glu Glu Arg Asp Ser Leu Phe
                1205                1210                1215
Gln Val Asp Trp Ile Glu Val Pro Ala Thr Glu Thr Ala Ala Thr Glu
            1220                1225                1230
His Ala Glu Val Leu Glu Ala Phe Gly Glu Ala Ala Pro Leu Glu Leu
        1235                1240                1245
Thr Ser Arg Val Leu Glu Ala Val Gln Ser Trp Leu Ala Asp Ala Ala
    1250                1255                1260
Asp Glu Ala Arg Leu Val Val Thr Arg Gly Ala Val Arg Glu Val
1265                1270                1275                1280
Thr Asp Pro Ala Gly Ala Ala Val Trp Gly Leu Val Arg Ala Ala Gln
            1285                1290                1295
Ala Glu Asn Pro Gly Arg Ile Ile Leu Val Asp Thr Asp Gly Asp Val
            1300                1305                1310
Pro Leu Gly Ala Val Leu Ala Ser Gly Glu Pro Gln Leu Ala Val Arg
        1315                1320                1325
Gly Asn Ala Phe Ser Val Pro Arg Leu Ala Arg Ala Thr Gly Glu Val
    1330                1335                1340
Pro Glu Ala Pro Ala Val Phe Ser Pro Glu Gly Thr Val Leu Leu Thr
1345                1350                1355                1360
Gly Gly Thr Gly Ser Leu Gly Gly Leu Val Ala Lys His Leu Val Ala
                1365                1370                1375
Arg His Gly Val Arg Arg Leu Val Leu Ala Ser Arg Arg Gly Val Ala
            1380                1385                1390
Ala Glu Asp Leu Val Thr Glu Leu Thr Glu Gln Gly Ala Thr Val Ser
        1395                1400                1405
Val Val Ala Cys Asp Val Ser Asp Arg Asp Gln Val Ala Ala Leu Leu
    1410                1415                1420
Ala Glu His Arg Pro Thr Gly Ile Val His Leu Ala Gly Leu Leu Asp
```

-continued

```
            1425                1430                1435                1440
Asp Gly Val Ile Gly Ala Leu Asn Arg Glu Arg Leu Ala Gly Val Phe
                    1445                1450                1455
Ala Pro Lys Val Asp Ala Val Gln His Leu Asp Glu Leu Thr Arg Asp
                    1460                1465                1470
Leu Gly Leu Asp Ala Phe Val Val Phe Ser Ser Ala Ala Ala Leu Met
                    1475                1480                1485
Gly Ser Ala Gly Gln Gly Asn Tyr Ala Ala Ala Asn Ala Phe Leu Asp
                    1490                1495                1500
Gly Leu Met Ala Gly Arg Arg Ala Ala Gly Leu Pro Gly Val Ser Leu
1505                1510                1515                1520
Ala Trp Gly Leu Trp Glu Gln Ala Asp Gly Leu Thr Ala Asn Leu Ser
                    1525                1530                1535
Ala Thr Asp Gln Ala Arg Met Ser Arg Gly Gly Val Leu Pro Met Thr
                    1540                1545                1550
Pro Ala Glu Ala Leu Asp Ile Phe Asp Ile Gly Leu Ala Ala Glu Gln
                    1555                1560                1565
Ala Leu Leu Val Pro Ile Lys Leu Asp Leu Arg Thr Leu Arg Gly Gln
                    1570                1575                1580
Ala Thr Ala Gly Gly Glu Val Pro His Leu Leu Arg Gly Leu Val Arg
1585                1590                1595                1600
Ala Ser Arg Arg Val Thr Arg Thr Ala Ala Ala Ser Gly Gly Gly Gly
                    1605                1610                1615
Leu Val His Lys Leu Ala Gly Arg Pro Ala Glu Glu Gln Glu Ala Val
                    1620                1625                1630
Leu Leu Gly Ile Val Gln Ala Glu Ala Ala Val Leu Gly Phe Asn
                    1635                1640                1645
Ala Pro Glu Leu Ala Gln Gly Thr Arg Gly Phe Ser Asp Leu Gly Phe
                    1650                1655                1660
Asp Ser Leu Thr Ala Val Glu Leu Arg Asn Arg Leu Ser Ala Ala Thr
1665                1670                1675                1680
Gly Val Lys Leu Pro Ala Thr Leu Val Phe Asp Tyr Pro Thr Pro Val
                    1685                1690                1695
Ala Leu Ala Arg His Leu Arg Glu Glu Leu Gly Glu Thr Val Ala Gly
                    1700                1705                1710
Ala Pro Ala Thr Pro Val Thr Thr Val Ala Asp Ala Gly Glu Pro Ile
                    1715                1720                1725
Ala Ile Val Gly Met Ala Cys Arg Leu Pro Gly Gly Val Met Ser Pro
                    1730                1735                1740
Asp Asp Leu Trp Arg Met Val Ala Glu Gly Arg Asp Gly Met Ser Pro
1745                1750                1755                1760
Phe Pro Gly Asp Arg Gly Trp Asp Leu Asp Gly Leu Phe Asp Ser Asp
                    1765                1770                1775
Pro Glu Arg Pro Gly Thr Ala Tyr Ile Arg Gln Gly Gly Phe Leu His
                    1780                1785                1790
Glu Ala Ala Leu Phe Asp Pro Gly Phe Phe Gly Ile Ser Pro Arg Glu
                    1795                1800                1805
Ala Leu Ala Met Asp Pro Gln Gln Arg Leu Leu Leu Glu Ala Ser Trp
                    1810                1815                1820
Glu Ala Leu Glu Arg Ala Gly Ile Asp Pro Thr Lys Ala Arg Gly Asp
1825                1830                1835                1840
Ala Val Gly Val Phe Ser Gly Val Ser Ile His Asp Tyr Leu Glu Ser
                    1845                1850                1855
```

-continued

```
Leu Ser Asn Met Pro Ala Glu Leu Glu Gly Phe Val Thr Thr Ala Thr
            1860                1865                1870
Ala Gly Ser Val Ala Ser Gly Arg Val Ser Tyr Thr Phe Gly Phe Glu
        1875                1880                1885
Gly Pro Ala Val Thr Val Asp Thr Ala Cys Ser Ser Ser Leu Val Ala
    1890                1895                1900
Ile His Leu Ala Ala Gln Ala Leu Arg Gln Gly Glu Cys Thr Met Ala
1905                1910                1915                1920
Leu Ala Gly Gly Val Ala Val Met Gly Ser Pro Ile Gly Val Ile Gly
            1925                1930                1935
Met Ser Arg Gln Arg Gly Met Ala Glu Asp Gly Arg Val Lys Ala Phe
        1940                1945                1950
Ala Asp Gly Ala Asp Gly Thr Val Leu Ser Glu Gly Val Gly Ile Val
    1955                1960                1965
Val Leu Glu Arg Leu Ser Val Ala Arg Glu Arg Gly His Arg Val Leu
1970                1975                1980
Ala Val Leu Arg Gly Ser Ala Val Asn Gln Asp Gly Ala Ser Asn Gly
1985                1990                1995                2000
Leu Thr Ala Pro Asn Gly Pro Ser Gln Gln Arg Val Ile Arg Ser Ala
            2005                2010                2015
Leu Ala Gly Ala Gly Leu Gln Pro Ser Glu Val Asp Val Val Glu Ala
        2020                2025                2030
His Gly Thr Gly Thr Ala Leu Gly Glu Pro Ile Glu Ala Gln Ala Leu
    2035                2040                2045
Leu Ala Thr Tyr Gly Lys Ser Arg Glu Thr Pro Leu Trp Leu Gly Ser
    2050                2055                2060
Leu Lys Ser Asn Ile Gly His Thr Gln Ala Ala Ala Gly Val Ala Ala
2065                2070                2075                2080
Val Ile Lys Met Val Gln Ala Leu Arg Gln Asp Thr Leu Pro Pro Thr
            2085                2090                2095
Leu His Val Gln Glu Pro Thr Lys Gln Val Asp Trp Ser Ala Gly Ala
        2100                2105                2110
Val Glu Leu Leu Thr Glu Gly Arg Glu Trp Ala Arg Asn Gly His Pro
    2115                2120                2125
Arg Arg Ala Gly Val Ser Ser Phe Gly Ile Ser Gly Thr Asn Ala His
    2130                2135                2140
Leu Ile Leu Glu Glu Ala Pro Ala Asp Asp Thr Ala Glu Ala Asp Val
2145                2150                2155                2160
Pro Asp Ala Val Val Pro Val Val Ile Ser Ala Arg Ser Thr Gly Ser
            2165                2170                2175
Leu Ala Gly Gln Ala Gly Arg Leu Ala Ala Phe Leu Asp Gly Asp Val
        2180                2185                2190
Pro Leu Thr Arg Val Ala Gly Ala Leu Leu Ser Thr Arg Ala Thr Leu
    2195                2200                2205
Thr Asp Arg Ala Val Val Ala Gly Ser Ala Glu Glu Ala Arg Ala
2210                2215                2220
Gly Leu Thr Ala Leu Ala Arg Gly Glu Ser Ala Ser Gly Leu Val Thr
2225                2230                2235                2240
Gly Thr Ala Gly Met Pro Gly Lys Thr Val Trp Val Phe Pro Gly Gln
            2245                2250                2255
Gly Thr Gln Trp Ala Gly Met Gly Arg Glu Leu Leu Glu Ala Ser Pro
        2260                2265                2270
```

-continued

```
Val Phe Ala Glu Arg Ile Glu Glu Cys Ala Ala Ala Leu Gln Pro Trp
    2275                2280                2285
Ile Asp Trp Ser Leu Leu Asp Val Leu Arg Gly Gly Glu Leu Asp
    2290                2295                2300
Arg Val Asp Val Leu Gln Pro Ala Cys Phe Ala Val Met Val Gly Leu
2305                2310                2315                2320
Ala Ala Val Trp Ala Ser Val Gly Val Pro Asp Ala Val Leu Gly
                2325                2330                2335
His Ser Gln Gly Glu Ile Ala Ala Cys Val Ser Gly Ala Leu Ser
                2340                2345                2350
Leu Glu Asp Ala Ala Lys Val Ala Leu Arg Ser Gln Ala Ile Ala
            2355                2360                2365
Ala Glu Leu Ser Gly Arg Gly Gly Met Ala Ser Ile Gln Leu Ser His
    2370                2375                2380
Asp Glu Val Ala Ala Arg Leu Ala Pro Trp Ala Gly Arg Val Glu Ile
2385                2390                2395                2400
Ala Ala Val Asn Gly Pro Ala Ser Val Val Ile Ala Gly Asp Ala Glu
                2405                2410                2415
Ala Leu Thr Glu Ala Val Glu Val Leu Gly Gly Arg Arg Val Ala Val
                2420                2425                2430
Asp Tyr Ala Ser His Thr Arg His Val Glu Asp Ile Gln Asp Thr Leu
            2435                2440                2445
Ala Glu Thr Leu Ala Gly Ile Asp Ala Gln Ala Pro Val Val Pro Phe
    2450                2455                2460
Tyr Ser Thr Val Ala Gly Glu Trp Ile Thr Asp Ala Gly Val Val Asp
2465                2470                2475                2480
Gly Gly Tyr Trp Tyr Arg Asn Leu Arg Asn Gln Val Gly Phe Gly Pro
                2485                2490                2495
Ala Val Ala Glu Leu Ile Glu Gln Gly His Gly Val Phe Val Glu Val
                2500                2505                2510
Ser Ala His Pro Val Leu Val Gln Pro Ile Ser Glu Leu Thr Asp Ala
            2515                2520                2525
Val Val Thr Gly Thr Leu Arg Arg Asp Asp Gly Gly Val Arg Arg Leu
    2530                2535                2540
Leu Thr Ser Met Ala Glu Leu Phe Val Arg Gly Val Pro Val Asp Trp
2545                2550                2555                2560
Ala Thr Met Ala Pro Pro Ala Arg Val Glu Leu Pro Thr Tyr Ala Phe
                2565                2570                2575
Asp His Gln His Phe Trp Leu Ser Pro Pro Ala Val Ala Asp Ala Pro
            2580                2585                2590
Ala Leu Gly Leu Ala Gly Ala Asp His Pro Leu Leu Gly Ala Val Leu
    2595                2600                2605
Pro Leu Pro Gln Ser Asp Gly Leu Val Phe Thr Ser Arg Leu Ser Val
    2610                2615                2620
Arg Thr His Pro Trp Leu Ala Asp Gly Val Pro Ala Ala Leu Val
2625                2630                2635                2640
Glu Leu Ala Val Arg Ala Gly Asp Glu Ala Gly Cys Pro Val Leu Ala
                2645                2650                2655
Asp Leu Thr Val Glu Lys Leu Leu Val Leu Pro Glu Ser Gly Gly Leu
                2660                2665                2670
Arg Val Gln Val Ile Val Ser Gly Glu Arg Thr Val Glu Val Tyr Ser
            2675                2680                2685
Gln Leu Glu Gly Ala Glu Asp Trp Ile Arg Asn Ala Thr Gly His Leu
```

-continued

```
                2690                2695                2700
Ser Ala Thr Ala Pro Ala His Glu Ala Phe Asp Phe Thr Ala Trp Pro
2705                2710                2715                2720
Pro Ala Gly Ala Gln Gln Val Asp Gly Leu Trp Arg Arg Gly Asp Glu
                2725                2730                2735
Ile Phe Ala Glu Val Ala Leu Pro Glu Glu Leu Asp Ala Gly Ala Phe
                2740                2745                2750
Gly Ile His Pro Phe Leu Leu Asp Ala Val Gln Pro Val Leu Ala
                2755                2760                2765
Asp Asp Glu Gln Pro Ala Glu Trp Arg Ser Leu Val Leu His Ala Ala
                2770                2775                2780
Gly Ala Ser Ala Leu Arg Val Arg Leu Val Pro Gly Ala Leu Gln
2785                2790                2795                2800
Ala Ala Asp Glu Thr Gly Gly Leu Val Leu Thr Ala Asp Ser Val Ala
                2805                2810                2815
Gly Arg Glu Leu Ser Ala Gly Lys Thr Arg Ala Gly Ser Leu Tyr Arg
                2820                2825                2830
Val Asp Trp Thr Glu Val Ser Ile Ala Asp Ser Ala Val Pro Ala Asn
                2835                2840                2845
Ile Glu Val Val Glu Ala Phe Gly Glu Glu Pro Leu Glu Leu Thr Gly
                2850                2855                2860
Arg Val Leu Glu Ala Val Gln Thr Trp Leu Val Thr Ala Ala Asp Asp
2865                2870                2875                2880
Ala Arg Leu Val Val Val Thr Arg Gly Ala Val Arg Glu Val Thr Asp
                2885                2890                2895
Pro Ala Gly Ala Ala Val Trp Gly Leu Val Arg Ala Ala Gln Ala Glu
                2900                2905                2910
Asn Pro Gly Arg Ile Phe Leu Ile Asp Thr Asp Gly Glu Ile Pro Ala
                2915                2920                2925
Leu Thr Gly Asp Glu Pro Glu Ile Ala Val Arg Gly Gly Lys Phe Phe
                2930                2935                2940
Val Pro Arg Ile Thr Arg Ala Glu Pro Ser Gly Ala Ala Val Phe Arg
2945                2950                2955                2960
Pro Asp Gly Thr Val Leu Ile Ser Gly Ala Gly Ala Leu Gly Leu
                2965                2970                2975
Val Ala Arg Arg Leu Val Glu Arg His Gly Val Arg Lys Leu Val Leu
                2980                2985                2990
Ala Ser Arg Arg Gly Arg Asp Ala Asp Gly Val Ala Asp Leu Val Ala
                2995                3000                3005
Asp Leu Ala Ala Asp Val Ser Val Val Ala Cys Asp Val Ser Asp Arg
                3010                3015                3020
Ala Gln Val Ala Ala Leu Leu Asp Glu His Arg Pro Thr Ala Val Val
3025                3030                3035                3040
His Thr Ala Gly Val Ile Asp Ala Gly Val Ile Glu Thr Leu Asp Arg
                3045                3050                3055
Asp Arg Leu Ala Thr Val Phe Ala Pro Lys Val Asp Ala Val Arg His
                3060                3065                3070
Leu Asp Glu Leu Thr Arg Asp Arg Asp Leu Asp Ala Phe Val Val Tyr
                3075                3080                3085
Ser Ser Val Ser Ala Val Phe Met Gly Ala Gly Ser Gly Ser Tyr Ala
                3090                3095                3100
Ala Ala Asn Ala Phe Leu Asp Gly Leu Met Ala Asn Arg Arg Ala Ala
3105                3110                3115                3120
```

-continued

```
Gly Leu Pro Gly Leu Ser Leu Ala Trp Gly Leu Trp Asp Gln Ser Thr
                3125                3130                3135

Gly Met Ala Ala Gly Thr Asp Glu Ala Thr Arg Ala Arg Met Ser Arg
            3140                3145                3150

Arg Gly Gly Leu Gln Ile Met Thr Gln Ala Glu Gly Met Asp Leu Phe
            3155                3160                3165

Asp Ala Ala Leu Ser Ser Ala Glu Ser Leu Leu Val Pro Ala Lys Leu
            3170                3175                3180

Asp Leu Arg Gly Val Arg Ala Asp Ala Ala Gly Val Val Pro
3185                3190                3195                3200

His Met Leu Arg Gly Leu Val Arg Ala Gly Arg Ala Gln Ala Arg Ala
                3205                3210                3215

Ala Ser Thr Val Asp Asn Gly Leu Ala Gly Arg Leu Ala Gly Leu Ala
                3220                3225                3230

Pro Ala Asp Gln Leu Thr Leu Leu Asp Leu Val Arg Ala Gln Val
            3235                3240                3245

Ala Ala Val Leu Gly His Ala Asp Ala Ser Ala Val Arg Val Asp Thr
            3250                3255                3260

Ala Phe Lys Asp Ala Gly Phe Asp Ser Leu Thr Ala Val Glu Leu Arg
3265                3270                3275                3280

Asn Arg Met Arg Thr Ala Thr Gly Leu Lys Leu Pro Ala Thr Leu Val
                3285                3290                3295

Phe Asp Tyr Pro Asn Pro Gln Ala Leu Ala Arg His Leu Arg Asp Glu
                3300                3305                3310

Leu Gly Gly Ala Ala Gln Thr Pro Val Thr Thr Ala Ala Lys Ala
            3315                3320                3325

Asp Leu Asp Glu Pro Ile Ala Ile Val Gly Met Ala Cys Arg Leu Pro
            3330                3335                3340

Gly Gly Val Ala Gly Pro Glu Asp Leu Trp Arg Leu Val Ala Glu Gly
3345                3350                3355                3360

Arg Asp Ala Val Ser Ser Phe Pro Thr Asp Arg Gly Trp Asp Thr Asp
            3365                3370                3375

Ser Leu Tyr Asp Pro Asp Pro Ala Arg Pro Gly Lys Thr Tyr Thr Arg
            3380                3385                3390

His Gly Gly Phe Leu His Glu Ala Gly Leu Phe Asp Ala Gly Phe Phe
            3395                3400                3405

Gly Ile Ser Pro Arg Glu Ala Val Ala Met Asp Pro Gln Gln Arg Leu
            3410                3415                3420

Leu Leu Glu Ala Ser Trp Glu Ala Met Glu Asp Ala Gly Val Asp Pro
3425                3430                3435                3440

Leu Ser Leu Lys Gly Asn Asp Val Gly Val Phe Thr Gly Met Phe Gly
                3445                3450                3455

Gln Gly Tyr Val Ala Pro Gly Asp Ser Val Val Thr Pro Glu Leu Glu
            3460                3465                3470

Gly Phe Ala Gly Thr Gly Gly Ser Ser Val Ala Ser Gly Arg Val
            3475                3480                3485

Ser Tyr Val Phe Gly Phe Glu Gly Pro Ala Val Thr Ile Asp Ser Ala
            3490                3495                3500

Cys Ser Ser Ser Leu Val Ala Met His Leu Ala Ala Gln Ser Leu Arg
3505                3510                3515                3520

Gln Gly Glu Cys Ser Met Ala Leu Ala Gly Gly Ala Thr Val Met Ala
                3525                3530                3535
```

```
Asn Pro Gly Ala Phe Val Glu Phe Ser Arg Gln Arg Gly Leu Ala Val
            3540                3545                3550

Asp Gly Arg Cys Lys Ala Phe Ala Ala Ala Asp Gly Thr Gly Trp
            3555                3560                3565

Ala Glu Gly Val Gly Val Ile Leu Glu Arg Leu Ser Val Ala Arg
    3570                3575                3580

Glu Arg Gly His Arg Ile Leu Ala Val Leu Arg Gly Ser Ala Val Asn
3585            3590                3595                3600

Gln Asp Gly Ala Ser Asn Gly Leu Thr Ala Pro Asn Gly Pro Ser Gln
                3605                3610                3615

Gln Arg Val Ile Arg Arg Ala Leu Val Ser Ala Gly Leu Ala Pro Ser
            3620                3625                3630

Asp Val Asp Val Val Glu Ala His Gly Thr Gly Thr Thr Leu Gly Asp
            3635                3640                3645

Pro Ile Glu Ala Gln Ala Leu Leu Ala Thr Tyr Gly Lys Asp Arg Glu
3650                3655                3660

Ser Pro Leu Trp Leu Gly Ser Leu Lys Ser Asn Ile Gly His Ala Gln
3665                3670                3675                3680

Ala Ala Ala Gly Val Ala Gly Val Ile Lys Met Val Gln Ala Leu Arg
            3685                3690                3695

His Glu Val Leu Pro Pro Thr Leu His Val Asp Arg Pro Thr Pro Glu
            3700                3705                3710

Val Asp Trp Ser Ala Gly Ala Val Glu Leu Leu Thr Glu Ala Arg Glu
            3715                3720                3725

Trp Pro Arg Asn Gly Arg Pro Arg Arg Ala Gly Val Ser Ala Phe Gly
            3730                3735                3740

Val Ser Gly Thr Asn Ala His Leu Ile Leu Glu Glu Ala Pro Ala Glu
3745                3750                3755                3760

Glu Pro Val Pro Thr Pro Glu Val Pro Leu Val Pro Val Val Ser
            3765                3770                3775

Ala Arg Ser Arg Ala Ser Leu Ala Gly Gln Ala Gly Arg Leu Ala Gly
            3780                3785                3790

Phe Val Ala Gly Asp Ala Ser Leu Ala Gly Val Ala Arg Ala Leu Val
            3795                3800                3805

Thr Asn Arg Ala Ala Leu Thr Glu Arg Ala Val Met Val Val Gly Ser
            3810                3815                3820

Arg Glu Glu Ala Val Thr Asn Leu Glu Ala Leu Ala Arg Gly Glu Asp
3825                3830                3835                3840

Pro Ala Ala Val Val Thr Gly Arg Ala Gly Ser Pro Gly Lys Leu Val
            3845                3850                3855

Trp Val Phe Pro Gly Gln Gly Ser Gln Trp Ile Gly Met Gly Arg Glu
            3860                3865                3870

Leu Leu Asp Ser Ser Pro Val Phe Ala Glu Arg Val Ala Glu Cys Ala
            3875                3880                3885

Ala Ala Leu Glu Pro Trp Ile Asp Trp Ser Leu Leu Asp Val Leu Arg
            3890                3895                3900

Gly Glu Ser Asp Leu Leu Asp Arg Val Asp Val Val Gln Pro Ala Ser
3905                3910                3915                3920

Phe Ala Met Met Val Gly Leu Ala Ala Val Trp Gln Ser Val Gly Val
                3925                3930                3935

Arg Pro Asp Ala Val Val Gly His Ser Gln Gly Glu Ile Ala Ala Ala
            3940                3945                3950

Cys Val Ser Gly Ala Leu Ser Leu Gln Asp Ala Ala Lys Val Val Ala
```

```
                 3955                3960                3965
Leu Arg Ser Gln Ala Ile Ala Thr Arg Leu Ala Gly Arg Gly Gly Met
    3970                3975                3980

Ala Ser Val Ala Leu Ser Glu Glu Asp Ala Thr Ala Trp Leu Ala Pro
3985                3990                3995                4000

Trp Ala Asp Arg Val Gln Val Ala Ala Val Asn Ser Pro Ala Ser Val
                4005                4010                4015

Val Ile Ala Gly Glu Ala Gln Ala Leu Asp Glu Val Val Asp Ala Leu
                4020                4025                4030

Ser Gly Gln Glu Val Arg Val Arg Arg Val Ala Val Asp Tyr Gly Ser
                4035                4040                4045

His Thr Asn Gln Val Glu Ala Ile Glu Asp Leu Leu Ala Glu Thr Leu
    4050                4055                4060

Ala Gly Ile Glu Ala Gln Ala Pro Lys Val Pro Phe Tyr Ser Thr Leu
4065                4070                4075                4080

Ile Gly Asp Trp Ile Arg Asp Ala Gly Ile Val Asp Gly Gly Tyr Trp
                4085                4090                4095

Tyr Arg Asn Leu Arg Asn Gln Val Gly Phe Gly Pro Ala Val Ala Glu
                4100                4105                4110

Leu Val Arg Gln Gly His Gly Val Phe Val Glu Val Ser Ala His Pro
                4115                4120                4125

Val Leu Val Gln Pro Leu Ser Glu Leu Ser Asp Asp Ala Val Val Thr
                4130                4135                4140

Gly Ser Leu Arg Arg Glu Asp Gly Gly Leu Arg Arg Leu Leu Thr Ser
4145                4150                4155                4160

Met Ala Glu Leu Tyr Val Gln Gly Val Pro Leu Asp Trp Thr Ala Val
                4165                4170                4175

Leu Pro Arg Thr Gly Arg Val Asp Leu Pro Lys Tyr Ala Phe Asp His
                4180                4185                4190

Arg His Tyr Trp Leu Arg Pro Ala Glu Ser Ala Thr Asp Ala Ala Ser
                4195                4200                4205

Leu Gly Gln Ala Ala Ala Asp His Pro Leu Leu Gly Ala Val Val Glu
    4210                4215                4220

Leu Pro Gln Ser Asp Gly Leu Val Phe Thr Ser Arg Leu Ser Val Arg
4225                4230                4235                4240

Thr His Pro Trp Leu Ala Asp His Ala Val Gly Gly Val Val Ile Leu
                4245                4250                4255

Pro Gly Ser Gly Leu Ala Glu Leu Ala Val Arg Ala Gly Asp Glu Ala
                4260                4265                4270

Gly Cys Thr Ala Leu Asp Glu Leu Ile Ile Glu Ala Pro Leu Val Val
                4275                4280                4285

Pro Ala Gln Gly Ala Val Arg Val Gln Val Ala Leu Ser Gly Pro Asp
    4290                4295                4300

Glu Thr Gly Ser Arg Thr Val Asp Leu Tyr Ser Gln Arg Asp Gly Gly
4305                4310                4315                4320

Ala Gly Thr Trp Thr Arg His Ala Thr Gly Val Leu Ser Thr Ala Pro
                4325                4330                4335

Ala Gln Glu Pro Glu Phe Asp Phe His Ala Trp Pro Ala Asp Ala
                4340                4345                4350

Glu Arg Ile Asp Val Glu Thr Phe Tyr Thr Asp Leu Ala Glu Arg Gly
                4355                4360                4365

Tyr Gly Tyr Gly Pro Ala Phe Gln Gly Leu Gln Ala Val Trp Arg Arg
    4370                4375                4380
```

```
                                       -continued

Asp Gly Asp Val Phe Ala Glu Val Ala Leu Pro Glu Asp Leu Arg Lys
4385                4390                4395                4400

Asp Ala Gly Arg Phe Gly Val His Pro Ala Leu Leu Asp Ala Ala Leu
                4405                4410                4415

Gln Ala Ala Thr Ala Val Gly Gly Asp Glu Pro Gly Gln Pro Val Leu
                4420                4425                4430

Ala Phe Ala Trp Asn Gly Leu Val Leu His Ala Gly Ala Ser Ala
                4435                4440                4445

Leu Arg Val Arg Leu Ala Pro Ser Gly Pro Asp Thr Leu Ser Val Ala
                4450                4455                4460

Ala Ala Asp Glu Thr Gly Gly Leu Val Leu Thr Met Glu Ser Leu Val
4465                4470                4475                4480

Ser Arg Pro Val Ser Ala Glu Gln Leu Gly Ala Ala Asp Ala Gly
                4485                4490                4495

His Asp Ala Met Phe Arg Val Asp Trp Thr Glu Leu Pro Ala Val Pro
                4500                4505                4510

Arg Ala Glu Leu Pro Pro Trp Val Arg Ile Asp Thr Ala Asp Val
                4515                4520                4525

Ala Ala Leu Ala Glu Lys Ala Asp Ala Pro Val Val Trp Glu
4530                4535                4540

Ala Ala Gly Gly Asp Pro Ala Leu Ala Val Ser Ser Arg Val Leu Glu
4545                4550                4555                4560

Ile Met Gln Ala Trp Leu Ala Ala Pro Ala Phe Glu Glu Ala Arg Leu
                4565                4570                4575

Val Val Thr Thr Arg Gly Ala Val Pro Ala Gly Gly Asp His Thr Leu
                4580                4585                4590

Thr Asp Pro Ala Ala Ala Val Trp Gly Leu Val Arg Ser Ala Gln
                4595                4600                4605

Ala Glu His Pro Asp Arg Val Val Leu Leu Asp Thr Asp Gly Glu Val
                4610                4615                4620

Pro Leu Gly Ala Val Leu Ala Ser Gly Glu Pro Gln Leu Ala Val Arg
4625                4630                4635                4640

Gly Thr Thr Phe Phe Val Pro Arg Leu Ala Arg Ala Thr Arg Leu Ser
                4645                4650                4655

Asp Ala Pro Pro Ala Phe Asp Pro Asp Gly Thr Val Leu Val Ser Gly
                4660                4665                4670

Ala Gly Ser Leu Gly Thr Leu Val Ala Arg His Leu Val Thr Arg His
                4675                4680                4685

Gly Val Arg Arg Val Val Leu Ala Ser Arg Gln Gly Arg Asp Ala Glu
4690                4695                4700

Gly Ala Gln Asp Leu Ile Thr Glu Leu Thr Gly Glu Gly Ala Asp Val
4705                4710                4715                4720

Ser Phe Val Ala Cys Asp Val Ser Asp Arg Asp Gln Val Ala Ala Leu
                4725                4730                4735

Leu Ala Gly Leu Pro Asp Leu Thr Gly Val His Thr Ala Gly Val
                4740                4745                4750

Phe Glu Asp Gly Val Ile Glu Ala Leu Thr Pro Asp Gln Leu Ala Asn
                4755                4760                4765

Val Tyr Ala Ala Lys Val Thr Ala Ala Met His Leu Asp Glu Leu Thr
                4770                4775                4780

Arg Asp Arg Asp Leu Gly Ala Phe Val Val Phe Ser Ser Val Ala Gly
                4785                4790                4795                4800
```

```
Val Met Gly Gly Gly Gly Gln Gly Pro Tyr Ala Ala Asn Ala Phe
            4805            4810            4815

Leu Asp Ala Ala Met Ala Ser Arg Gln Ala Ala Gly Leu Pro Gly Leu
                4820            4825            4830

Ser Leu Ala Trp Gly Leu Trp Glu Arg Ser Ser Gly Met Ala Ala His
            4835            4840            4845

Leu Ser Glu Val Asp His Ala Arg Ala Ser Arg Asn Gly Val Leu Glu
            4850            4855            4860

Leu Thr Arg Ala Glu Gly Leu Ala Leu Phe Asp Leu Gly Leu Arg Met
4865            4870            4875            4880

Ala Glu Ser Leu Leu Val Pro Ile Lys Leu Asp Leu Ala Ala Met Arg
                4885            4890            4895

Ala Ser Thr Val Pro Val Leu Phe Arg Gly Leu Val Arg Pro Ser Arg
                4900            4905            4910

Thr Gln Ala Arg Thr Ala Ser Thr Val Asp Arg Gly Leu Ala Gly Arg
                4915            4920            4925

Leu Ala Gly Leu Pro Val Ala Glu Arg Ala Val Leu Val Asp Leu
            4930            4935            4940

Val Arg Gly Gln Val Ala Val Leu Gly Tyr Asp Gly Pro Glu Ala
4945            4950            4955            4960

Val Arg Pro Asp Thr Ala Phe Lys Asp Thr Gly Phe Asp Ser Leu Thr
                4965            4970            4975

Ser Val Glu Leu Arg Asn Arg Leu Arg Glu Ala Thr Gly Leu Lys Leu
            4980            4985            4990

Pro Ala Thr Leu Val Phe Asp Tyr Pro Asn Pro Leu Ala Val Ala Arg
            4995            5000            5005

Tyr Leu Gly Ala Arg Leu Val Pro Asp Gly Thr Ala Asn Gly Asn Gly
            5010            5015            5020

Asn Gly Asn Gly His Ser Glu Asp Asp Arg Leu Arg His Ala Leu Ala
5025            5030            5035            5040

Ala Ile Ala Ala Glu Asp Ala Gly Glu Glu Arg Ser Ile Ala Asp Leu
                5045            5050            5055

Gly Val Asp Asp Leu Val Gln Leu Ala Phe Gly Asp Glu
            5060            5065

<210> SEQ ID NO 6
<211> LENGTH: 1721
<212> TYPE: PRT
<213> ORGANISM: Amycolatopsis mediterranei

<400> SEQUENCE: 6

Met Ala Cys Arg Leu Pro Gly Gly Val Thr Gly Pro Gly Asp Leu Trp
1               5                   10                  15

Arg Leu Val Ala Glu Gly Gly Asp Ala Val Ser Gly Phe Pro Thr Asp
                20                  25                  30

Arg Cys Trp Asp Leu Asp Thr Leu Phe Asp Pro Asp Pro Asp His Ala
            35                  40                  45

Gly Thr Ser Tyr Thr Asp Gln Gly Gly Phe Leu His Asp Ala Ala Leu
        50                  55                  60

Phe Asp Pro Gly Phe Phe Gly Ile Ser Pro Arg Glu Ala Leu Ala Met
65                  70                  75                  80

Asp Pro Gln Gln Arg Leu Leu Leu Glu Ala Ser Trp Glu Ala Leu Glu
                85                  90                  95

Gly Val Gly Leu Asp Pro Ala Ser Leu Gln Gly Thr Asp Val Gly Val
            100                 105                 110
```

```
Phe Thr Gly Ala Gly Gly Ser Gly Tyr Gly Gly Gly Leu Thr Gly Pro
            115                 120                 125

Glu Met Gln Ser Phe Ala Gly Thr Gly Leu Ala Ser Ser Val Ala Ser
        130                 135                 140

Gly Arg Val Ser Tyr Val Phe Gly Phe Glu Gly Pro Ala Val Thr Ile
145                 150                 155                 160

Asp Thr Ala Cys Ser Ser Leu Val Ala Met His Leu Ala Ala Gln
                165                 170                 175

Ala Leu Arg Gln Gly Asp Cys Ser Met Ala Leu Ala Gly Gly Ala Met
            180                 185                 190

Val Met Ser Gly Pro Asp Ser Phe Val Val Phe Ser Arg Gln Arg Gly
        195                 200                 205

Leu Ala Thr Asp Gly Arg Cys Lys Ala Phe Ala Ser Gly Ala Asp Gly
            210                 215                 220

Met Val Leu Ala Glu Gly Ile Ser Val Val Leu Glu Arg Leu Ser
225                 230                 235                 240

Val Ala Arg Glu Arg Gly His Arg Val Leu Ala Val Leu Arg Gly Ser
                245                 250                 255

Ala Val Asn Gln Asp Gly Ala Ser Asn Gly Leu Thr Ala Pro Asn Gly
            260                 265                 270

Pro Ser Gln Gln Arg Val Ile Arg Ala Ala Leu Ala Asn Ala Gly Ile
        275                 280                 285

Gly Pro Ser Asp Val Asp Leu Val Glu Ala His Gly Thr Gly Thr Ser
    290                 295                 300

Leu Gly Asp Pro Ile Glu Ala Gln Ala Leu Leu Ala Thr Tyr Gly Gln
305                 310                 315                 320

Asp Arg Glu Thr Pro Leu Trp Leu Gly Ser Leu Lys Ser Asn Ile Gly
                325                 330                 335

His Thr Gln Ala Ala Gly Val Ala Ser Val Ile Lys Val Val Gln
            340                 345                 350

Ala Leu Arg His Gly Val Met Pro Pro Thr Leu His Val Asp Glu Pro
        355                 360                 365

Ser Ser Gln Val Asp Trp Ser Glu Gly Ala Val Glu Leu Leu Thr Gly
    370                 375                 380

Ser Arg Asp Trp Pro Arg Gly Asp Arg Pro Arg Ala Gly Val Ser
385                 390                 395                 400

Ser Phe Gly Val Ser Gly Thr Asn Val His Leu Ile Ile Glu Glu Ala
                405                 410                 415

Pro Glu Glu Pro Ala Ala Ala Val Pro Thr Ser Ala Asp Val Pro
            420                 425                 430

Leu Val Val Ser Ala Arg Ser Thr Gly Ser Leu Ala Gly Gln Ala Asp
        435                 440                 445

Arg Leu Thr Glu Val Asp Val Pro Leu Gly His Leu Ala Gly Ala Leu
    450                 455                 460

Val Ala Gly Arg Ala Val Leu Glu Glu Arg Ala Val Val Ala Gly
465                 470                 475                 480

Ser Ala Glu Glu Ala Arg Ala Gly Leu Gly Ala Leu Ala Arg Gly Glu
                485                 490                 495

Ala Ala Pro Gly Val Val Thr Gly Thr Ala Gly Lys Pro Gly Lys Val
            500                 505                 510

Val Trp Val Phe Pro Gly Gln Gly Thr Gln Trp Val Gly Met Gly Arg
        515                 520                 525
```

-continued

Glu Leu Leu Asp Ala Ser Pro Val Phe Ala Glu Arg Ile Lys Glu Cys
    530                 535                 540

Ala Ala Ala Leu Asp Gln Trp Thr Asp Trp Ser Leu Leu Asp Val Leu
545                 550                 555                 560

Arg Gly Asp Gly Asp Leu Asp Ser Val Glu Val Leu Gln Pro Ala Cys
                565                 570                 575

Phe Ala Val Met Val Gly Leu Ala Ala Val Trp Glu Ser Ala Gly Val
            580                 585                 590

Arg Pro Asp Ala Val Val Gly His Ser Gln Gly Glu Ile Ala Ala Ala
        595                 600                 605

Cys Val Ser Gly Ala Leu Thr Leu Asp Asp Ala Ala Lys Val Val Ala
    610                 615                 620

Leu Arg Ser Gln Ala Ile Ala Ala Arg Leu Ser Gly Arg Gly Gly Met
625                 630                 635                 640

Ala Ser Val Ala Leu Ser Glu Asp Glu Ala Asn Ala Arg Leu Gly Leu
                645                 650                 655

Trp Asp Gly Arg Ile Glu Val Ala Ala Val Asn Gly Pro Ala Ser Val
            660                 665                 670

Val Ile Ala Gly Asp Ala Gln Ala Leu Asp Glu Ala Leu Glu Val Leu
    675                 680                 685

Ala Gly Asp Gly Val Arg Val Arg Gln Val Ala Val Asp Tyr Ala Ser
690                 695                 700

His Thr Arg His Val Glu Asp Ile Arg Asp Thr Leu Ala Glu Thr Leu
705                 710                 715                 720

Ala Gly Ile Thr Ala Gln Ala Pro Asp Val Pro Phe Arg Ser Thr Val
                725                 730                 735

Thr Gly Gly Trp Val Arg Asp Ala Asp Val Leu Asp Gly Gly Tyr Trp
            740                 745                 750

Tyr Arg Asn Leu Arg Asn Gln Val Arg Phe Gly Pro Ala Val Ala Glu
    755                 760                 765

Leu Leu Glu Gln Gly His Gly Val Phe Val Glu Val Ser Ala His Pro
770                 775                 780

Val Leu Val Gln Pro Ile Ser Glu Leu Thr Asp Ala Val Val Thr Gly
785                 790                 795                 800

Thr Leu Arg Arg Asp Asp Gly Gly Leu Arg Arg Leu Leu Thr Ser Met
                805                 810                 815

Ala Glu Leu Phe Val Arg Gly Val Arg Val Asp Trp Ala Thr Leu Val
            820                 825                 830

Pro Pro Ala Arg Val Asp Leu Pro Thr Tyr Ala Phe Asp His Gln His
    835                 840                 845

Phe Trp Leu Arg Pro Ala Ala Gln Ala Asp Ala Val Ser Leu Gly Gln
850                 855                 860

Ala Ala Ala Glu His Pro Leu Leu Gly Ala Val Val Arg Leu Pro Gln
865                 870                 875                 880

Ser Asp Gly Leu Val Phe Thr Ser Arg Leu Ser Leu Arg Thr His Pro
                885                 890                 895

Trp Leu Ala Asp His Thr Ile Gly Gly Val Val Leu Phe Pro Gly Thr
            900                 905                 910

Gly Leu Val Glu Leu Ala Val Arg Ala Gly Asp Glu Ala Gly Cys Pro
    915                 920                 925

Val Leu Asp Glu Leu Val Thr Glu Ala Pro Leu Val Val Pro Gly Gln
930                 935                 940

Gly Gly Val Asn Val Gln Val Thr Val Ser Gly Pro Asp Gln Asn Gly

```
                       945                 950                 955                 960
Leu Arg Thr Val Asp Ile His Ser Gln Arg Asp Asp Val Trp Thr Arg
                    965                 970                 975
His Ala Thr Gly Thr Val Ser Ala Thr Pro Ala Ser Ser Pro Gly Phe
                980                 985                 990
Asp Phe Thr Ala Trp Pro Pro Asp Gly Gln Arg Val Glu Ile Gly
            995                 1000                1005
Asp Phe Tyr Ala Asp Leu Ala Glu Arg Gly Tyr Ala Tyr Gly Pro Leu
        1010                1015                1020
Phe Gln Gly Val Arg Ala Val Trp Gln Arg Gly Glu Asp Val Phe Ala
1025                1030                1035                1040
Glu Val Ala Leu Pro Glu Asp Arg Arg Glu Asp Ala Ala Arg Phe Gly
                1045                1050                1055
Leu His Pro Ala Leu Leu Asp Ala Ala Leu Gln Thr Gly Thr Ile Ala
                1060                1065                1070
Ala Ala Ala Ser Gly Gln Pro Gly Lys Ser Val Met Pro Phe Ser Trp
                1075                1080                1085
Asn Arg Leu Ala Leu His Ala Val Gly Ala Ala Gly Leu Arg Val Arg
            1090                1095                1100
Val Ala Pro Gly Gly Pro Asp Ala Leu Thr Val Glu Ala Ala Asp Glu
1105                1110                1115                1120
Thr Gly Ala Pro Val Leu Thr Met Asp Ser Leu Ile Leu Arg Glu Val
                1125                1130                1135
Ala Leu Asp Gln Leu Asp Thr Ala Arg Ala Gly Ser Leu Tyr Arg Val
            1140                1145                1150
Asp Trp Thr Pro Leu Pro Thr Val Asp Ser Ala Val Pro Ala Gly Arg
            1155                1160                1165
Ala Glu Val Leu Glu Ala Phe Gly Glu Glu Pro Leu Asp Leu Thr Gly
        1170                1175                1180
Arg Val Leu Ala Ala Leu Gln Ala Trp Leu Ser Asp Ala Ala Glu Glu
1185                1190                1195                1200
Ala Arg Leu Val Val Val Thr Arg Gly Ala Val Pro Ala Gly Asp Gly
                1205                1210                1215
Val Val Ser Asp Pro Ala Gly Ala Ala Val Trp Gly Leu Val Arg Ala
                1220                1225                1230
Ala Gln Ala Glu Asn Pro Asp Arg Phe Val Leu Leu Asp Thr Asp Gly
            1235                1240                1245
Glu Val Pro Leu Glu Ala Val Leu Ala Thr Gly Glu Pro Gln Leu Ala
        1250                1255                1260
Leu Arg Gly Thr Thr Phe Ser Val Pro Arg Leu Ala Arg Val Thr Glu
1265                1270                1275                1280
Pro Ala Glu Ala Pro Leu Thr Phe Arg Pro Asp Gly Thr Val Leu Val
            1285                1290                1295
Ser Gly Ala Gly Thr Leu Gly Ala Leu Ala Ala Arg Asp Leu Val Thr
            1300                1305                1310
Arg His Gly Val Arg Arg Leu Val Leu Ala Ser Arg Arg Gly Arg Ala
        1315                1320                1325
Ala Glu Gly Ile Asp Asp Leu Val Ala Glu Leu Thr Gly His Gly Ala
        1330                1335                1340
Glu Val Thr Val Ala Ala Cys Asp Val Ser Asp Arg Asp Gln Val Ala
1345                1350                1355                1360
Ala Leu Leu Lys Glu His Ala Leu Thr Ala Val Val His Thr Ala Gly
                1365                1370                1375
```

```
Val Phe Asp Ala Gly Val Thr Gly Ala Leu Thr Arg Glu Arg Leu Ala
            1380                1385                1390

Lys Val Phe Ala Pro Lys Val Asp Ala Ala Asn His Leu Asp Glu Leu
        1395                1400                1405

Thr Arg Asp Leu Asp Leu Asp Ala Phe Ile Val Tyr Ser Ser Ala Ser
    1410                1415                1420

Ser Ile Phe Met Gly Ala Gly Ser Gly Gly Tyr Ala Ala Ala Asn Ala
1425                1430                1435                1440

Tyr Leu Asp Gly Leu Met Ala Ala Arg Arg Ala Ala Gly Leu Pro Gly
                1445                1450                1455

Leu Ser Leu Ala Trp Gly Pro Trp Glu Gln Leu Thr Gly Met Ala Asp
            1460                1465                1470

Thr Ile Asp Asp Leu Thr Leu Ala Arg Met Ser Arg Arg Glu Gly Arg
        1475                1480                1485

Gly Gly Val Arg Ala Leu Gly Ser Ala Asp Gly Met Glu Leu Phe Asp
    1490                1495                1500

Ala Ala Leu Ala Ala Gly Gln Ala Leu Leu Val Pro Ile Glu Leu Asp
1505                1510                1515                1520

Leu Arg Glu Val Arg Ala Asp Ala Ala Gly Gly Thr Val Pro His
                1525                1530                1535

Leu Leu Arg Gly Leu Val Arg Ala Gly Arg Gln Ala Ala Arg Thr Ala
            1540                1545                1550

Ala Thr Glu Asp Gly Gly Leu Glu Arg Arg Leu Ala Gly Leu Thr Val
        1555                1560                1565

Ala Glu Gln Glu Ala Leu Leu Leu Asp Leu Val Arg Gly Gln Val Ala
    1570                1575                1580

Val Val Leu Gly His Ala Asp Ser Ser Gly Val Arg Ala Asp Ala Ala
1585                1590                1595                1600

Phe Lys Asp Ala Gly Phe Asp Ser Leu Thr Ser Val Glu Leu Arg Asn
                1605                1610                1615

Arg Leu Arg Glu Thr Thr Gly Leu Lys Leu Pro Ala Thr Leu Val Phe
            1620                1625                1630

Asp His Pro Asn Pro Leu Ala Leu Ala Arg His Leu Arg Ala Glu Leu
        1635                1640                1645

Ala Val Asp Glu Ala Ser Pro Ala Asp Ala Val Leu Ala Gly Leu Ala
    1650                1655                1660

Gly Leu Glu Ala Ala Ile Ala Ala Gly Ala Pro Asp Gly Asp Arg
1665                1670                1675                1680

Ile Thr Ala Arg Leu Arg Glu Leu Leu Lys Ala Ala Glu Ala Ala Glu
                1685                1690                1695

Ala Arg Pro Gly Thr Ser Gly Asp Leu Asp Thr Ala Ser Asp Glu Glu
            1700                1705                1710

Leu Phe Ala Leu Val Asp Gly Leu Asp
        1715                1720

<210> SEQ ID NO 7
<211> LENGTH: 1688
<212> TYPE: PRT
<213> ORGANISM: Amycolatopsis mediterranei

<400> SEQUENCE: 7

Met Ala Cys Arg Tyr Pro Gly Gly Val Ser Ser Pro Glu Asp Leu Trp
 1               5                  10                  15

Arg Leu Val Ala Glu Gly Thr Asp Ala Val Ser Ala Phe Pro Gly Asp
```

```
                        20                  25                  30
Arg Gly Trp Asp Val Asp Gly Leu Val Asp Pro Asp Pro Asp Arg Pro
             35                  40                  45

Gly Thr Thr Tyr Thr Asp Gln Gly Gly Phe Leu His Glu Ala Gly Leu
 50                  55                  60

Phe Asp Ala Gly Phe Phe Gly Ile Ser Pro Arg Glu Ala Val Ala Met
 65                  70                  75                  80

Asp Pro Gln Gln Arg Leu Leu Leu Glu Thr Ser Trp Glu Ala Ile Glu
                 85                  90                  95

Arg Thr Gly Thr Asp Pro Leu Ser Leu Lys Gly Ser Asp Ile Gly Val
            100                 105                 110

Phe Thr Gly Val Ala Ser Met Gly Tyr Gly Ala Gly Gly Val Val
            115                 120                 125

Ala Pro Glu Leu Glu Gly Phe Val Gly Thr Gly Ala Ala Pro Cys Ile
            130                 135                 140

Ala Ser Gly Arg Val Ser Tyr Val Leu Gly Phe Glu Gly Pro Ala Val
145                 150                 155                 160

Thr Val Asp Thr Gly Cys Ser Ser Leu Val Ala Met His Leu Ala
                165                 170                 175

Ala Gln Ala Leu Arg Arg Gly Glu Cys Ser Met Ala Leu Ala Gly Gly
            180                 185                 190

Ala Met Val Met Ala Gln Pro Gly Ser Phe Val Ser Phe Ser Arg Gln
            195                 200                 205

Arg Gly Leu Ala Leu Asp Gly Arg Cys Lys Ala Phe Ser Asp Ser Ala
            210                 215                 220

Asp Gly Met Gly Leu Ala Glu Gly Val Gly Val Ile Ala Leu Glu Arg
225                 230                 235                 240

Leu Ser Val Ala Arg Glu Arg Gly His Arg Val Leu Ala Val Leu Arg
                245                 250                 255

Gly Ile Ala Val Asn Gln Asp Gly Ala Ser Asn Gly Leu Thr Ala Pro
            260                 265                 270

Asn Gly Pro Ser Gln Gln Arg Val Ile Arg Ala Ala Leu Ala Glu Ala
            275                 280                 285

Gly Leu Ser Pro Ser Asp Val Asp Ala Val Glu Gly His Gly Thr Gly
            290                 295                 300

Thr Thr Leu Gly Asp Pro Ile Glu Ala Gln Ala Leu Leu Ala Thr Tyr
305                 310                 315                 320

Gly Lys Gly Arg Asp Pro Glu Lys Pro Leu Trp Leu Gly Ser Val Lys
                325                 330                 335

Ser Asn Leu Gly His Thr Gln Ala Ala Ala Gly Val Ala Ser Val Ile
            340                 345                 350

Lys Met Val Gln Ala Leu Arg His Gly Val Leu Pro Pro Thr Leu His
            355                 360                 365

Val Asp Arg Pro Ser Thr Glu Val Asp Trp Ser Ala Gly Ala Val Ser
            370                 375                 380

Leu Leu Thr Glu Ala Arg Glu Trp Pro Arg Glu Gly Arg Pro Arg Arg
385                 390                 395                 400

Ala Gly Val Ser Ser Phe Gly Ile Ser Gly Thr Asn Ala His Leu Ile
                405                 410                 415

Leu Glu Glu Ala Pro Glu Glu Pro Pro Val Ala Glu Ala Pro Ser
            420                 425                 430

Ala Gly Val Val Pro Val Val Ser Ala Arg Gly Ala Leu Ala Gly
            435                 440                 445
```

-continued

```
Gln Ala Gly Arg Leu Ala Ala Phe Leu Glu Ala Ser Asp Glu Pro Leu
    450                 455                 460
Val Thr Val Ala Gly Ala Leu Ile Cys Gly Arg Ser Arg Phe Gly Asp
465                 470                 475                 480
Arg Ala Val Val Ala Gly Thr Arg Ala Glu Ala Thr Ala Gly Leu
                485                 490                 495
Ala Ala Leu Ala Arg Gly Glu Ser Ala Ala Asp Val Val Thr Gly Thr
            500                 505                 510
Val Ala Ala Ser Gly Val Pro Gly Lys Leu Val Trp Val Phe Pro Gly
    515                 520                 525
Gln Gly Ser Gln Trp Val Gly Met Gly Arg Glu Leu Leu Glu Ala Ser
    530                 535                 540
Pro Val Phe Ala Ala Arg Ile Ala Glu Cys Ala Ala Leu Glu Pro
545                 550                 555                 560
Trp Ile Asp Trp Ser Leu Leu Asp Val Leu Arg Gly Glu Gly Asp Leu
                565                 570                 575
Asp Arg Val Asp Val Val Gln Pro Ala Ser Phe Ala Val Met Val Gly
            580                 585                 590
Leu Ala Ala Val Trp Ser Ser Val Gly Val Pro Asp Ala Val Leu
    595                 600                 605
Gly His Ser Gln Gly Glu Ile Ala Ala Ala Cys Val Ser Gly Ala Leu
    610                 615                 620
Ser Leu Gln Asp Ala Ala Lys Val Val Ala Leu Arg Ser Gln Ala Ile
625                 630                 635                 640
Ala Ala Lys Leu Ala Gly Arg Gly Met Ala Ser Val Ala Leu Ser
                645                 650                 655
Glu Glu Asp Ala Val Ala Arg Leu Arg His Trp Ala Asp Arg Val Glu
            660                 665                 670
Val Ala Ala Val Asn Ser Pro Ser Ser Val Val Ile Ala Gly Asp Ala
    675                 680                 685
Glu Ala Leu Asp Gln Ala Leu Glu Ala Leu Thr Gly Gln Asp Ile Arg
    690                 695                 700
Val Arg Arg Val Ala Val Asp Tyr Ala Ser His Thr Arg His Val Glu
705                 710                 715                 720
Asp Ile Gln Glu Pro Leu Ala Glu Ala Leu Ala Gly Ile Glu Ala His
                725                 730                 735
Ala Pro Thr Leu Pro Phe Phe Ser Thr Leu Thr Gly Asp Trp Ile Arg
            740                 745                 750
Glu Ala Gly Val Val Asp Gly Gly Tyr Trp Tyr Arg Asn Leu Arg Asn
    755                 760                 765
Gln Val Gly Phe Gly Pro Ala Val Ala Glu Leu Leu Gly Leu Gly His
    770                 775                 780
Arg Val Phe Val Glu Val Ser Ala His Pro Val Leu Val Gln Ala Ile
785                 790                 795                 800
Ser Ala Ile Ala Asp Asp Thr Asp Ala Val Thr Gly Ser Leu Arg
                805                 810                 815
Arg Glu Glu Gly Gly Leu Arg Arg Leu Leu Thr Ser Met Ala Glu Leu
            820                 825                 830
Phe Val Arg Gly Val Asp Val Asp Trp Ala Thr Met Val Pro Pro Ala
    835                 840                 845
Arg Val Asp Leu Pro Thr Tyr Ala Phe Asp His Gln His Tyr Trp Leu
    850                 855                 860
```

-continued

```
Arg Tyr Val Glu Thr Ala Thr Asp Ala Ala Gly Pro Val Val Arg Leu
865                 870                 875                 880

Pro Gln Thr Gly Gly Leu Val Phe Thr Thr Glu Trp Ser Leu Lys Ser
                885                 890                 895

Gln Pro Trp Leu Ala Glu His Thr Leu Glu Asp Leu Val Val Pro
            900                 905                 910

Gly Ala Ala Leu Val Glu Leu Ala Val Arg Ala Gly Asp Glu Ala Gly
            915                 920                 925

Thr Pro Val Leu Asp Glu Leu Ile Glu Thr Pro Leu Val Val Pro
        930                 935                 940

Glu Arg Gly Ala Ile Arg Val Gln Val Thr Val Ser Gly Pro Asp Asp
945                 950                 955                 960

Gly Thr Arg Thr Leu Glu Val His Ser Gln Pro Glu Asp Ala Thr Asp
                965                 970                 975

Glu Trp Thr Arg His Ala Thr Gly Thr Leu Ser Ala Thr Pro Asp Glu
            980                 985                 990

Ser Ser Gly Phe Asp Phe Thr Ala Trp Pro Pro Gly Ala Arg Gln
        995                 1000                1005

Leu Asp Gly Val Pro Ala Ile Trp Arg Ala Gly Asp Glu Ile Phe Ala
    1010                1015                1020

Glu Val Ser Leu Pro Asp Asp Ala Asp Ala Glu Ala Phe Gly Ile His
1025                1030                1035                1040

Pro Ala Leu Leu Asp Ala Ala Leu His Pro Ala Leu Pro Gly Asp Asp
                1045                1050                1055

Gly Leu Thr Gln Pro Met Glu Trp Arg Gly Leu Thr Leu His Ala Ala
            1060                1065                1070

Gly Ala Ser Thr Leu Arg Val Arg Leu Val Pro Gly Gly Phe Leu Glu
        1075                1080                1085

Ala Ala Asp Gly Ala Gly Ser Leu Val Val Thr Ala Lys Glu Val Ala
    1090                1095                1100

Leu Arg Pro Val Thr Ile Ala Arg Ser Arg Thr Thr Thr Arg Asp Ser
1105                1110                1115                1120

Leu Phe Gln Leu Asn Trp Ile Glu Leu Pro Glu Ser Gly Val Val Ala
                1125                1130                1135

Ala Ala Asp Asp Thr Glu Val Leu Glu Val Pro Ala Gly Asp Ser Pro
            1140                1145                1150

Leu Ala Ala Thr Ser Arg Val Leu Glu Arg Leu Gln Thr Trp Leu Thr
        1155                1160                1165

Glu Pro Glu Ala Glu Gln Leu Val Val Val Thr Arg Gly Ala Val Pro
    1170                1175                1180

Ala Gly Asp Thr Pro Val Thr Asp Pro Ala Ala Ala Val Trp Gly
1185                1190                1195                1200

Leu Val Arg Ser Ala Gln Ala Glu Asn Pro Asp Arg Ile Val Leu Leu
                1205                1210                1215

Asp Thr Asp Gly Glu Val Pro Leu Gly Ala Val Leu Ala Gly Gly Glu
            1220                1225                1230

Pro Gln Val Ala Val Arg Gly Thr Ala Leu Tyr Val Pro Arg Leu Ala
        1235                1240                1245

Arg Ala Asp Ala Ala Pro Val Ser Gly Leu His Gly Thr Val Leu Val
    1250                1255                1260

Ser Gly Ala Gly Val Leu Gly Glu Ile Val Ala Arg His Leu Val Thr
1265                1270                1275                1280

Arg His Gly Val Arg Lys Leu Val Leu Ala Ser Arg Arg Gly Leu Asp
```

-continued

```
                1285                1290                1295
Ala Asp Gly Ala Lys Asp Leu Val Thr Asp Leu Thr Gly Glu Gly Ala
            1300                1305                1310
Asp Val Ser Val Val Ala Cys Asp Leu Ala Asp Arg Asn Gln Val Ala
            1315                1320                1325
Ala Leu Leu Ala Asp His Arg Pro Ala Ser Val Ile His Thr Ala Gly
            1330                1335                1340
Val Leu Asp Asp Gly Val Ile Gly Thr Leu Thr Pro Glu Arg Leu Ala
1345                1350                1355                1360
Lys Val Phe Ala Pro Lys Val Asp Ala Val Arg His Leu Asp Glu Leu
                1365                1370                1375
Thr Arg Asp Leu Asp Leu Asp Ala Phe Val Val Phe Ser Ser Gly Ser
                1380                1385                1390
Gly Val Phe Gly Ser Pro Gly Gln Gly Asn Tyr Ala Ala Ala Asn Ala
                1395                1400                1405
Phe Leu Asp Ala Ala Met Ala Ser Arg Arg Ala Ala Gly Leu Pro Gly
            1410                1415                1420
Leu Ser Leu Ala Trp Gly Leu Trp Glu Gln Ala Thr Gly Met Thr Ala
1425                1430                1435                1440
His Leu Gly Gly Thr Asp Gln Ala Arg Met Ser Arg Gly Gly Val Arg
                1445                1450                1455
Pro Ile Thr Ala Glu Glu Gly Met Ala Leu Phe Asp Thr Ala Leu Gly
            1460                1465                1470
Ala Gln Pro Ala Leu Leu Val Pro Val Lys Leu Asp Leu Arg Glu Val
            1475                1480                1485
Arg Ala Gly Gly Ala Val Pro His Leu Leu Arg Gly Leu Val Arg Ala
            1490                1495                1500
Gly Arg Arg Gln Ala Gln Ala Ala Ser Thr Val Asp Asn Gln Leu Leu
1505                1510                1515                1520
Gly Arg Leu Ala Gly Leu Gly Ala Pro Glu Gln Glu Ala Leu Leu Val
                1525                1530                1535
Asp Leu Val Arg Gly Gln Val Ala Ala Val Leu Gly His Ala Gly Pro
            1540                1545                1550
Asp Ala Val Arg Ala Asp Thr Ala Phe Lys Asp Ala Gly Phe Asp Ser
            1555                1560                1565
Leu Thr Ser Val Asp Leu Arg Asn Arg Leu Arg Glu Ser Thr Gly Leu
            1570                1575                1580
Lys Leu Pro Ala Thr Leu Ala Phe Asp Tyr Pro Thr Pro Leu Val Leu
1585                1590                1595                1600
Ala Arg His Leu Arg Asp Glu Leu Gly Ala Gly Asp Ala Leu Ser
                1605                1610                1615
Val Val His Ala Arg Leu Glu Asp Val Glu Ala Leu Leu Gly Gly Leu
            1620                1625                1630
Arg Leu Asp Glu Ser Thr Lys Thr Gly Leu Thr Leu Arg Leu Gln Gly
            1635                1640                1645
Leu Val Ala Arg Cys Asn Gly Val Asn Asp Gln Thr Gly Gly Glu Thr
            1650                1655                1660
Leu Ala Asp Arg Leu Glu Ala Ala Ser Ala Asp Glu Val Leu Asp Phe
1665                1670                1675                1680
Ile Asp Glu Glu Leu Gly Leu Thr
                1685
```

<210> SEQ ID NO 8

```
<211> LENGTH: 3413
<212> TYPE: PRT
<213> ORGANISM: Amycolatopsis mediterranei

<400> SEQUENCE: 8
```

| | | | | | | | | | | | | | | |
|---|---|---|---|---|---|---|---|---|---|---|---|---|---|---|
| Met | Ala | Thr | Asp | Glu | Lys | Leu | Leu | Lys | Tyr | Leu | Lys | Arg | Val | Thr | Ala |
| 1 | | | | 5 | | | | | 10 | | | | | 15 | |

Glu Leu His Ser Leu Arg Lys Gln Gly Ala Arg His Ala Asp Glu Pro
              20                  25                  30

Leu Ala Val Val Gly Met Ala Cys Arg Phe Pro Gly Gly Val Ser Ser
         35                  40                  45

Pro Glu Asp Leu Trp Gln Leu Val Ala Gly Val Asp Ala Leu Ser
     50                  55                  60

Asp Phe Pro Asp Asp Arg Gly Trp Glu Leu Asp Gly Leu Phe Asp Pro
65                  70                  75                  80

Asp Pro Asp His Pro Gly Thr Ser Tyr Thr Ser Gln Gly Gly Phe Leu
             85                  90                  95

Arg Gly Ala Gly Leu Phe Asp Ala Gly Leu Phe Gly Ile Ser Pro Arg
             100                 105                 110

Glu Ala Leu Val Met Asp Pro Gln Gln Arg Val Leu Leu Glu Thr Ser
             115                 120                 125

Trp Glu Ala Leu Glu Asp Ala Gly Val Asp Pro Leu Ser Leu Lys Gly
    130                 135                 140

Ser Asp Val Gly Val Phe Ser Gly Val Phe Thr Gln Gly Tyr Gly Ala
145                 150                 155                 160

Gly Ala Ile Thr Pro Asp Leu Glu Ala Phe Ala Gly Ile Gly Ala Ala
                165                 170                 175

Ser Ser Val Ala Ser Gly Arg Val Ser Tyr Val Phe Gly Leu Glu Gly
            180                 185                 190

Pro Ala Val Thr Ile Asp Thr Ala Cys Ser Ser Ser Leu Val Ala Ile
        195                 200                 205

His Leu Ala Ala Gln Ala Leu Arg Ala Gly Glu Cys Ser Met Ala Leu
    210                 215                 220

Ala Gly Gly Ala Thr Val Met Pro Thr Pro Gly Thr Phe Val Ala Phe
225                 230                 235                 240

Ser Arg Gln Arg Val Leu Ala Ala Asp Gly Arg Ser Lys Ala Phe Ser
                245                 250                 255

Ser Thr Ala Asp Gly Thr Gly Trp Ala Glu Gly Ala Gly Val Leu Val
            260                 265                 270

Leu Glu Arg Leu Ser Val Ala Gln Glu Arg Gly His Arg Ile Leu Ala
        275                 280                 285

Val Leu Arg Gly Ser Ala Val Asn Gln Asp Gly Ala Ser Asn Gly Leu
    290                 295                 300

Thr Ala Pro Asn Gly Pro Ser Gln Gln Arg Val Ile Arg Lys Ala Leu
305                 310                 315                 320

Ala Gly Ala Gly Leu Val Ala Ser Asp Val Asp Val Val Glu Ala His
                325                 330                 335

Gly Thr Gly Thr Ala Leu Gly Asp Pro Ile Glu Ala Gln Ala Leu Leu
            340                 345                 350

Ala Thr Tyr Gly Gln Gly Arg Glu Arg Pro Leu Trp Leu Gly Ser Val
        355                 360                 365

Lys Ser Asn Phe Gly His Thr Gln Ala Ala Ala Gly Val Ala Gly Val
    370                 375                 380

Ile Lys Met Val Gln Ala Leu Arg His Gly Ala Met Pro Pro Thr Leu

-continued

```
385                 390                 395                 400
His Val Ala Glu Pro Thr Pro Glu Val Asp Trp Ser Ala Gly Ala Val
            405                 410                 415
Glu Leu Leu Thr Glu Pro Arg Glu Trp Pro Ala Gly Asp Arg Pro Arg
            420                 425                 430
Arg Ala Gly Val Ser Ala Phe Gly Ile Ser Gly Thr Asn Ala His Leu
            435                 440                 445
Ile Leu Glu Glu Ala Pro Pro Ala Asp Ala Val Ala Glu Glu Pro Glu
    450                 455                 460
Phe Lys Gly Pro Val Pro Leu Val Val Ser Ala Gly Ser Pro Thr Ser
465                 470                 475                 480
Leu Ala Ala Gln Ala Gly Arg Leu Ala Glu Val Leu Ala Ser Gly Gly
            485                 490                 495
Val Ser Arg Ala Arg Leu Ala Ser Gly Leu Leu Ser Gly Arg Ala Leu
            500                 505                 510
Leu Gly Asp Arg Ala Val Val Ala Gly Thr Asp Glu Asp Ala Val
            515                 520                 525
Ala Gly Leu Arg Ala Leu Ala Arg Gly Asp Arg Ala Pro Gly Val Leu
    530                 535                 540
Thr Gly Ser Ala Lys His Gly Lys Val Val Tyr Val Phe Pro Gly Gln
545                 550                 555                 560
Gly Ser Gln Arg Leu Gly Met Gly Arg Glu Leu Tyr Asp Arg Tyr Pro
            565                 570                 575
Val Phe Ala Thr Ala Phe Asp Glu Ala Cys Glu Gln Leu Asp Val Cys
            580                 585                 590
Leu Ala Gly Arg Ala Gly His Arg Val Arg Asp Val Val Leu Gly Glu
            595                 600                 605
Val Pro Ala Glu Thr Gly Leu Leu Asn Gln Thr Val Phe Thr Gln Ala
    610                 615                 620
Gly Leu Phe Ala Val Glu Ser Ala Leu Phe Arg Leu Ala Glu Ser Trp
625                 630                 635                 640
Gly Val Arg Pro Asp Val Val Leu Gly His Ser Ile Gly Glu Ile Thr
            645                 650                 655
Ala Ala Tyr Ala Ala Gly Val Phe Ser Leu Pro Asp Ala Ala Arg Ile
            660                 665                 670
Val Ala Ala Arg Gly Arg Leu Met Gln Ala Leu Ala Pro Gly Gly Ala
            675                 680                 685
Met Val Ala Val Ala Ser Glu Ala Glu Val Ala Glu Leu Leu Gly
            690                 695                 700
Asp Gly Val Glu Leu Ala Ala Val Asn Gly Pro Ser Ala Val Val Leu
705                 710                 715                 720
Ser Gly Asp Ala Asp Ala Val Ala Ala Ala Arg Met Arg Glu
            725                 730                 735
Arg Gly His Lys Thr Lys Gln Leu Lys Val Ser His Ala Phe His Ser
            740                 745                 750
Ala Arg Met Ala Pro Met Leu Ala Glu Phe Ala Glu Leu Ala Gly
            755                 760                 765
Val Thr Trp Arg Glu Pro Glu Ile Pro Val Val Ser Asn Val Thr Gly
            770                 775                 780
Arg Phe Ala Glu Pro Gly Glu Leu Thr Glu Pro Gly Tyr Trp Ala Glu
785                 790                 795                 800
His Val Arg Arg Pro Val Arg Phe Ala Glu Gly Val Ala Ala Ala Thr
            805                 810                 815
```

-continued

```
Glu Ser Gly Gly Ser Leu Phe Val Glu Leu Gly Pro Gly Ala Ala Leu
            820                 825                 830

Thr Ala Leu Val Glu Glu Thr Ala Glu Val Thr Cys Val Ala Ala Leu
            835                 840                 845

Arg Asp Asp Arg Pro Glu Val Thr Ala Leu Ile Thr Ala Val Ala Glu
            850                 855                 860

Leu Phe Val Arg Gly Val Ala Val Asp Trp Pro Ala Leu Leu Pro Pro
865                 870                 875                 880

Val Thr Gly Phe Val Asp Leu Pro Lys Tyr Ala Phe Asp Gln Gln His
            885                 890                 895

Tyr Trp Leu Gln Pro Ala Ala Gln Ala Thr Asp Ala Ala Ser Leu Gly
            900                 905                 910

Gln Val Ala Ala Asp His Pro Leu Leu Gly Ala Val Val Arg Leu Pro
            915                 920                 925

Gln Ser Asp Gly Leu Val Phe Thr Ser Arg Leu Ser Leu Lys Ser His
            930                 935                 940

Pro Trp Leu Ala Asp His Val Ile Gly Gly Val Val Leu Val Ala Gly
945                 950                 955                 960

Thr Gly Leu Val Glu Leu Ala Val Arg Ala Gly Asp Glu Ala Gly Cys
            965                 970                 975

Pro Val Leu Glu Glu Leu Val Ile Glu Ala Pro Leu Val Val Pro Asp
            980                 985                 990

His Gly Gly Val Arg Ile Gln Val Val Val Gly Ala Pro Gly Glu Thr
            995                 1000                1005

Gly Ser Arg Ala Val Glu Val Tyr Ser Leu Arg Glu Asp Ala Gly Ala
            1010                1015                1020

Glu Val Trp Ala Arg His Ala Thr Gly Phe Leu Ala Ala Thr Pro Ser
1025                1030                1035                1040

Gln His Lys Pro Phe Asp Phe Thr Ala Trp Pro Pro Gly Val Glu
            1045                1050                1055

Arg Val Asp Val Glu Asp Phe Tyr Asp Gly Leu Val Asp Arg Gly Tyr
            1060                1065                1070

Ala Tyr Gly Pro Ser Phe Arg Gly Leu Arg Ala Val Trp Arg Arg Gly
            1075                1080                1085

Asp Glu Val Phe Ala Glu Val Ala Leu Ala Glu Asp Asp Arg Ala Asp
            1090                1095                1100

Ala Ala Arg Phe Gly Ile His Pro Gly Leu Leu Asp Ala Ala Leu His
1105                1110                1115                1120

Ala Gly Met Ala Gly Ala Thr Thr Thr Glu Glu Pro Gly Arg Pro Val
            1125                1130                1135

Leu Pro Phe Ala Trp Asn Gly Leu Val Leu His Ala Gly Ala Ser
            1140                1145                1150

Ala Leu Arg Val Arg Leu Ala Pro Ser Gly Pro Asp Ala Leu Ser Val
            1155                1160                1165

Glu Ala Ala Asp Glu Ala Gly Gly Leu Val Val Thr Ala Asp Ser Leu
            1170                1175                1180

Val Ser Arg Pro Val Ser Ala Glu Gln Leu Gly Ala Ala Ala Asn His
1185                1190                1195                1200

Asp Ala Leu Phe Arg Val Glu Trp Thr Glu Ile Ser Ser Ala Gly Asp
            1205                1210                1215

Val Pro Ala Asp His Val Glu Val Leu Glu Ala Val Gly Glu Asp Pro
            1220                1225                1230
```

```
Leu Glu Leu Thr Gly Arg Val Leu Glu Ala Val Gln Thr Trp Leu Ala
        1235                1240                1245
Asp Ala Ala Asp Asp Ala Arg Leu Val Val Thr Arg Gly Ala Val
    1250                1255                1260
His Glu Val Thr Asp Pro Ala Gly Ala Val Trp Gly Leu Ile Arg
1265                1270                1275                1280
Ala Ala Gln Ala Glu Asn Pro Asp Arg Ile Val Leu Leu Asp Thr Asp
                1285                1290                1295
Gly Glu Val Pro Leu Gly Arg Val Leu Ala Thr Gly Glu Pro Gln Thr
                1300                1305                1310
Ala Val Arg Gly Ala Thr Leu Phe Ala Pro Arg Leu Ala Arg Ala Glu
                1315                1320                1325
Ala Ala Glu Ala Pro Ala Val Thr Gly Gly Thr Val Leu Ile Ser Gly
                1330                1335                1340
Ala Gly Ser Leu Gly Ala Leu Thr Ala Arg His Leu Val Ala Arg His
1345                1350                1355                1360
Gly Val Arg Arg Leu Val Leu Val Ser Arg Arg Gly Pro Asp Ala Asp
                1365                1370                1375
Gly Met Ala Glu Leu Thr Ala Glu Leu Ile Ala Gln Gly Ala Glu Val
                1380                1385                1390
Ala Val Val Ala Cys Asp Leu Ala Asp Arg Asp Gln Val Arg Val Leu
                1395                1400                1405
Leu Ala Glu His Arg Pro Asn Ala Val Val His Thr Ala Gly Val Leu
                1410                1415                1420
Asp Asp Gly Val Phe Glu Ser Leu Thr Arg Glu Arg Leu Ala Lys Val
1425                1430                1435                1440
Phe Ala Pro Lys Val Thr Ala Ala Asn His Leu Asp Glu Leu Thr Arg
                1445                1450                1455
Glu Leu Asp Leu Arg Ala Phe Val Val Phe Ser Ser Ala Ser Gly Val
                1460                1465                1470
Phe Gly Ser Ala Gly Gln Gly Asn Tyr Ala Ala Ala Asn Ala Tyr Leu
                1475                1480                1485
Asp Ala Val Val Ala Asn Arg Arg Ala Ala Gly Leu Pro Gly Thr Ser
    1490                1495                1500
Leu Ala Trp Gly Leu Trp Glu Gln Thr Asp Gly Met Thr Ala His Leu
1505                1510                1515                1520
Gly Asp Ala Asp Gln Ala Arg Ala Ser Arg Gly Gly Val Leu Ala Ile
                1525                1530                1535
Ser Pro Ala Glu Gly Met Glu Leu Phe Asp Ala Ala Pro Asp Gly Leu
                1540                1545                1550
Val Val Pro Val Lys Leu Asp Leu Arg Lys Thr Arg Ala Gly Gly Thr
                1555                1560                1565
Val Pro His Leu Leu Arg Gly Leu Val Arg Pro Gly Arg Gln Gln Ala
    1570                1575                1580
Arg Pro Ala Ser Thr Val Asp Asn Gly Leu Ala Gly Arg Leu Ala Gly
1585                1590                1595                1600
Leu Ala Pro Ala Glu Gln Glu Ala Leu Leu Leu Asp Val Val Arg Thr
                1605                1610                1615
Gln Val Ala Leu Val Leu Gly His Ala Gly Pro Glu Ala Val Arg Ala
                1620                1625                1630
Asp Thr Ala Phe Lys Asp Thr Gly Phe Asp Ser Leu Thr Ser Val Glu
                1635                1640                1645
Leu Arg Asn Arg Leu Arg Glu Ala Ser Gly Leu Lys Leu Pro Ala Thr
```

-continued

```
                1650                1655                1660
Leu Val Phe Asp Tyr Pro Thr Pro Val Ala Leu Ala Arg Tyr Leu Arg
1665                1670                1675                1680
Asp Glu Leu Gly Asp Thr Val Ala Thr Thr Pro Val Ala Thr Ala Ala
                1685                1690                1695
Ala Ala Asp Ala Gly Glu Pro Ile Ala Ile Val Gly Met Ala Cys Arg
                1700                1705                1710
Leu Pro Gly Gly Val Thr Asp Pro Glu Gly Leu Trp Arg Leu Val Arg
                1715                1720                1725
Asp Gly Leu Glu Gly Leu Ser Pro Phe Pro Glu Asp Arg Gly Trp Asp
                1730                1735                1740
Leu Glu Asn Leu Phe Asp Asp Pro Asp Arg Ser Gly Thr Thr Tyr
1745                1750                1755                1760
Thr Ser Arg Gly Gly Phe Leu Asp Gly Ala Gly Leu Phe Asp Ala Gly
                1765                1770                1775
Phe Phe Gly Ile Ser Pro Arg Glu Ala Leu Ala Met Asp Pro Gln Gln
                1780                1785                1790
Arg Leu Leu Leu Glu Ala Ala Trp Glu Ala Leu Glu Gly Thr Gly Val
                1795                1800                1805
Asp Pro Gly Ser Leu Lys Gly Ala Asp Val Gly Val Phe Ala Gly Val
                1810                1815                1820
Ser Asn Gln Gly Tyr Gly Met Gly Ala Asp Pro Ala Glu Leu Ala Gly
1825                1830                1835                1840
Tyr Ala Ser Thr Ala Gly Ala Ser Ser Val Val Ser Gly Arg Val Ser
                1845                1850                1855
Tyr Val Phe Gly Phe Glu Gly Pro Ala Val Thr Ile Asp Thr Ala Cys
                1860                1865                1870
Ser Ser Ser Leu Val Ala Met His Leu Ala Gly Gln Ala Leu Arg Gln
                1875                1880                1885
Gly Glu Cys Ser Met Ala Leu Ala Gly Gly Val Thr Val Met Gly Thr
                1890                1895                1900
Pro Gly Thr Phe Val Glu Phe Ala Lys Gln Arg Gly Leu Ala Gly Asp
1905                1910                1915                1920
Gly Arg Cys Lys Ala Tyr Ala Glu Gly Ala Asp Gly Thr Gly Trp Ala
                1925                1930                1935
Glu Gly Val Gly Val Val Leu Glu Arg Leu Ser Val Ala Arg Glu
                1940                1945                1950
Arg Gly His Arg Val Leu Ala Val Leu Arg Gly Ser Ala Val Asn Ser
                1955                1960                1965
Asp Gly Ala Ser Asn Gly Leu Thr Ala Pro Asn Gly Pro Ser Gln Gln
                1970                1975                1980
Arg Val Ile Arg Arg Ala Leu Ala Gly Ala Gly Leu Glu Pro Ser Asp
1985                1990                1995                2000
Val Asp Ile Val Glu Gly His Gly Thr Gly Thr Ala Leu Gly Asp Pro
                2005                2010                2015
Ile Glu Ala Gln Ala Leu Leu Ala Thr Tyr Gly Lys Asp Arg Asp Pro
                2020                2025                2030
Glu Thr Pro Leu Trp Leu Gly Ser Val Lys Ser Asn Phe Gly His Thr
                2035                2040                2045
Gln Ser Ala Ala Gly Val Ala Gly Val Ile Lys Met Val Gln Ala Leu
                2050                2055                2060
Arg His Gly Val Met Pro Pro Thr Leu His Val Asp Arg Pro Thr Ser
2065                2070                2075                2080
```

-continued

```
Gln Val Asp Trp Ser Ala Gly Ala Val Glu Val Leu Thr Glu Ala Arg
            2085                2090                2095
Glu Trp Pro Arg Asn Gly Arg Pro Arg Arg Ala Gly Val Ser Ser Phe
        2100                2105                2110
Gly Ile Ser Gly Thr Asn Ala His Leu Ile Ile Glu Glu Ala Pro Ala
            2115                2120                2125
Glu Pro Gln Leu Ala Gly Pro Pro Asp Gly Gly Val Val Pro Leu
        2130                2135                2140
Val Val Ser Ala Arg Ser Pro Gly Ala Leu Ala Gly Gln Ala Arg Arg
2145            2150                2155                2160
Leu Ala Thr Phe Leu Gly Asp Gly Pro Leu Ser Asp Val Ala Gly Ala
            2165                2170                2175
Leu Thr Ser Arg Ala Leu Phe Gly Glu Arg Ala Val Val Ala Asp
        2180                2185                2190
Ser Ala Glu Glu Ala Arg Ala Gly Leu Gly Ala Leu Ala Arg Gly Glu
        2195                2200                2205
Asp Ala Pro Gly Leu Val Arg Gly Arg Val Pro Ala Ser Gly Leu Pro
    2210                2215                2220
Gly Lys Leu Val Trp Val Phe Pro Gly Gln Gly Thr Gln Trp Val Gly
2225            2230                2235                2240
Met Gly Arg Glu Leu Leu Glu Glu Ser Pro Val Phe Ala Glu Arg Ile
            2245                2250                2255
Ala Glu Cys Ala Ala Ala Leu Glu Pro Trp Ile Gly Trp Ser Leu Phe
            2260                2265                2270
Asp Val Leu Arg Gly Asp Gly Asp Leu Asp Arg Val Asp Val Leu Gln
        2275                2280                2285
Pro Ala Cys Phe Ala Val Met Val Gly Leu Ala Ala Val Trp Ser Ser
        2290                2295                2300
Ala Gly Val Val Pro Asp Ala Val Leu Gly His Ser Gln Gly Glu Ile
2305            2310                2315                2320
Ala Ala Ala Cys Val Ser Gly Ala Leu Ser Leu Glu Asp Ala Ala Lys
            2325                2330                2335
Val Val Ala Leu Arg Ser Gln Ala Ile Ala Ala Lys Leu Ser Gly Arg
            2340                2345                2350
Gly Gly Met Ala Ser Val Ala Leu Gly Glu Ala Asp Val Val Ser Arg
        2355                2360                2365
Leu Ala Asp Gly Val Glu Val Ala Ala Val Asn Gly Pro Ala Ser Val
    2370                2375                2380
Val Ile Ala Gly Asp Ala Gln Ala Leu Asp Glu Thr Leu Glu Ala Leu
2385            2390                2395                2400
Ser Gly Ala Gly Ile Arg Ala Arg Arg Val Ala Val Asp Tyr Ala Ser
            2405                2410                2415
His Thr Arg His Val Glu Asp Ile Glu Asp Thr Leu Ala Glu Ala Leu
        2420                2425                2430
Ala Gly Ile Asp Ala Arg Ala Pro Leu Val Pro Phe Leu Ser Thr Leu
        2435                2440                2445
Thr Gly Glu Trp Ile Arg Asp Glu Gly Val Val Asp Gly Gly Tyr Trp
    2450                2455                2460
Tyr Arg Asn Leu Arg Gly Arg Val Arg Phe Gly Pro Ala Val Glu Ala
2465            2470                2475                2480
Leu Leu Ala Gln Gly His Gly Val Phe Val Glu Leu Ser Ala His Pro
            2485                2490                2495
```

-continued

```
Val Leu Val Gln Pro Ile Thr Glu Leu Thr Asp Glu Thr Ala Ala Val
            2500                2505                2510

Val Thr Gly Ser Leu Arg Arg Asp Asp Gly Gly Leu Arg Arg Leu Leu
            2515                2520                2525

Thr Ser Met Ala Glu Leu Phe Val Arg Gly Val Glu Val Asp Trp Thr
            2530                2535                2540

Ser Leu Val Pro Pro Ala Arg Ala Asp Leu Pro Thr Tyr Ala Phe Asp
2545                2550                2555                2560

His Glu His Tyr Trp Leu Arg Ala Ala Asp Thr Ala Ser Asp Ala Val
            2565                2570                2575

Ser Leu Gly Leu Ala Gly Ala Asp His Pro Leu Leu Gly Ala Val Val
            2580                2585                2590

Gln Leu Pro Gln Ser Asp Gly Leu Val Phe Thr Ser Arg Leu Ser Leu
            2595                2600                2605

Arg Ser His Pro Trp Leu Ala Asp His Ala Val Arg Asp Val Val Ile
            2610                2615                2620

Val Pro Gly Thr Gly Leu Val Glu Leu Ala Val Arg Ala Gly Asp Glu
2625                2630                2635                2640

Ala Gly Cys Pro Val Leu Asp Glu Leu Val Ile Glu Ala Pro Leu Val
            2645                2650                2655

Val Pro Arg Arg Gly Gly Val Arg Val Gln Val Ala Leu Gly Gly Pro
            2660                2665                2670

Ala Asp Asp Gly Ser Arg Thr Val Asp Val Phe Ser Leu Arg Glu Asp
            2675                2680                2685

Ala Asp Ser Trp Leu Arg His Ala Thr Gly Val Leu Val Pro Glu Asn
            2690                2695                2700

Arg Pro Arg Gly Thr Ala Ala Phe Asp Phe Ala Ala Trp Pro Pro Pro
2705                2710                2715                2720

Glu Ala Lys Pro Val Asp Leu Thr Gly Ala Tyr Asp Val Leu Ala Asp
            2725                2730                2735

Val Gly Tyr Gly Tyr Gly Pro Thr Phe Arg Ala Val Arg Ala Val Trp
            2740                2745                2750

Arg Arg Gly Ser Gly Asn Thr Thr Glu Thr Phe Ala Glu Ile Ala Leu
            2755                2760                2765

Pro Glu Asp Ala Arg Ala Glu Ala Gly Arg Phe Gly Ile His Pro Ala
            2770                2775                2780

Leu Leu Asp Ala Ala Leu His Ser Thr Met Val Ser Ala Ala Ala Asp
2785                2790                2795                2800

Thr Glu Ser Tyr Gly Asp Glu Val Arg Leu Pro Phe Ala Trp Asn Gly
            2805                2810                2815

Leu Arg Leu His Ala Ala Gly Ala Ser Val Leu Arg Val Arg Val Ala
            2820                2825                2830

Lys Pro Glu Arg Asp Ser Leu Ser Leu Glu Ala Val Asp Glu Ser Gly
            2835                2840                2845

Gly Leu Val Val Thr Leu Asp Ser Leu Val Gly Arg Pro Val Ser Asn
2850                2855                2860

Asp Gln Leu Thr Thr Ala Ala Gly Pro Ala Gly Ala Gly Ser Leu Tyr
2865                2870                2875                2880

Arg Val Asp Trp Thr Pro Leu Ser Ser Val Asp Thr Ser Gly Arg Val
            2885                2890                2895

Pro Ser Trp Leu Pro Val Ala Thr Ala Glu Glu Val Ala Thr Leu Ala
            2900                2905                2910

Asp Asp Val Leu Thr Gly Ala Thr Glu Ala Pro Ala Val Ala Val Met
```

-continued

```
                2915                2920                2925
Glu Ala Val Ala Asp Glu Gly Ser Val Leu Ala Leu Thr Val Arg Val
            2930                2935                2940
Leu Asp Val Val Gln Cys Trp Leu Ala Gly Gly Leu Glu Gly Thr
2945                2950                2955                2960
Lys Leu Ala Ile Val Thr Arg Gly Ala Val Pro Ala Gly Asp Gly Val
                2965                2970                2975
Val His Asp Pro Ala Ala Ala Val Trp Gly Leu Val Arg Ala Ala
            2980                2985                2990
Gln Ala Glu Asn Pro Asp Arg Ile Val Leu Leu Asp Val Glu Pro Glu
            2995                3000                3005
Ala Asp Val Pro Pro Leu Leu Gly Ser Val Leu Ala Asp Gly Glu Pro
3010                3015                3020
Gln Val Ala Val Arg Gly Thr Thr Leu Ser Ile Pro Arg Leu Ala Arg
3025                3030                3035                3040
Ala Ala Arg Pro Asp Pro Ala Ala Gly Phe Lys Thr Arg Gly Pro Val
            3045                3050                3055
Leu Val Thr Gly Gly Thr Gly Ser Leu Gly Gly Leu Val Ala Arg His
            3060                3065                3070
Leu Val Glu Arg His Gly Val Arg Gln Leu Val Leu Ala Ser Arg Arg
            3075                3080                3085
Gly Leu Asp Ala Glu Gly Ala Lys Asp Leu Val Thr Asp Leu Thr Ala
            3090                3095                3100
Leu Gly Ala Asp Val Ala Val Ala Ala Cys Asp Val Ala Asp Arg Asp
3105                3110                3115                3120
Gln Val Ala Ala Leu Leu Thr Glu His Arg Pro Ser Ala Val Val His
            3125                3130                3135
Thr Ala Gly Val Pro Asp Ala Gly Val Ile Gly Thr Val Thr Pro Asp
            3140                3145                3150
Arg Leu Ala Glu Val Phe Ala Pro Lys Val Thr Ala Ala Arg His Leu
            3155                3160                3165
Asp Glu Leu Thr Arg Asp Leu Asp Leu Asp Ser Phe Val Val Tyr Ser
            3170                3175                3180
Ser Val Ser Ala Val Phe Met Gly Ala Gly Ser Gly Ser Tyr Ala Ala
3185                3190                3195                3200
Ala Asn Ala Tyr Leu Asp Gly Leu Met Ala His Arg Arg Ala Ala Gly
            3205                3210                3215
Leu Pro Gly Gln Ser Leu Ala Trp Gly Leu Trp Asp Gln Thr Thr Gly
            3220                3225                3230
Gly Met Ala Ala Gly Thr Asp Glu Ala Gly Arg Ala Arg Met Thr Arg
            3235                3240                3245
Arg Gly Gly Leu Val Ala Met Lys Pro Ala Ala Gly Leu Asp Leu Phe
3250                3255                3260
Asp Ala Ala Ile Gly Ser Gly Glu Pro Leu Leu Val Pro Ala Gln Leu
3265                3270                3275                3280
Asp Leu Arg Gly Leu Arg Ala Glu Ala Ala Gly Gly Thr Glu Val Pro
            3285                3290                3295
His Leu Leu Arg Gly Leu Val Arg Ala Gly Arg Gln Gln Ala Arg Ala
            3300                3305                3310
Ala Ser Thr Val Glu Glu Asn Trp Ala Gly Arg Leu Ala Gly Leu Glu
            3315                3320                3325
Pro Ala Glu Arg Gly Gln Val Leu Leu Glu Leu Val Arg Ala Gln Val
            3330                3335                3340
```

```
Ala Gly Val Leu Gly Tyr Arg Ala Ala His Gln Val Asp Pro Asp Gln
3345                3350                3355                3360

Gly Leu Phe Glu Ile Gly Phe Asp Ser Leu Thr Ala Ile Glu Leu Arg
            3365                3370                3375

Asn Arg Leu Arg Ala Arg Thr Glu Arg Lys Ile Ser Pro Gly Val Val
        3380                3385                3390

Phe Asp His Pro Thr Pro Ala Leu Leu Ala Ala His Leu Asn Glu Leu
    3395                3400                3405

Leu Arg Lys Lys Val
    3410

<210> SEQ ID NO 9
<211> LENGTH: 226
<212> TYPE: PRT
<213> ORGANISM: Amycolata autotrophica

<400> SEQUENCE: 9

Met Ala Ile Pro Tyr Ser Ser Leu Ala Tyr Glu Leu Arg Asp Ala Val
1               5                   10                  15

Asn Val Val Asp Leu Asp Glu Asp Val Phe Val Thr Ser Ile Ala
                20                  25                  30

Glu Gly Gln Gly Gly Ala Cys Tyr His Leu Asn Arg Leu Phe His Arg
            35                  40                  45

Leu Leu Thr Glu Leu Gly Tyr Asp Val Thr Pro Leu Ala Gly Ser Thr
    50                  55                  60

Ala Glu Gly Arg Glu Thr Phe Gly Thr Asp Val Glu His Met Phe Asn
65                  70                  75                  80

Leu Val Thr Leu Asp Gly Ala Asp Trp Leu Val Asp Val Gly Tyr Pro
                85                  90                  95

Gly Pro Thr Tyr Val Glu Pro Leu Ala Val Ser Pro Ala Val Gln Thr
            100                 105                 110

Gln Tyr Gly Ser Gln Phe Arg Leu Val Glu Gln Glu Thr Gly Tyr Ala
        115                 120                 125

Leu Gln Arg Arg Gly Ala Val Thr Arg Trp Ser Val Val Tyr Thr Phe
    130                 135                 140

Thr Thr Gln Pro Arg Gln Trp Ser Asp Trp Lys Glu Leu Glu Asp Asn
145                 150                 155                 160

Phe Arg Ala Leu Val Gly Asp Thr Thr Arg Thr Asp Thr Gln Glu Thr
                165                 170                 175

Leu Cys Gly Arg Ala Phe Ala Asn Gly Gln Val Phe Leu Arg Gln Arg
            180                 185                 190

Arg Tyr Leu Thr Val Glu Asn Gly Arg Glu Gln Val Arg Thr Ile Thr
        195                 200                 205

Asp Asp Asp Glu Phe Arg Ala Leu Val Ser Arg Val Leu Ser Gly Asp
    210                 215                 220

His Gly
225
```

RIFAMYCIN BIOSYNTHESIS GENE CLUSTER

This a continuation of Ser. No. 09/242,744, Mar. 24, 1999, abandoned, which is a 371 of PCT/EP97/04495, Aug. 18, 1997.

Rifamycins form an important group of macrocyclic antibiotics (Wehrli, Topics in Current Chemistry (1971), 72, 21–49). They consist of a naphthoquinone chromophore which is spanned by a long aliphatic bridge. Rifamycins belong to the class of ansamycin antibiotics which are produced by several Gram-positive soil bacteria of the *actinomycetes* group and a few plants.

Ansamycins are characterized by a flat aromatic nucleus spanned by a long aliphatic bridge joining opposite positions of the nucleus. Two different groups of ansamycins can be distinguished by the structure of the aromatic nucleus. One group has a naphthoquinoid chromophore, with the typical representatives being rifamycin, streptovaricin, tolypomycin and naphthomycin. The second group, which has a benzoquinoid chromophore, is characterized by geldanamycin, maytansines and ansamitocines (Ghisalba et al., Biotechnology of Industrial Antibiotics Vandamme E. J. Ed., Decker Inc. New York, (1984) 281–327). In contrast to antibiotics of the macrolide type, the ansamycins contain in the aliphatic ring system not a lactone linkage but an amide linkage which forms the connection to the chromophore.

The discovery of the rifamycins produced by the microorganism *Streptomyces mediterranei* (as the organism was called at that time, see below) was described for the first time in 1959 (Sensi et al., Farmaco Ed. Sci. (1959) 14, 146–147). Extraction with ethyl acetate of the acidified cultures of *Streptomyces mediterranei* resulted in isolation of a mixture of antibiotically active components, the rifamycins A, B, C, D and E. Rifamycin B, the most stable component, was separated from the other components and isolated on the basis of its strongly acidic properties and ease of salt formation.

Rifamycin B has the structure of the formula (1)

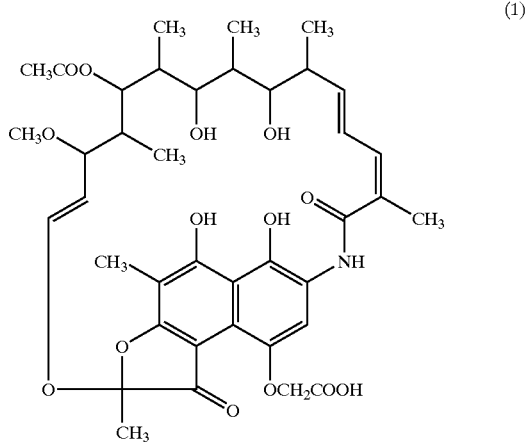

(1)

Rifamycin B is the main component of the fermentation when barbiturate is added to the fermentation medium and/or improved producer mutants of *Streptomyces mediterranei* are used.

The rifamycin producer strain was originally classified as *Streptomyces mediterranei* (Sensi. et al., Farmaco Ed. Sci. (1959) 14, 146–147). Analysis of the cell wall of *Streptomyces mediterranei* by Thiemann et al. later revealed that this strain has a cell wall typical of *Nocardia,* and the strain was reclassified as *Nocardia mediterranei* (Thieman et al. Arch. Microbiol. (1969), 67 147–151). *Nocardia mediterranei* has been reclassified again on the basis of more recent accurate morphological and biochemical criteria. Based on the exact composition of the cell wall, the absence of mycolic acid and the insensitivity to *Nocardia* and *Rhodococcus* phages, the strain has been assigned to the new genus *Amycolatopsis* as *Amycolatopsis mediterranei* (Lechevalier et al., Int. J. Syst. Bacteriol. (1986), 36, 29).

Rifamycins have a strong antibiotic activity mainly against Gram-positive bacteria such as mycobacteria, neisserias and staphylococci. The bactericidal effect of rifamycins derives from specific inhibition of the bacterial DNA-dependent RNA polymerase, which interrupts RNA biosynthesis (Wehrli and Staehelin, Bacteriol. Rev. (1971), 35, 290–309). The semisynthetic rifamycin B derivative rifampin (rifampicin) is widely used clinically as antibiotic against the agent causing tuberculosis, *Mycobacterium tuberculosis.*

The naphthoquinoid ansamycins of the streptovaricin and tolypomycin group show, like rifamycin, an antibacterial effect by inhibiting bacterial RNA polymerase. By contrast, naphthomycin has an antibacterial effect without inhibiting bacterial RNA polymerase. The benzoquinoid ansamycins show no inhibition of bacterial RNA polymerase, and they therefore have only relatively weak antibacterial activity, if any. On the other hand, some representatives of this class of substances have an effect on eukaryotic cells. Thus, antifungal, antiprotozoal and antitumour properties have been described for geldanamycin. On the other hand, antimitotic (antitubilin), antileukaemic and antitumour properties are ascribed to the maytansines. Some rifamycins also show antitumour and antiviral activity, but only at high concentrations. This biological effect thus appears to be nonspecific.

Despite the great structural variety of the ansamycins, their biosynthesis appears to take place by a metabolic pathway which contains many common elements (Ghisalba et al. Biotechnology of Industrial Antibiotics Vandamme E. J. Ed., Decker Inc. New York, (1984) 281–327). The aromatic nucleus for all ansamycins is probably built up starting from 3-amino-5-hydroxybenzoic acid. Starting from this molecule, which is presumably activated as coenzyme A, the entire aliphatic bridge is synthesized by a multifunctional polyketide synthase. The length of the bridge and the processing of the keto groups, which are initially formed by the condensation steps, are controlled by the polyketide synthase. To build up the complete aliphatic bridge for rifamycins, 10 condensation steps, 2 with acetate and 8 with propionate as building blocks, are necessary. The sequence of these individual condensation steps is likewise determined by the polyketide synthase. Structural comparisons and studies with incorporation of radioactive acetate and propionate have shown that the sequence of acetate and propionate incorporation for the various ansamycins takes place in accordance with a scheme which appears to be identical or very similar in the first condensation steps. Thus, from a common synthesis scheme of the ansamycin polyketide synthases (the rifamycin synthesis scheme), the syntheses of the various ansamycins sooner or later branch off, in accordance with their structural difference from the rifamycin structure, into side branches of the synthesis (Ghisalba et al., Biotechnology of Industrial Antibiotics Vandamme E. J. Ed., Decker Inc. New York, (1984) 281–327).

Because of the great structural variety of the rifamycins and their specific and interesting biological effect, there is great interest in understanding the genetic basis of their synthesis in order to create the possibility of specifically influencing it. This is particularly desirable because, as explained above, there is much in common between the synthesis of rifamycins and that of other ansamycins. This similarity in the biosynthesis, which probably derives from a common evolutionary origin of this metabolic pathway, naturally has a genetic basis.

The genetic basis of secondary metabolite biosynthesis essentially exists in the genes which code for the individual biosynthetic enzymes, and in the regulatory elements which control the expression of the biosynthesis genes. The secondary metabolite synthesis genes of *actinomycetes* have hitherto been found as clusters of adjacent genes in all the systems investigated. The size of such antibiotic gene clusters extends from about 10 kilobases (kb) up to more than 100 kb. The clusters often contain specific regulator genes and genes for resistance of the producer organism to its own antibiotic (Chater, Ciba Found. Symp. (1992), 171, 144–162).

The invention described herein has now succeeded, by identifying and cloning genes of rifamycin biosynthesis, in creating the genetic basis for synthesizing by genetic methods rifamycin analogues or novel ansamycins which combine structural elements from rifamycin with other ansamycins. This also creates the basis for preparing novel collections of substances based on the rifamycin biosynthesis gene cluster by combinatorial biosynthesis.

It was possible in a first step to identify and clone a DNA fragment from the genome of *A. mediterranei*, which shows homology with known polyketides synthase genes. After obtaining the sequence information from this DNA fragment which confirmed a typical sequence for polyketide synthases it was possible to screen a cosmid library of *A. mediterranei* with specific DNA probes derived from this fragment in a screening program for further DNA fragments which are involved in the rifamycin gene cluster. As a result, the complete rifamycin polyketide synthase gene cluster was identified and subjected to sequence determination (see SEQ ID NO 3). The gene cluster comprises six open reading frames, which are referred to hereinafter as ORF A, B, C, D, E and F and which code for the proteins and polypeptides depicted in SEQ ID NOS 4 to 9.

The gene cluster isolated and characterized in this way represents the basis, for example, for targeted optimization of the production of rifamycin, ansamycins or analogues thereof. Examples of techniques and possible areas of application available in this connection are as follows:

Overexpression of individual genes in producer strains with plasmid vectors or by incorporation into the chromosome.

Study of the expression and transcriptional regulation of the gene cluster during fermentation with various producer strains and optimization thereof through physiological parameters and appropriate fermentation conditions.

Identification of regulatory genes and of the DNA binding sites of the corresponding regulatory proteins in the gene cluster. Characterization of the effect of these regulatory elements on the production of rifamycins or ansamycins; and influencing them by specific mutation in these genes or the DNA binding sites.

Duplication of the complete gene cluster or parts thereof in producer strains.

Besides these applications of the gene cluster to improve production by fermentation as described above, it can likewise be employed for the biosynthetic preparation of novel rifamycin analogues or novel ansamycins or ansamycin-like compounds in which the aliphatic bridge is connected at only one end to the aromatic nucleus. The following possibilities come into consideration here, for example:

Inactivation of individual steps in the biosynthesis, for example by gene disruption.

Mutation of individual steps in the biosynthesis, for example by gene replacement.

Use of the cluster or fragments thereof as DNA probe in order to isolate other natural microorganisms which produce metabolites similar to rifamycin or ansamycins.

Exchange of individual elements in this gene cluster by those from other gene clusters.

Use of modified polyketide synthases for setting up libraries of various rifamycin analogues or ansamycins, which are then tested for their activity (Jackie & Khosla, Chemistry & Biology, (1995), 2, 355–362).

Construction of mutated *actinomycetes* strains from which the natural rifamycin or ansamycin biosynthesis gene cluster in the chromosome has been partly or completely deleted, and can thus be used for expressing genetically modified gene clusters.

Exchange of individual elements within the gene cluster.

DETAILED DESCRIPTION OF THE INVENTION

The invention relates to a DNA fragment from the genome of *Amycolatopsis mediterranei*, which comprises a DNA region which is involved directly or indirectly in the gene cluster responsible for rifamycin synthesis; and the adjacent DNA regions; and functional constituents or domains thereof.

The DNA fragments according to the invention may moreover comprise regulatory sequences such as promoters, repressor or activator binding sites, repressor or activator genes, terminators; or structural genes. Likewise part of the invention are any combinations of these DNA fragments with one another or with other DNA fragments, for example combinations of promoters, repressor or activator binding sites and/or repressor or activator genes from an ansamycin gene cluster, in particular from the rifamycin gene cluster, with foreign structural genes or combinations of structural genes from the ansamycin gene cluster, especially the rifamycin gene cluster, with foreign promoters; and combinations of structural genes with one another or with gene fragments which code for enzymatically active domains and are from various ansamycin biosynthesis systems. Foreign structural genes, and foreign gene fragments coding for enzymatically active domains, code, for example, for proteins involved in the biosynthesis of other ansamycins.

A preferred DNA fragment is one directly or indirectly involved in the gene cluster responsible for rifamycin synthesis.

The gene cluster or DNA region described above contains, for example, the genes which code for the individual enzymes involved in the biosynthesis of ansamycins and, in particular, of rifamycin, and the regulatory elements which control the expression of the biosynthesis genes. The size of such antibiotic gene clusters extends from about 10 kilobases (kb) up to over 100 kb. The gene clusters normally comprise specific regulatory genes and genes for resistance of the producer organism to its own antibiotic. Examples of what is meant by enzymes or enzymatically active domains involved in this biosynthesis are those necessary for synthesizing, starting from 3-amino-5-hydroxybenzoic acid, the ansamycins such as rifamycin, for example polyketide synthases, acyltransferases, dehydratases, ketoreductases, acyl carrier proteins or ketoacyl synthases.

Thus, the complete sequence of the gene cluster shown in SEQ ID NO 3, as well as DNA fragments which comprise sequence portions which code for a polyketide synthase or an enzymatically active domain thereof, are particularly preferred. Examples of such preferred DNA fragments are, for example, those which code for one or more of the proteins and polypeptides depicted in SEQ ID ID NOS 4, 5, 6, 7, 8 and 9, or functional derivatives thereof, also including partial sequences thereof which comprise, for example, 15 or more consecutive nucleotides. Other preferred embodiments relate to DNA regions of the gene cluster according to the invention or fragments thereof, like those present in the deposited clones pNE95, pRi44-2 and pNE112, or derived therefrom. Further preferred DNA fragments are those comprising sequence portions which display homologies with the sequences comprised by the clones pNE95, pRi44-2 and/or pNE112 or with SEQ ID ID NOS 1 and/or 3, and therefore can be used as hybridization probe within a genomic gene bank of an ansamycin-, in particular, rifamycin-producing organism for finding constituents of the corresponding gene cluster. The DNA fragment may moreover, for example, comprise exclusively genomic DNA. A particularly preferred DNA fragment is one which comprises the nucleotide sequence depicted in SEQ ID NO 1 or 3, or partial sequences thereof, which, by reason of homologies, can be regarded as structural or functional equivalent to said sequence or partial sequence therefrom, and which therefore are able to hybridize with this sequence.

The DNA fragments according to the invention comprise, for example, sequence portions which comprise homologies with the above-described enzymes, enzyme domains or fragments thereof.

The term homologies and structural and/or functional equivalents refers primarily to DNA and amino acid sequences with few or minimal differences between the relevant sequences. These differences may have very diverse causes. Thus, for example, this may entail mutations or strain-specific differences which occur naturally or are artificially induced. Or the differences observed from the initial sequence are derived from a targeted modification, which can be introduced, for example, during a chemical synthesis.

Functional differences can be regarded as minimal if, for example, the nucleotide sequence coding for a polypeptide or a protein sequence has essentially the same characteristic properties as the initial sequence, whether in respect of enzymatic activity, immunological reactivity or, in the case of a nucleotide sequence, gene regulation.

Structural differences can be regarded as minimal as long as there is a significant overlap or similarity between the various sequences, or they have at least similar physical properties. The latter include, for example, the electrophoretic mobility, chromatographic similarities, sedimentation coefficients, spectrophotometric properties etc.

In the case of nucleotide sequences, the agreement should be at least 70%, but preferably 80% and very particularly preferably 90% or more. In the case of the amino acid sequence, the corresponding figures are at least 50%, but preferably 60% and particularly preferably 70%. 90% agreement is very particularly preferred.

The invention furthermore relates to a method for identifying, isolating and cloning one of the DNA fragments described above. A preferred method comprises, for example, the following steps:

a) setting up of a genomic gene bank,
b) screening of this gene bank with the assistance of the DNA sequences according to the invention, and
c) isolation of the clones identified as positive.

A general method for identifying DNA fragments involved in the biosynthesis of ansamycins comprises, for example, the following steps 1) Cloning of a DNA fragment which shows homology with known polyketide synthase genes.
   a) The presence of DNA fragments having homology with the polyketide synthase genes according to the invention is detected in the strains of the microorganism to be investigated by a Southern experiment with chromosomal DNA of this strain. The size of such homologous DNA fragments can be determined by digesting the DNA with a suitable restriction enzyme.
   b) Production of a plasmid gene bank comprising the above digested chromosomal fragments. Normally, individual clones of this gene bank are tested once again for homology with the polyketide synthase genes according to the invention. Clones with recombinant plasmids comprising fragments having homology with the polyketide probe are then normally isolated on the basis of this homology.
2) Analysis of the cloned region
   a) Restriction analysis of the isolated recombinant plasmids and checking of the identity of these cloned fragments with one another.
   b) By a chromosomal Southern with DNA of the original microorganism and the isolated DNA fragment as probe it can be demonstrated that the cloned fragment is an original chromosomal DNA fragment from the original microorganism.
   c) It is possible as an option to demonstrate a significant homology of the cloned DNA fragment with chromosomal DNA from other ansamycin producers (streptovaricin, tolypomycin, geldanamycin, ansamitocin). This would confirm that the cloned DNA is typical of gene clusters of ansamycin biosynthesis and thus also of rifamycin biosynthesis.
   d) DNA sequencing of an internal restriction fragment and demonstration by comparative sequence analysis that the cloned region is a typical DNA sequence of polyketide synthases, coding for the biosynthesis of polyketide antibiotics from *actinomycetes*.
3) Isolation and characterization of adjacent DNA regions
   a) Construction of a cosmid gene bank from the original microorganism and analysis thereof for homology with the isolated fragments. Isolation of cosmids having homology with this fragment.
   b) Demonstration by restriction analysis that the isolated cosmid clones comprise a DNA region of the original microorganism which overlaps with the original fragment.

As described above, the first step in the isolation of the DNA fragments according to the invention is normally the setting up of genomic gene banks from the organism of interest, which synthesize the required ansamycin, especially rifamycin.

Genomic DNA can be obtained from a host organism in various ways, for example by extraction from the nuclear fraction and purification of the extracted DNA by known methods.

The fragmentation, which is necessary for setting up a representative gene bank, of the genomic DNA to be cloned to a size which is suitable for insertion into a cloning vector can take place either by mechanical shearing or else, preferably, by cutting with suitable restriction enzymes.

Suitable cloning vectors, which are already in routine use for producing genomic gene libraries, comprise, for example, cosmid vectors, plasmid vectors or phage vectors.

It is then possible in a screening program to obtain suitable clones which comprise the required gene(s) or gene fragment(s) from the gene libraries produced in this way.

One possibility for identifying the required DNA region consists in, for example, using the gene bank described above to transform strains which, because of a blocked synthetic pathway, are unable to produce ansamycins, and identifying those clones which are again able after the transformation to produce ansamycin (revertants). The vectors which lead to revertants comprise a DNA fragment which is required in ansamycin synthesis.

Another possibility for identifying the required DNA region is based, for example, on using suitable probe molecules (DNA probe) which are obtained for example as described above. Various standard methods are available for identifying suitable clones, such as differential colony hybridization or plaque hybridization.

It is possible to use as probe molecule a previously isolated DNA fragment from the same or a structurally related gene or gene cluster which, because of the homologies present, is able to hybridize with the corresponding sequence section within the required gene or gene cluster to be identified. Preferably used as probe molecule for the purpose of the present invention is a DNA fragment obtainable from a gene or a DNA sequence involved in the synthesis of polyketides such as ansamycins or soraphens.

If the nucleotide sequence of the gene to be isolated, or at least parts of this sequence, are known, it is possible in an alternative embodiment to use, based on this sequence information, a corresponding synthesized DNA sequence for the hybridizations or PCR amplifications.

In order to facilitate detectability of the required gene or else parts of a required gene, one of the DNA probe molecules described above can be labelled with a suitable, easily detectable group. A detectable group for the purpose of this invention means any material which has a particular, easily identifiable, physical or chemical property.

Particular mention may be made at this point of enzymatically active groups such as enzymes, enzyme substrates, coenzymes and enzyme inhibitors, furthermore fluorescent and luminescent agents, chromophores and radioisotopes such as $^3H$, $^{35}S$, $^{32}P$, $^{125}I$ and $^{14}C$. Easy detectability of these markers is based, on the one hand, on their intrinsic physical properties (for example fluorescent markers, chromophores, radioisotopes) or, on the other hand, on their reaction and binding properties (for example enzymes, substrates, coenzymes, inhibitors). Materials of these types are already widely used in particular in immunoassays and, in most cases, can also be used in the present application.

General methods relating to DNA hybridization are described, for example, by Maniatis T. et al., Molecular Cloning, Cold Spring Harbor Laboratory Press (1982).

Those clones within the previously described gene libraries which are able to hybridize with a probe molecule and which can be identified by one of the abovementioned detection methods can then be further analysed in order to determine the extent and nature of the coding sequence in detail.

An alternative method for identifying cloned genes is based on constructing a gene library consisting of plasmid or expression vectors. This entails, in analogy to the methods described previously, the genomic DNA comprising the required gene being initially isolated and then cloned into a suitable plasmid or expression vector. The gene libraries produced in this way can then be screened by suitable procedures, for example by use of complementation studies, and those clones which comprise the required gene or else at least a part of this gene as insert can be selected.

It is thus possible with the aid of the methods described above to isolate a gene, several genes or a gene cluster which code for one or more particular gene products.

For further characterization, the DNA sequences purified and isolated in the manner described above are subjected to restriction analysis and sequence analysis.

For sequence analysis, the previously isolated DNA fragments are first fragmented using suitable restriction enzymes, and then cloned into suitable cloning vectors. In order to avoid mistakes in the sequencing, it is advantageous to sequence both DNA strands completely.

Various alternatives are available for analysing the cloned DNA fragment in respect of its function within ansamycin biosynthesis.

Thus, for example, it is possible in complementation experiments with defective mutants not only to establish involvement in principle of a gene or gene fragment in secondary metabolite biosynthesis, but also to verify specifically the synthetic step in which said DNA fragment is involved.

In an alternative type of analysis, evidence is obtained in exactly the opposite way. Transfer of plasmids which comprise DNA sections which have homologies with appropriate sections on the genome results in integration of said homologous DNA sections via homologous recombination. If, as in the present case, the homologous DNA section is a region within an open reading frame of the gene cluster, plasmid integration results in inactivation of this gene by so-called gene disruption and, consequently, in an interruption in secondary metabolite production. It is assumed according to current knowledge that a homologous region which comprises at least 100 bp, but preferably more than 1000 bp, is sufficient to bring about the required recombination event.

However, a homologous region which extends over a range of from 0.3 to 4 kb, but in particular over a range of from 1 to 3 kb, is preferred.

To prepare suitable plasmids which have sufficient homology for integration via homologous recombination there is preferably provision of a subcloning step in which the previously isolated DNA is digested, and fragments of suitable size are isolated and subsequently cloned into a suitable plasmid. Examples of suitable plasmids are the plasmids generally used for genetic manipulations in *streptomycetes* or *E. coli*.

It is possible in principle to use for the preparation and multiplication of the previously described constructs all conventional cloning vectors such as plasmid or bacteriophage vectors as long as they have replication and control sequences derived from species compatible with the host cell.

The cloning vector usually has an origin of replication plus specific genes which result in phenotypical selection features in the transformed host cell, in particular resistances to antibiotics. The transformed vectors can be selected on the basis of these phenotypica markers after transformation in a host cell.

Selectable phenotypical markers which can be used for the purpose of this invention comprise, for example, without this representing a limitation of the subject-matter of the invention, resistances to thiostrepton, ampicillin, tetracycline, chloramphenicol, hygromycin, G418, kanamycin, neomycin and bleomycin. Another selectable marker can be, for example, prototrophy for particular amino acids.

Mainly preferred for the purpose of the present invention are *streptomycetes* and *E. coli* plasmids, for example the plasmids used for the purpose of the present invention.

Host cells primarily suitable for the previously described cloning for the purpose of this invention are prokaryotes, including bacterial hosts such as *streptomycetes, actinomycetes, E. coli* or *pseudomonads*.

*E. coli* hosts are particularly preferred, for example the *E. coli* strain HB101 or X-1 blue MR® (Stratagene) or *streptomyces* such as the plasmid-free strains of *Streptomyces lividans* TK23 and TK24.

Competent cells of the *E. coli* strain HB101 are produced by the methods normally used for transforming *E. coli*. The transformation method of Hopwood et al. (Genetic manipulation of streptomyces a laboratory manual. The John Innes Foundation, Norwich (1985)) is normally used for *streptomyces*.

After transformation and subsequent incubation on a suitable medium, the resulting colonies are subjected to a differential screening by plating out on selective media. It is then possible to isolate the appropriate plasmid DNA from those colonies which comprise plasmids with DNA fragments cloned in.

The DNA fragment according to the invention, which comprises a DNA region which is involved directly or indirectly in the biosynthesis of ansamycin and can be obtained in the previously described manner from the ansamycin biosynthesis gene cluster, can also be used as starter clone for identifying and isolating other adjacent DNA regions overlapping therewith from said gene cluster.

This can be achieved, for example, by carrying out a so-called chromosome walking within a gene library consisting of DNA fragments with mutually overlapping DNA regions, using the previously isolated DNA fragment or else, in particular, the sequences located at its 5' and 3' margins. The procedures for chromosome walking are known to the person skilled in this art. Details can be found, for example, in the publications by Smith et al. (Methods Enzymol (1987), 151, 461–489) and Wahl et al. (Proc Natl. Acad. Sci, USA (1987), 84, 2160–2164).

The prerequisite for chromosome walking is the presence of clones having coherent DNA fragments which are as long as possible and mutually overlap within a gene library, and a suitable starter clone which comprises a fragment which is located in the vicinity or else, preferably, within the region to be analysed. If the exact location of the starter clone is unknown, the walking is preferably carried out in both directions.

The actual walking step starts by using the identified and isolated starter clone as probe in one of the previously described hybridization reactions in order to detect adjacent clones which have regions overlapping with the starter clone. It is possible by hybridization analysis to establish which fragment projects furthest over the overlapping region. This is then used as starting clone for the 2nd walking step, in which case there is establishment of the fragment which overlaps with said 2nd clone in the same direction. Continuous progression in this manner on the chromosome results in a collection of overlapping DNA clones which cover a large DNA region. These can then, where appropriate after one or more subcloning steps, be ligated together by known methods to give a fragment which comprises parts or else, preferably all of the constituents essential for ansamycin biosynthesis.

The hybridization reaction to establish clones with overlapping marginal regions preferably makes use not of the very large and unwieldy complete fragment but, in its place, a partial fragment from the left or right marginal region, which can be obtained by a subcloning step. Because of the smaller size of said partial fragment, the hybridization reaction results in fewer positive hybridization signals, so that the analytical effort is distinctly less than on use of the complete fragment. It is furthermore advisable to characterize the partial fragment in detail in order to preclude its comprising larger amounts of repetitive sequences, which may be distributed over the entire genome and thus would greatly impede a targeted sequence of walking steps.

Since the gene cluster responsible for ansamycin biosynthesis covers a relatively large region of the genome, it may also be advantageous to carry out a so-called large-step walking or cosmid walking. It is possible in these cases, by using cosmid vectors which permit the cloning of very large DNA fragments, to cover a very large DNA region, which may comprise up to 42 kb, in a single walking step.

In one possible embodiment of the present invention, for example, to construct a cosmid gene bank from *streptomycetes* or *actinomycetes,* complete DNA is isolated with the size of the DNA fragments being of the order of about 100 kb, and is subsequently partially digested with suitable restriction endonucleases.

The digested DNA is then extracted in a conventional way in order to remove endonuclease which is still present, and is precipitated and finally concentrated. The resulting fragment concentrate is then fractionated, for example by density gradient centrifugation, in accordance with the size of the individual fragments. After the fractions obtainable in this way have been dialysed they can be analysed on an agarose gel. The fractions which contain fragments of suitable size are pooled and concentrated for further processing. Fragments to be regarded as particularly suitable for the purpose of this invention have a size of the order of 30 kb to 42 kb, but preferably of 35 kb to 40 kb.

In parallel with the fragmentation described above, or later, for example a suitable cosmid vector pWE15® (Stratagene) is completely digested with a suitable restriction enzyme, for example BamHI, for the subsequent ligase reaction.

Ligation of the cosmid DNA to the *streptomyces* or *actinomycetes* fragments which have been fractionated according to their size can be carried out using a T4 DNA ligase. The ligation mixture obtainable in this way is, after a sufficient incubation time, packaged into λ phages by generally known methods.

The resulting phage particles are then used to infect a suitable host strain. A recA⁻ *E. coli* strain is preferred, such as *E. coli* HB101 or X-1 Blue® (Stratagene). Selection of transfected clones and isolation of the plasmid DNA can be carried out by generally known methods.

The screening of the gene bank for DNA fragments which are involved in ansamycin biosynthesis is carried out, for example, using a specific hybridization probe which is assumed (for example on the basis of DNA sequence or DNA homology or complementation tests or gene disruption or the function thereof in other organisms) to comprise DNA regions from the 'ansamycin gene cluster'.

A plasmid which comprises an additional fragment of the required size or has been identified on the basis of hybridizations can then be isolated from the gel in the previously described manner. The identity of this additional fragment with the required fragment of the previously selected cosmid can then be confirmed by Southern transfer and hybridization.

Function analysis of the DNA fragments isolated in this way can be carried out in a gene disruption experiment as described above.

Another possible use of the DNA fragments according to the invention is to modify or inactivate enzymes or domains involved in ansamycin and, in particular, rifamycin biosynthesis, or to synthesize oligonucleotides which are then in turn used for finding homologous sequences in PCR amplification.

Besides the DNA fragments according to the invention as such, also claimed are their use firstly for producing rifamycin, rifamycin analogues or precursors thereof, and for the biosynthetic production of novel ansamycins or of precursors thereof. Included in this connection are those molecules in which the aliphatic bridge is connected only at one end to the aromatic nucleus.

The DNA fragments according to the invention permit, for example, by combination with DNA fragments from other biosynthetic pathways or by inactivation or modification thereof, the biosynthesis of novel hybrid compounds, in particular of novel ansamycins or rifamycin analogues. The steps necessary for this are generally known and are described, for example, in Hopwood, Current Opinion in Biotechnol. (1993), 4,531–537.

The invention furthermore relates to the use of the DNA fragments according to the invention for carrying out the novel technology of combinatorial biosynthesis for the biosynthetic production of libraries of polyketide synthases based on the rifamycin and ansamycin biosynthesis genes. If, for example, several sets of modifications are produced, it is possible in this way to produce, by means of biosyntheses, a library of polyketides, for example ansamycins or rifamycin analogues, which then needs to be tested only for the activity of the compounds produced in this way. The steps necessary for this are generally known and are described, for example, in Tsoi and Khosla, Chemistry & Biology (1995), 2, 355–362 and WO-9508548.

Besides the DNA fragment as such, also claimed is its use for the genetic construction of mutated *actinomycetes* strains from which the natural rifamycin or ansamycin biosynthesis gene cluster in the chromosome has been partly or completely deleted, and which can thus be used for expressing genetically modified ansamycin or rifamycin biosynthesis gene clusters.

The invention furthermore relates to a hybrid vector which comprises at least one DNA fragment according to the invention, for example a promoter, a repressor or activator binding site, a repressor or activator gene, a structural gene, a terminator or a functional part thereof. The hybrid vector comprises, for example, an expression cassette which comprises a DNA fragment according to the invention which is able to express one or more proteins involved in ansamycin biosynthesis and, in particular in rifamycin biosynthesis, or a functional fragment thereof. The invention likewise relates to a host organism which comprises the hybrid vector described above.

Suitable vectors representing the starting point of the hybrid vectors according to the invention, and suitable host organisms such as bacteria or yeast cells are generally known.

The host organism can be transformed by generally customary methods such as by means of protoplasts, $Ca^{2+}$, $Cs^+$, polyethylene giycol, electroporation, viruses, lipid vesicles or a particle gun. The DNA fragments according to the invention may then be present both as extrachromosomal constituents in the host organism and integrated via suitable sequence sections into the chromosome of the host organism.

The invention likewise relates to polyketide synthases which comprise the DNA fragments according to the invention, in particular those from *Amycolatopsis mediterranei* which are involved directly or indirectly in rifamycin synthesis, and functional constituents thereof, for example enzymatically active domains.

The invention furthermore relates to a hybridization probe comprising a DNA fragment according to the invention, and to the use thereof, in particular for identifying DNA fragments involved in the biosynthesis of ansamycins.

In order to obtain unambiguous signals in the hybridization, DNA bound to the filter (for example made of nylon or nitrocellulose) is normally washed at 55–65° C. in 0.2×SSC (1×SSC=0.15 M sodium chloride, 15 mM sodium citrate).

EXAMPLES

General

General molecular genetic techniques such as DNA isolation and purification, restriction digestion of DNA, agarose gel electrophoresis of DNA, ligation of restriction fragments, cultivation and transformation of *E. coli*, plasmid isolation from *E. coli*, are carried out as described in Maniatis et al., Molecular Cloning: A laboratory manual, 1st Edit. Cold Spring Harbor Laboratory Press, Cold Spring Harbor N.Y. (1982).

Culture conditions and molecular genetic techniques with *A. mediterranei* and other *actinomycetes* are as described by Hopwood et al. (Genetic manipulation of *streptomyces* a laboratory manual, The John Innes Foundation, Norwich, 1985). All liquid cultures of *A. mediterranei* and other *actinomycetes* are carried out in Erlenmeyer flasks at 28° C. on a shaker at 250 rpm.

Nutrient Media Used:

L B Maniatis et al., Molecular Cloning: A laboratory manual, 1st Edit. Cold Spring Harbor Laboratory Press, Cold Spring Harbor N.Y. (1982)

NL148Schupp+Divers FEMS Microbiology Lett. 36, 159–162 (1986) (NL148=NL148G without glycine)

R2YE Hopwood et al. (Genetic manipulation of *streptomyces* a laboratory manual. The John Innes Foundation, Norwich, 1985)

| TB: | 12 g/l | Bacto tryptone |
|---|---|---|
| | 24 g/l | Bacto yeast extract |
| | 4 ml/l | glycerol |

Example 1

Detection of Chromosomal DNA Fragments from *A. mediterranei* Having Homology with Polyketide Synthase Genes of Other Bacteria To obtain genomic DNA from *A. mediterranei*, cells of the strain *A. mediterranei* wt3136 (=LBGA 3136, ETH collection of strains) are cultivated in NL148 medium for 48 hours. 1 ml of this culture is then transferred into 50 ml of NL148 medium (+2.5 g/l glycine) in a 200 ml Erlenmeyer flask, and the culture is incubated for 48 h. The cells are removed from the medium by centrifugation at 3000 g for 10 min. and are resuspended in 5 ml of SET (75 mM NaCl, 25 mM EDTA, 20 mM Tris, pH 7.5). High molecular weight DNA is extracted by the method of Pospiech and Neumann (Trends in Genetics (1995), 11, 217–218).

In order to detect, by a Southern blot, individual fragments from the isolated *A. mediterranei* DNA which have homology with polyketide synthase genes, a radioactive DNA probe is prepared from a known polyketide synthase gene cluster. To do this, the PvuI fragment 3.8 kb in size is isolated from the recombinant plasmid p98/1 (Schupp et al. J. of Bacteriol. (1995), 177, 3673–3679), which comprises a DNA region, about 32 kb in size, from the polyketide synthase for the antibiotic soraphen A. About 0.5 µg of the isolated 3.8 kb PvuI DNA fragment is radiolabelled with $^{32}$P-d-CTP by the nick translation system from Gibco/BRL (Basle) in accordance with the manufacturer's instructions.

For the Southern blot, about 2 µg of the genomic DNA isolated above from A. mediterranei are completely digested with the restriction enzyme BgIII (Böhringer, Mannheim), and the resulting fragments are fractionated on a 0.8% agarose gel. A Southern blot with this agarose gel and the DNA probe isolated above (3.8 kb PvuI fragment) detects a DNA BgIII-cut fragment which is about 13 kb in size from the genomic DNA of A. mediterranei, and which has homology with the DNA probe used. It can be concluded on the basis of this homology that the detected DNA fragment from A. mediterranei is a genetic region which codes for a polyketide synthase and thus is involved in the synthesis of a polyketide antibiotic.

Example 2

Production of a Specific Recombinant Plasmid Collection Comprising BgIII-digested Chromosomal Fragments from A. mediterranei 12–16 kb in Size The E. coli positive selection vector pIJ4642 (derivative of pIJ666, Kieser & Melton, Gene (1988), 65, 83–91) developed at the John Innes Centre (Norwich, UK) is used to produce the plasmid gene bank. This plasmid is first cut with BamHI, and the two resulting fragments are fractionated on an agarose gel. The smaller of the two fragments is the filler fragment of the vector and the larger is the vector portion which, on self-ligation after deletion of the filler fragment, forms, owing to the flanking fd termination sequences, a perfect palindrome, which means that the plasmid cannot be obtained as such in E. coli. This vector portion 3.8 kb in size is isolated from the agarose gel by electroelution as described on page 164–165 of Maniatis et al., Molecular Cloning: A laboratory manual, 1st Edit. Cold Spring Harbor Laboratory Press, Cold Spring Harbor N.Y. (1982).

To prepare the BgIII-cut DNA fragments from A. mediterranei, the high molecular weight genomic DNA prepared in Example 1 is used. About 10 µg of this DNA are completely digested with the restriction enzyme BgIII and subsequently fractionated on a 0.8% agarose gel. DNA fragments with a size of about 12–16 kb are cut out of the gel and detached from the gel block by electroelution (see above). About 1 µg of the BgIII fragments isolated in this way is ligated to about 0.1 µg of the BamHI portion, isolated above, of the vector pIJ4642. The ligation mixture obtained in this way is then transformed into the E. coli strain HB101 (Stratagene). About 150 transformed colonies are selected from the transformation mixture on LB agar with 30 µg per ml chloramphenicol. These colonies contain recombinant plasmids with BgIII-cut genomic DNA fragments from A. mediterranei in the size range 12–16 kb.

Example 3

Cloning and Characterization of Chromosomal A. mediterranei DNA Fragments Having Homology with Bacterial Polyketide Synthase Genes 150 of the plasmid clones prepared in Example 2 are analysed by colony hybridization using a nitrocellulose filter (Schleicher & Schuell) as described on pages 318–319 of Maniatis et al., Molecular Cloning: A laboratory manual, 1st Edit. Cold Spring Harbor Laboratory Press, Cold Spring Harbor N.Y. (1982). The DNA probe used is the 3.8 kb PvuI fragment, radiolabelled with $^{32}$P-d-CTP and isolated in Example 1, of the plasmid p98/1. The plasmids are isolated from 5 plasmid clones which show a hybridization signal, and are characterized by two restriction digestions with the enzymes HindIII or KpnI. HindIII cuts twice in the vector portion of the clones, 0.3 kb to the right and left of the BamHI cleavage site into which the A. mediterranei DNA has been integrated. KpnI does not cut in the pIJ 4642 vector portion. This restriction analysis shows that the investigated clones comprise both identical HindIII fragments of about 14 and 3.1 kb and identical KpnI fragments approximately 11.4 kb and 5.7 kb in size. This shows that these clones comprise the same genomic BgIII fragment of A. mediterranei, and that the latter has a size of about 13 kb. It can additionally be concluded from this restriction analysis that this cloned BgIII fragment has no internal HindIII cleavage site, but has 2 KpnI cleavage sites which afford an internal KpnI fragment 5.7 kb in size.

The plasmid DNA of the above 5 clones with identical restriction fragments is further characterized by a Southern blot. For this purpose, the plasmids are cut with HindIII and KpnI, and the DNA probe used is the $^{32}$P-radiolabelled 3.8 kb PvuI fragment of the plasmid p98/1 used above. This experiment confirms that the 5 plasmids contain identical A. mediterranei DNA fragments and that these have significant homology with the DNA probe which is characteristic of bacterial polyketide synthase genes. In addition, the Southern blot shows that the internal KpnI fragment 5.7 kb in size likewise has significant homology with the DNA probe used. The plasmid called pRi7-3 is selected from the 5 plasmids for further processing.

To demonstrate that the cloned BgIII fragment about 13 kb in size from A. mediterranei is an original chromosomal DNA fragment, another Southern blot is carried out. Chromosomal DNA from A. mediterranei which has been cut with BgIII, KpnI or BamHI is employed in this blot. Two BamHI fragments which are about 1.8 and 1.9 kb in size and are present in the 5.7 kb KpnI fragment of pRi7-3 are used as radiolabelled DNA probe. This experiment confirms that the BgIII DNA fragment about 13 kb in size cloned in the recombinant plasmid pRi7-3 is an authentic genomic DNA fragment from A. mediterranei. In addition, this experiment confirms that the cloned fragment comprises an internal KpnI fragment 5.7 kb in size and two BamHI fragments about 1.8 and 1.9 kb in size, and that these DNA fragments are likewise authentic genomic DNA fragments from A. mediterranei.

Example 4

Demonstration of a Significant Homology of the Cloned Genomic 13 kb BgIII Fragment from A. mediterranei with Chromosomal DNA from Other Actinomycetes which Produce Ansamycins Demonstration of a significant homology between the cloned chromosomal DNA region of A. mediterranei and chromosomal DNA from other ansamycin-producing actinomycetes takes place by a Southern blot experiment. The following ansamycin-producing strains are employed for this purpose (the ansamycins produced by the strains are in parentheses): Streptomyces spectabilis (streptovaricins), Streptomyces tolypophorus (tolypomycins), Streptomyces hygroscopicus (geldanamycins), Nocardia species ATCC31281 (ansamitocins). Genomic DNA from these strains is isolated as described for *A. mediterranei* in Example 1 and digested with the restriction enzyme KpnI, and the restriction fragments obtained in this way are fractionated on an agarose gel for the Southern blot. Two BamHI fragments about 1.8 and 1.9 kb in size from *A. mediterranei*, which are used in Example 3 and are isolated from the plasmid pRi7-3, are used as radioactive probe. This experiment shows that these ansamycin-producing strains have a significant DNA homology with the DNA probe used and thus with the cloned chromosomal region of *A. mediterranei*. It is to be observed in this connection that the homology in the case of producers of ansamycins with a naphthoquinoid ring system (streptovaricin, tolypomycin) is greater than in the case of those with a benzoquinoid ring system (geldanamycin, ansamitocin). This result suggests that the cloned chromosomal DNA region from *A. mediterranei* is typical of ansamycin biosynthesis gene clusters and, especially, of gene clusters for ansamycins with naphthoquinoid ring systems, corresponding to the ring system in rifamycins.

Example 5

DNA Sequence Determination of the KpnI Fragment 5.7 kb in Size Located Within the cloned 13 kb BalII Fragment For the sequencing, the 5.7 kb KpnI fragment is isolated from the plasmid pRi7-3 (DSM 11114) (Maniatis et. al. 1992) and subcloned into the KpnI cleavage site of the vector pBRKanf4, which is suitable for the DNA sequencing, affording the plasmids pTS004 and pTS005. The vector pBRKanf4 (derived from pBRKanf1; Bhat, Gene (1993) 134, 83–87) is suitable for introducing sequential deletions of Sau3A fragments in the cloned insert fragment, because this vector does not itself have a GATC nucleotide sequence. In addition, the BamHI fragments 1.9 and 1.8 kb in size present in the 5.7 kb KpnI fragment are subcloned into the BamHI cleavage site of pBRKanf4, resulting the plasmids pTS006 and pTS007, and pTS008 and pTS009, respectively.

To prepare subclones sequentially truncated by Sau3A fragments for the DNA sequencing, the plasmids pTS004 to pTS009 are partially digested with Sau3A and completely digested with XbaI or HindIII (a cleavage site in the multiple cloning region of the vector). The DNA obtained in this way (consisting of the linearized vector with inserted DNA fragments truncated by Sau3A fragments) is filled in at the ends using Klenow polymerase (fragment of polymerase I, see Maniatis et al. pages 113–114), self-ligated with T4 DNA ligase and transformed into *E. coli* DH5α. The plasmid DNA which corresponds to the pTS004 to pTS009 plasmids, but has DNA regions, which are truncated from one side by Sau3A fragments, from the original integrated fragments of *A. mediterranei*, is isolated from individual transformed clones obtained in this way.

The DNA sequencing is carried out with the plasmids obtained in this way and with pTS004 to pTS009 using the reaction kit from Perkin-Elmer/Applied Biosystems with dye-labelled terminator reagents (Kit N° 402122) and a universal primer or a T7 primer. A standard cycle sequencing protocol with a thermocycler (MJ Research DNA Engine Thermocycler, Model 225) is used, and the sequencing reactions are analysed by the Applied Biosystems automatic DNA sequencer (Modell 373 or 377) in accordance with the manufacturer's instructions. To analyse the results, the following computer programs (software) are employed: Applied Biosystems DNA analysis software, Unix Solaris CDE software, DNA assembly and analysis package GAP licensed from R. Staden (Nucleic Acid Research (1995)23, 1406–1410) and Blast (NCBI).

The methods described above can be used to sequence completely both DNA strands of the 5.7 kb KpnI fragment from *A. mediterranei* strain wt3136. The DNA sequence of the 5.7 kb fragment with a length of 5676 base pairs is depicted in SEQ ID NO 1.

Example 6

Analysis of the Protein-encoding Region (Genes) on the 5.7 kb KpnI Fragment from *A. mediterranei*

The nucleotide sequence of the 5.7 kb KpnI fragment is analysed using the Codonpreference computer program (Genetics Computer Group, University of Wisconsin, 1994). This analysis shows that this fragment is over its whole length a protein-encoding region and thus forms part of a larger open reading frame (ORF). The codons used in this ORF are typical of *streptomycetes* and *actinomycetes* genes. The amino acid sequence derived from the DNA sequence from this ORF is depicted in SEQ ID NO 2.

Polyketide synthases for macrolide antibiotics (such as erythromycin, rapamycin) are very large multifunctional proteins which comprise several enzymatically active domains which are now well characterized (Hopwood und Khosla, Ciba Foundation Symposium (1992), 171, 88–112; Donadio and Katz, Gene (1992), 111, 51–60; Schwecke et al., Proc. Natl. Acad. Sci. U.S.A. (1995) 92 (17), 7839–7843). Comparison of the amino acid sequence depicted in SEQ ID NO 2 with that of the very well-characterized erythromycin polyketide synthase, eryA ORF1 (Donadio, Science, (1991) 252, 675–679, DNA sequence gene/EMBL accession NO M63676) gives the following results:

Region from SEQ ID NO 2: amino acids 2–325: is 40% identical to the acyltransferase domain of module 2 of the eryA locus of *Saccharopolyspora erythraea*.

Region from SEQ ID NO 2: amino acids 325–470: is 43% identical to the dehydratase domain of module 4 of the eryA locus of *Saccharopolyspora erythraea*.

Region from SEQ ID NO 2: amino acids 762–940: is 48% identical to the ketoreductase domain of module 2 of the eryA locus of *Saccharopolyspora erythraea*.

Region from SEQ ID NO 2: amino acids 1024–1109: is 57% identical to the acyl carrier protein domain of module 2 of the eryA locus of *Saccharopolyspora erythraea*.

Region from SEQ ID NO 2: amino acids 1126–1584: is 59% identical to the ketoacyl synthase domain of module 1 of the eryA locus of *Saccharopolyspora erythraea*.

The very large similarities found in the amino acid sequence and in the size and arrangement of the enzymatic domains suggest that the cloned KpnI region 5.7 kb in size from *A. mediterranei* codes for part of a, polyketide synthase which is typical of polyketides of the macrolide type.

Example 7

Construction of a Cosmid Gene Bank from *A. mediterranei*

The cosmid vector employed is the plasmid pWE15 which can be purchased (Stratagene, La Jolla, Calif., USA). pWE15 is completely cut with the enzyme BamHI (Maniatis et al. 1989) and precipitated with ethanol. For ligation to the cosmid DNA, chromosomal DNA from *A. mediterranei* is isolated as described in Example 1 and partially digested with the restriction enzyme Sau3A (Böhringer, Mannheim) to form DNA fragments most of which have a size of 20–40 kb. The DNA pretreated in this way is fractionated by fragment size by centrifugation (83,000 g, 20° C.) on a 10% to 40% sucrose density gradient for 18 h. The gradient is fractionated in 0.5 ml aliquots and dialysed, and samples of 10 µl are analysed on a 0.3% agarose gel with DNA size standard. Fractions-with chromosomal DNA 25–40 kb in size are combined, precipitated with ethanol and resuspended in a small volume of water.

Ligation of the cosmid DNA to the *A. mediterranei* Sau3A fragments isolated according to their size (see above) takes place with the aid of a T4-DNA ligase. About 3 µg of each of the two DNA starting materials are employed in a reaction volume of 20 µl, and the ligation is carried out at 12° C. for 15 h. 4 ml of this ligation mixture are packaged into lambda phages using the in vitro packaging kit which can be purchased from Stratagene (La Jolla, Calif., USA) (in accordance with the manufacturer's instructions). The resulting phages are introduced by infection into the *E. coli* strain X-1BlueMR® (Stratagene). Titration of the phage material reveals about 20,000 phage particles per ml, analysis of 12 cosmid clones shows that all the clones contain plasmid DNA inserts 25–40 kb in size.

Example 8

Identification, Cloning and Characterization of the Chromosomal *A. mediterranei* DNA Region Which is Adjacent to the Cloned 5.7 kb KpnI Fragment To identify and clone the chromosomal *A. mediterranei* DNA region which is adjacent to the 5.7 kb KpnI fragment described above in Examples 3 and 5, firstly a radioactive DNA probe is prepared from this 5.7 kb KpnI fragment. This is done by-radiolabelling approximately 0.5 µg of the isolated DNA fragment with $^{32}$P-d-CTP by the nick translation system of Gibco/BRL (Basle) in accordance with the manufacturer's instructions.

Infection of *E. coli* X-1 Blue MR (Stratagene) with an aliquot of the lambda phages packaged in vitro (see Example 7) results in more than 2000 clones on several LB+ampicillin (50 µg/ml) plates. These clones are tested by colony hybridization on nitrocellulose filters (see Example 3 for method). The DNA probe used is the 5.7 kb KpnI DNA fragment from *A. mediterranei* which is radiolabelled with $^{32}$P-d-CTP and was prepared above.

5 cosmid clones showing a significant signal with the DNA probe are found. The plasmid DNA of these cosmids is isolated (Sambrook et al., Molecular Cloning: A Laboratory Manual, Cold Spring Harbor Laboratory Press, Cold Spring Harbor, N.Y., 1989), digested with KpnI and analysed in an agarose gel. Analysis reveals that all 5 plasmids have integrated chromosomal *A. mediterranei* DNA with a size of the order of about 25–35 kb, and all contain the 5.7 kb KpnI fragment.

To characterize the chromosomal *A. mediterranei* DNA region which is adjacent to the cloned KpnI fragment, the plasmid DNA of one of the 5 cosmid clones is subjected to restriction analysis. The selected plasmid of the cosmid clone has the number pNE112 and likewise comprises the 13 kb BglII fragment described in Example 3.

Digestion of the plasmid pNE112 with the restriction enzymes BamHI, BglII, HindIII (singularly and in combination) allows a restriction map of the cloned region of *A. mediterranei* to be prepared, and this permits this region about 26 kb in size in the chromosome of *A. mediterranei* to be characterized. This region is characterized by the following restriction cleavage sites with the stated distance in kb from one end: BamHI in position 3.2 kb, HindIII in position 6.6 kb, BglII in position 11.5 kb, BamHI in position 16.6 kb, BamHI in position 17.3 kb, BamHI in position 21 kb and BglII in position 24 kb.

Example 9

Determination of the Sequence of the Chromosomal *A. mediterranei* DNA Region Present in the Plasmid pNE112 and Overlapping with the Cloned 5.7 kb KpnI Fragment The plasmid pNE112 DNA is split up into fragments directly using an Aero-Mist nebulizer (CIS-US Inc., Bedford, Mass., USA) under a nitrogen pressure of 8–12 pounds per square inch. These random DNA fragments are treated with T4 DNA polymerase, T4 DNA kinase and *E. coli* DNA polymerase in the presence of the 4 dNTPs in order to generate blunt ends on the double-stranded DNA fragments (Sambrook et al., Molecular Cloning: A Laboratory Manual, Cold Spring Harbor Laboratory Press, Cold Spring Harbor, N.Y., 1989). The fragments are then fractionated in 0.8% low melting agarose (FMC SeaPlaque Agarose, Catalogue N° 50113), and fragments 1.5–2 kb in size are extracted by hot phenol extraction (Sambrook et al., Molecular Cloning: A Laboratory Manual, Cold Spring Harbor Laboratory Press, Cold Spring Harbor, N.Y., 1989). The DNA fragments obtained in this way are then ligated with the aid of T4 DNA ligase to the plasmid vector pBRKanf4 (see Example 5) or pBlueScript KS+ (Stratagene, La Jolla, Calif., USA), each of which is cut once with square ends by appropriate restriction digestion (SmaI for pBR-Kanf4 and EcoRV for pBlueScript KS+), and is dephosphorylated on the ends by a treatment with alkaline phosphatase (Böhringer, Mannheim). The ligation mixture is then transformed into *E. coli* DH5α, and the cells are incubated overnight on LB agar with the appropriate antibiotic (kanamycin 40 µg/ml for pBRKanf4, ampicillin 100 µg/ml for pBlueScript KS+). Grown colonies are transferred singly into 1.25 ml of liquid TB medium with antibiotic in 96-well plates with wells of a volume of 2 ml, and incubated at 37° C. overnight. Template DNA for the sequencing is prepared directly from these cultures by alkaline lysis (Birnboim, Methods in Enzymology (1983) 100; 243–255). The DNA sequencing takes place using the Perkin Elmer/Appied Biosystems reaction kit with dye-labelled terminator reagents (Kit N° 402122) and universal M13 mp18/19 primers or T3, T7 primers, or with primers prepared by us which bind to internal sequences. A standard cycle sequencing protocol with 20 cycles is used with a thermocycler (MJ Research DNA Engine Thermocycler, Model 225). The sequencing reactions are precipitated with ethanol, resuspended in formamide loading buffer and fractionated and analysed by electrophoresis using the Applied Biosystems automatic DNA sequencer (Model 377) in accordance with the manufacturer's instructions. Sequence files are produced with the aid of the Applied Biosystems DNA Analysis Software computer program and transferred to a SUN UltraSpark computer for further analysis. The following computer programs (software) are employed for analysing the results: DNA assembly and analysis package GAP (Genetics Computer Group, University of Wisconsin, R. Staden, Cambridge University UK) and the four programs: Phred, Crossmatch, Phrad and Consed (P. Green, University of Washington, B. Ewing and D. Gordon, Washington University in Saint Louis). After the original sequences have been connected together to give longer coherent sequences (contigs), missing DNA sections are specifically sequenced with the aid of new primers (binding to sequenced sections), or by longer sequencing or sequencing the other strand.

It is possible with the method described above to sequence the entire chromosomal DNA region 26 kb in size from *A. mediterranei* which is cloned in pNE112. The DNA sequence is depicted in SEQ ID NO 3 in the base pair 27801–53789 section. The DNA sequence of the 5.7 kb KpnI fragment described in Example 5 is present in pNE112, and is depicted in SEQ ID NO 3 in the base pair 43093–48768 region.

Example 10

Identification and Characterization of Cosmid Clones with Chromosomal DNA Fragments from *A. mediterranei* which Overlap with One End of the 26 kb *A. mediterranei* Region of pNE112

To identify cosmid clones which comprise chromosomal DNA fragments from *A. mediterranei* located directly in front of the 26 kb region of pNE112, the plasmid pNE112 is cut with the restriction enzyme BamHI, and the resulting BamHI fragment 3.2 kb in size is separated from the other BamHI fragments in an agarose gel and isolated from the gel. This BamHI fragment is located at one end of the incorporated *A. mediterranei* DNA in pNE112 (see Example 8) and can thus be used as DNA probe for finding the required cosmid clones. Approximately 0.5 µg of the isolated 3.2 kb BamHI DNA fragment is radiolabelled with $^{32}$P-dCTP by the nick translation system from Gibco/BRL (Basel) in accordance with the manufacturer's instructions.

The cosmid gene bank from *A. mediterranei* described in Example 7 is then analysed by colony hybridization (Method of Example 3) using this 3.2 kb DNA probe for clones with overlaps. Two cosmid clones with a strong hybridization signal can be identified in this way and are given the numbers pNE95 and pRi44-2. It is possible by restriction analysis and Southern blot to confirm that the plasmids pNE95 and pRi44-2 comprise chromosomal DNA fragments from *A. mediterranei* which overlap with the 3.2 kb BamHI fragment from pNE112 and together cover a 35 kb chromosomal region of *A. mediterranei* which is directly adjacent to the 26 kb *A. mediterranei* fragment of pNE112 cloned in pNE112.

Example 11

Restriction Analysis of the Chromosomal *A. mediterranei* DNA Region Cloned with the Cosmid Clones pNE112. pNE95 and pRi44-2

The chromosomal *A. mediterranei* DNA region cloned with the cosmid clones pNE112, pNE95 and pRi44-2 is characterized by carrying out a restriction analysis. Digestion of the plasmid DNA of the three cosmids with the restriction enzymes EcoRI, BglII and HindIII (singly and in combination) produces a rough restriction map of the cloned region of *A. mediterranei*. Overlapping fragments of the three plasmids are in this case established and confirmed by Southern blot. This chromosomal region of *A. mediterranei* has a size of about 61 kb and is characterized by the following restriction cleavage sites with the stated distance in kb from one end: EcoRI in position 7.2 kb, HindIII in position 21 kb, BglII in position 31 kb, HindIII in position 42 kb, BglII in position 47 kb and BglII in position 59 kb. In this region in the *A. mediterranei* chromosome, the plasmid pRi 44-2 covers a region from position 1 to approximately 37 kb, plasmid pNE95 covers a region of approximate position 9 kb-51 kb and plasmid pNE 112 covers a region of approximate position 35 kb-61 kb.

Example 12

Determination of the Sequence of the Chromosomal *A. mediterranei* DNA Region Described in Example 11 from the EcoRI Cleavage Site in the 7.2 kb Position up to the 61 kb End Determination of the DNA sequence of the chromosomal region described in Example 11 from *A. mediterranei* (EcoRI cleavage site in the 7.2 kb position to 51 kb) is carried out with the plasmids pRi 44-2 and pNE95, using exactly the same method as described in Example 9. Analysis of the DNA sequence obtained in this way confirms the rough restriction map described in Example 11 and the overlaps of the cloned *A. mediterranei* fragments in the plasmids pNE112, pNE95 and pRi44-2.

The DNA sequence of the chromosomal *A. mediterranei* DNA region described in Example 11 from the EcoRI cleavage site in the 7.2 kb position up to the end at 61 kb is depicted in SEQ ID NO 3 (length 53789 base pairs).

Example 13

Analysis of a First Protein-encoding Region (ORF A) of the Cloned *A. mediterranei* Chromosomal Region Depicted in SEQ ID NO 3

The nucleotide sequence shown in SEQ ID NO 3 is analysed with the Codonpreference computer program (Genetics Computer Group, University of Wisconsin, 1994). This analysis shows that a very large open reading frame (ORF A) which codes for a protein is present in the first third of the sequence (position 1825–15543 including stop codon in SEQ ID NO 3). The codons used in ORF A are typical of actinomycetes genes with a high G+C content.

Comparison of the amino acid sequence of ORF A (SEQ ID NO 4, size 4572 amino acids) with other polyketide synthases and specifically with the very well characterized polyketide synthase of *Saccharopolyspora erythraea* (Donadio, Science, (1991) 252, 675–679, DNA sequence gene/EMBL accession N° M63676) gives the following results:

Region from ORF A. SEQ ID NO 4: amino acids 370–451: is 50% identical to the acyl carrier protein domain of module 1 of the eryA locus of *Saccharopolyspora erythraea*.

Region from ORF A. SEQ ID NO 4: amino acids 469–889: is 65% identical to the ketoacyl synthase domain of module 1 of the eryA locus of *Saccharopolyspora erythraea*.

Region from ORF A. SEQ ID NO 4: amino acids 982–1292: is 54% identical to the acyl-transferase domain of module 1 of the eryA locus of *Saccharopolyspora erythraea*.

Region from ORF A. SEQ ID NO 4: amino acids 1324–1442: is 42% identical to the dehydratase domain of module 4 of the eryA locus of *Saccharopolyspora erythraea*.

Region from ORF A. SEQ ID NO 4: amino acids 1664–1840: is 56% identical to the ketoreductase domain of module 1 of the eryA locus of *Saccharopolyspora erythraea*.

Region from ORF A. SEQ ID NO 4: amino acids 1929–2000: is 53% identical to the acyl carrier protein domain of module 1 of the eryA locus of *Saccharopolyspora erythraea*.
Region from ORF A. SEQ ID NO 4: amino acids 2032–2453: is 64% identical to the ketoacyl synthase domain of module 1 of the eryA locus of *Saccharopolyspora erythraea*.
Region from ORF A. SEQ ID NO 4: amino acids 2554–2865: is 37% identical to the acyl-transferase domain of module 1 of the eryA locus of *Saccharopolyspora erythraea*.
Region from ORF A. SEQ ID NO 4: amino acids 2918–2991: is 54% identical to the acyl carrier protein domain of module 1 of the eryA locus of *Saccharopolyspora erythraea*.
Region from ORF A. SEQ ID NO 4: amino acids 3009–3431: is 65% identical to the ketoacyl synthase domain of module 1 of the eryA locus of *Saccharopolyspora erythraea*.
Region from ORF A. SEQ ID NO 4: amino acids 3532–3847: is 53% identical to the acyl-transferase domain of module 1 of the eryA locus of *Saccharopolyspora erythraea*.
Region of ORF A. SEQ ID NO 4: amino acids 4142–4307: is 43% identical to the ketoreductase domain of module 1 of the eryA locus of *Saccharopolyspora erythraea*.
Region of ORF A. SEQ ID NO 4: amino acids 4405–4490: is 50% identical to the acyl carrier protein domain of module 1 of the eryA locus of *Saccharopolyspora erythraea*.

In addition to these significant homologies with the eryA polyketide synthase of *S. erythraea*, the region of ORF A. SEQ ID NO 4: amino acids 1–356 is 53% identical to the postulated starter unit activation domain of the rapamycin polyketide synthase from *Streptomyces hygroscopicus* (Aparicio et al. GENE (1996) 169, 9–16)

The great similarities found in the amino acid sequence of the enzymatic domains suggest unambiguously that the protein-encoding region (ORF A) of the *A. mediterranai* chromosomal region depicted in SEQ ID NO 3 codes for a typical modular (type 1) polyketide synthase. This very large *A. mediterranei* polyketide synthase encoded by ORF A comprises three complete bioactive modules which are each responsible for condensation of a C2 unit in the macrolide ring of the molecule and correct modification of the initially formed β-keto groups. Because of the homology with activating domains of the rapamycin polyketide synthase, the first module described above very probably comprises an enzymatic domain for activating the aromatic starter unit of rifamycin biosynthesis, 3-amino-5-hydroxybenzoic acid (Ghisalba et al., Biotechnology of Industrial Antibiotics Vandamme E. J. Ed., Decker Inc. New York, (1984) 281–327).

Example 14

Analysis of a Second Protein Encoding Region (ORF B) of the Cloned *A. mediterranei* Chromosomal Region Depicted in SEQ ID NO 3

The nucleotide sequence in SEQ ID NO 3 is analysed using the Codonpreference computer program (Genetics Computer Group, University of Wisconsin, 1994). This analysis shows that another large open reading frame (ORF B) which codes for a protein is present in the middle region of the sequence (position 15550–30759 including stop codon in SEQ ID NO 3). The codons used in ORF B are typical of actinomycetes genes with a high G+C content.

Comparison of the amino acid sequence of ORF B (SEQ ID NO 5, length 5069 amino acids) with other polyketide synthases and specifically with the very well characterized polyketide synthase of *Saccharopolyspora erythraea* (Donadio, Science, (1991) 252, 675–679, DNA sequence gene/EMBL accession N° M63676) gives the following results:

Region of ORF B. SEQ ID NO 5: amino acids 44–468: is 62% identical to the ketoacyl synthase domain of module 1 of the eryA locus of *Saccharopolyspora erythraea*.
Region of ORF B. SEQ ID NO 5: amino acids 571–889: is 56% identical to the acyl-transferase domain of module 1 of the eryA locus of *Saccharopolyspora erythraea*.
Region of ORF B. SEQ ID NO 5: amino acids 921–1055: is 47% identical to the dehydratase domain of module 4 of the eryA locus of *Saccharopolyspora erythraea*.
Region of ORF B. SEQ ID NO 5: amino acids 1353–1525: is 49% identical to the ketoreductase domain of module 1 of the eryA locus of *Saccharopolyspora erythraea*.
Region of ORF B. SEQ ID NO 5: amino acids 1621–1706: is 53% identical to the acyl carrier protein domain of module 1 of the eryA locus of *Saccharopolyspora erythraea*.
Region of ORF B. SEQ ID NO 5: amino acids 1726–2148: is 62% identical to the ketoacyl synthase domain of module 1 of the eryA locus of *Saccharopolyspora erythraea*.
Region of ORF B. SEQ ID NO 5: amino acids 2251–2560: is 55% identical to the acyl-transferase domain of module 1 of the eryA locus of *Saccharopolyspora erythraea*.
Region of ORF B. SEQ ID NO 5: amino acids 2961–3132: is 49% identical to the ketoreductase domain of module 1 of the eryA locus of *Saccharopolyspora erythraea*.
Region of ORF B. SEQ ID NO 5: amino acids 3228–3313: is 52% identical to the acyl carrier protein domain of module 1 of the eryA locus of *Saccharopolyspora erythraea*.
Region of ORF B. SEQ ID NO 5: amino acids 3332–3755: is 63% identical to the ketoacyl synthase domain of module 1 of the eryA locus of *Saccharopolyspora erythraea*.
Region of ORF B. SEQ ID NO 5: amino acids 3857–4173: is 52% identical to the acyl-transferase domain of module 1 of the eryA locus of *Saccharopolyspora erythraea*.
Region of ORF B. SEQ ID NO 5: amino acids 4664–4799: is 47% identical to the ketoreductase domain of module 1 of the eryA locus of *Saccharopolyspora erythraea*.
Region of ORF B. SEQ ID NO 5: amino acids 4929–5014: is 52% identical to the acyl carrier protein domain of module 1 of the eryA locus of *Saccharopolyspora erythraea*.

Example 15

Analysis of a Third Protein-encoding Region (ORF C) of the Cloned *A. mediterranei* Chromosomal Region Depicted in SEQ ID NO 3

The nucleotide sequence in SEQ ID NO 3 is analysed using the Codonpreference computer program (Genetics Computer Group, University of Wisconsin, 1994). This analysis shows that a large open reading frame (ORF C) which codes for a protein is present in the middle region of the sequence (position 30895–36060 including stop codon in SEQ ID NO 3). The codons used in ORF C are typical of actinomycetes genes with a high G+C content.

Comparison of the amino acid sequence of ORF C (SEQ ID NO 6, length 1721 amino acids) with other polyketide synthases and specifically with the very well characterized polyketide synthase from *Saccharopolyspora erythraea* (Donadio, Science, (1991) 252, 675–679, DNA sequence gene/EMBL accession N° M63676) gives the following results:

Region of ORF C. SEQ ID NO 6: amino acids 1–414: is 63% identical to the ketoacyl synthase domain of module 1 of the eryA locus of *Saccharopolyspora erythraea*.

Region of ORF C. SEQ ID NO 6: amino acids 514–828: is 54% identical to the acyl-transferase domain of module 1 of the eryA locus of *Saccharopolyspora erythraea*.

Region of ORF C. SEQ ID NO 6: amino acids 1290–1399: is 49% identical to the ketoreductase domain of module 1 of the eryA locus of *Saccharopolyspora erythraea*.

Region of ORF C. SEQ ID NO 6: amino acids 1563–1648: is 55% identical to the acyl carrier protein domain of module 1 of the eryA locus of *Saccharopolyspora erythraea*.

Example 16

Analysis of a Fourth Protein-encoding Region (ORF D) of the Cloned *A. mediterranei* Chromosomal Region Depicted in SEQ ID NO 3

The nucleotide sequence in SEQ ID NO 3 is analysed using the Codonpreference computer program (Genetics Computer Group, University of Wisconsin, 1994). This analysis shows that a large open reading frame (ORF D) which codes for a protein is present in the middle region of the sequence (position 36259–41325 including stop codon in SEQ ID NO 3). The codons used in ORF D are typical of actinomycetes genes with a high G+C content.

Comparison of the-amino acid sequence of ORF D (SEQ ID NO 7, length 1688 amino acids) with other polyketide synthases and specifically with the very well characterized polyketide synthase from *Saccharopolyspora erythraea* (Donadio, Science, (1991) 252, 675–679, DNA sequence genes/EMBL accession N° M63676) gives the following results:

Region of ORF D. SEQ ID NO 7: amino acids 1–418: is 64% identical to the ketoacyl synthase domain of module 1 of the eryA locus of *Saccharopolyspora erythraea*.

Region of ORF D. SEQ ID NO 7: amino acids 524–841: is 54% identical to the acyl-transferase domain of module 1 of the eryA locus of *Saccharopolyspora erythraea*.

Region of ORF D. SEQ ID NO 7: amino acids 1260–1432: is 51% identical to the ketoreductase domain of module 1 of the eryA locus of *Saccharopolyspora erythraea*.

Region of ORF D. SEQ ID NO 7: amino acids 1523–1608: is 53% identical to the acyl carrier protein domain of module 1 of the eryA locus of *Saccharopolyspora erythraea*.

Example 17

Analysis of a Fifth Protein-encoding Region (ORF E) of the Cloned *A. mediterranei* Chromosomal Region Depicted in SEQ ID NO 3

The nucleotide sequence in SEQ ID NO 3 is analysed using the Codonpreference computer program (Genetics Computer Group, University of Wisconsin, 1994). This analysis shows that a large open reading frame (ORF E) which codes for a protein is present in the rear region of the sequence (position 41373–51614 including stop codon in SEQ ID NO 3). The codons used in ORF E are typical of actinomycetes genes with a high G+C content.

Comparison of the amino acid sequence of ORF E (SEQ ID NO 8, length 3413 amino acids) with other polyketide synthases and specifically with the very well characterized polyketide synthase from *Saccharopolyspora erythraea* (Donadio, Science, (1991) 252, 675–679, DNA sequence gene/EMBL accession N° M63676) gives the following results:

Region of ORF E. SEQ ID NO 8: amino acids 31–451: is 64% identical to the ketoacyl synthase domain of module 1 of the eryA locus of *Saccharopolyspora erythraea*.

Region of ORF E. SEQ ID NO 8: amino acids 555–874: is 37% identical to the acyl-transferase domain of module 1 of the eryA locus of *Saccharopolyspora erythraea*.

Region of ORF E. SEQ ID NO 8: amino acids 907–1036: is 49% identical to the dehydratase domain of module 4 of the eryA locus of *Saccharopolyspora erythraea*.

Region of ORF E. SEQ ID NO 8: amino acids 1336–1500: is 52% identical to the ketoreductase domain of module 1 of the eryA locus of *Saccharopolyspora erythraea*.

Region of ORF E. SEQ ID NO 8: amino acids 1598–1683: is 51% identical to the acyl carrier protein domain of module 1 of the eryA locus of *Saccharopolyspora erythraea*.

Region of ORF E. SEQ ID NO 8: amino acids 1702–2124: is 62% identical to the ketoacyl synthase domain of module 1 of the eryA locus of *Saccharopolyspora erythraea*.

Region of ORF E, SEQ ID NO 8: amino acids 2229–2543: is 53% identical to the acyl-transferase domain of module 1 of the eryA locus of *Saccharopolyspora erythraea*.

Region of ORF E. SEQ ID NO 8: amino acids 2573–2700: is 47% identical to the dehydratase domain of module 4 of the eryA locus of *Saccharopolyspora erythraea*.

Region of ORF E. SEQ ID NO 8: amino acids 3054–3227: is 52% identical to the ketoreductase domain of module 1 of the eryA locus of *Saccharopolyspora erythraea*.

Region of ORF E. SEQ ID NO 8: amino acids 3324–3405: is 51% identical to the acyl carrier protein domain of module 1 of the eryA locus of *Saccharopolyspora erythraea*.

Example 18

Analysis of a Sixth Protein-encoding Region (ORF F) of the Cloned *A. mediterranei* Chromosomal Region Depicted in SEQ ID NO 3

The nucleotide sequence in SEQ ID NO 3 is analysed using the Codonpreference computer program (Genetics Computer Group, University of Wisconsin, 1994). This analysis shows that an open reading frame (ORF F) which codes for a protein is present in the rear region of the sequence (position 51713–52393 including stop codon in SEQ ID NO 3). The codons used in ORF F are typical of actinomycetes genes-with a high G+C content.

Comparison of the amino acid sequence of ORF F (SEQ ID NO 9, length 226 amino acids) with proteins from the EMBL databank (Heidelberg) shows a great similarity with the N-hydroxyarylamine O-acyltransferase from *Salmonella typhimurium* (29% identity over a region of 134 amino acids). There is also significant homology with arylamine acyl-transferases from other organisms. It can be concluded from these agreements that the ORF F found in *A. mediter-*

*ranei* in SEQ ID No 3 codes for an arylamine acyl transferase, and it can be assumed that this enzyme is responsible for the linkage of the long acyl chain produced by the polyketide synthase to the amino group on the starter molecule, 3-amino-5-hydroxybenzoic acid. This reaction would close the rifamycin ring system correctly after completion of the condensation steps by the polyketide synthase.

Example 19

Summarizing Assessment of the Function of the Proteins Encoded by ORF A-F in SEQ ID NO 3, and their Role in the Biosynthesis of Rifamycin The five protein-encoding regions (ORF A-E), described in Examples 13–17, of SEQ ID NO 3 comprise proteins with very great similarity (in the amino acid sequence and the arrangement of the enzymatic domains) to polyketide synthases for polyketides of the macrolide type. Taken together, these five multifunctional enzymes comprise 10 polyketide synthase modules which are each responsible for a condensation step in the polyketide synthesis. 10 such condensation steps are likewise necessary for rifamycin biosynthesis (Ghisalba et al., Biotechnology of Industrial Antibiotics Vandamme E. J. Ed., Decker Inc. New York, (1984) 281–327). The processing of the particular keto groups required by the enzymatic domains within the modules substantially corresponds to the activity required by the rifamycin molecule, if it is assumed that the polyketide synthesis takes place "colinearly" with the arrangement of the modules in the gene cluster of *A. mediterranei* (this is so for other macrolide antibiotics such as erythromycin and rapamycin). It may be added here that it is not certain whether transcription of the five ORFs results in five proteins; in particular, ORF C and ORF D might possibly be translated to a large protein.

An enzymatic domain which is very probably responsible for activating the starter molecule, 3-hydroxy-5-aminobenzoic acid, of rifamycin biosynthesis can be found at the N terminus of OAF A, the start of the polyketide synthase. Directly below the described rifamycin polyketide synthase gene cluster there is a gene (ORF F) which very probably determines a protein which brings about ring closure of the rifamycin molecule after completion of the condensation steps by the polyketide synthase.

It can be concluded on the basis of these findings that the *A. mediterranei* chromosomal region described in SEQ ID NO 3 is responsible for the ten condensation steps required for rifamycin polyketide synthesis, including activation of the starter molecule 3-hydroxy-5-aminobenzoic acid, and the concluding ring closure.

Deposited Microorganisms

The following microorganisms and plasmids have been deposited at the Deutsche Sammlung von Mikroorganismen und Zelikulturen GmbH (DSM), Mascheroder Weg 1b, D-38124 Braunschweig, in accordance with the requirements of the Budapest Treaty.

| Microorganism/Plasmid | Date of deposit | Deposit number |
|---|---|---|
| E. coli with plasmid pRi7-3 | Aug. 10, 1996 | DSM 11114 |
| E. coil with plasmid pNE112 | Jul. 14, 1997 | DSM 11657 |
| E. coil with plasmid pNE95 | Jul. 14, 1997 | DSM 11656 |
| E. coil with plasmid pRi44-2 | Jul. 14, 1997 | DSM 11655 |

What is claimed is:

1. An isolated DNA fragment wherein said fragment has 90% or greater sequence homology to a region of SEQ ID NO 3 and wherein said fragment encodes one or more of the proteins or polypeptides having a rifamycin biosynthesis enzymatic function possessed by a rifamycin biosynthesis protein selected from the group consisting of the proteins encoded by ORF A, B, C, D, E and F of the *Amycolatopsis mediterranei* rifamycin synthesis gene cluster.

2. An isolated DNA fragment according to claim 1, wherein said fragment comprises a nucleotide sequence selected from the group consisting of ORF A, B, C, D, E, F, or encodes one or more of the proteins or polypeptides, depicted in SEQ ID NOS 4 to 9.

3. An isolated DNA fragment according to claim 1, wherein said fragment comprises SEQ ID NO 4.

4. A hybrid vector comprising a DNA fragment according to claim 1.

5. A hybrid vector comprising an expression vector comprising a DNA fragment according to claim 1.

6. A host organism comprising a hybrid vector according to claim 4.

7. A method for identifying DNA fragments of genes that encode ansamycin biosynthesis enzymes, comprising the steps of:

(1) obtaining a single-stranded nucleotide having at least 15 consecutive nucleotides from an isolated DNA fragment according to claim 1, (2) obtaining genomic DNA from an organism that biosynthesizes an ansamycin;

(3) hybridizing the single-stranded nucleotide to the genomic DNA to yield a hybridization product; and (4) selecting the hybridization product, wherein the selection identifies the genomic DNA as a DNA fragment of a gene that encodes an ansamycin biosynthesis enzyme.

* * * * *